(12) United States Patent
Cheng et al.

(10) Patent No.: US 9,028,880 B2
(45) Date of Patent: May 12, 2015

(54) SILICA NANOPARTICLE AGENT CONJUGATES

(75) Inventors: Jianjun Cheng, Champaign, IL (US); Li Tang, Quincy, MA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 13 days.

(21) Appl. No.: 13/990,712

(22) PCT Filed: Nov. 30, 2011

(86) PCT No.: PCT/US2011/062548
§ 371 (c)(1),
(2), (4) Date: Jun. 24, 2013

(87) PCT Pub. No.: WO2012/075087
PCT Pub. Date: Jun. 7, 2012

(65) Prior Publication Data
US 2013/0274226 A1    Oct. 17, 2013

Related U.S. Application Data

(60) Provisional application No. 61/418,230, filed on Nov. 30, 2010.

(51) Int. Cl.
*A61K 47/48* (2006.01)
*A61K 49/00* (2006.01)
*A61K 9/00* (2006.01)
*A61K 9/12* (2006.01)
*A61K 9/20* (2006.01)
*A61K 9/48* (2006.01)
*B82B 1/00* (2006.01)

(52) U.S. Cl.
CPC ......... *A61K 47/48861* (2013.01); *A61K 9/0019* (2013.01); *A61K 9/12* (2013.01); *A61K 9/2054* (2013.01); *A61K 9/4858* (2013.01); *A61K 49/0032* (2013.01); *A61K 49/0041* (2013.01); *A61K 49/0095* (2013.01); *B82B 1/008* (2013.01); *Y10S 977/773* (2013.01)

(58) Field of Classification Search
None
See application file for complete search history.

(56) References Cited

U.S. PATENT DOCUMENTS

| | | | |
|---|---|---|---|
| 6,462,100 B1 * | 10/2002 | Thunhorst et al. | 521/53 |
| 2010/0035365 A1 * | 2/2010 | Wiesner et al. | 436/501 |
| 2010/0297246 A1 | 11/2010 | Weitzmann et al. | |
| 2013/0064776 A1 * | 3/2013 | El Harrak et al. | 424/9.6 |

FOREIGN PATENT DOCUMENTS

WO    WO 2008034124    *    3/2008

OTHER PUBLICATIONS

Abdelwashed et al. "Freeze-drying of nanoparticles:Formulation, process and storage considerations", Adanced Drug Delivery Reviews (Dec. 30, 2006) 58 (15) 1688-1713 and 1693-1694.*
Hu et al. "Nanoparticle-assisted combination therapies for effective cancer treatment" Therapeutic Delivery (201) 1(2), 323-334.*
Abdelwahed et al., "Freeze-drying of nanoparticles: Formulation, process and storage considerations," Advanced Drug Delivery Reviews (Dec. 30, 2006) 58 (15): 1688-1713 and 1693-1694.
Nistor et al., "Encapsulation of three different hydrophobic dyes in functionalized silica particles," Journal of Sol-Gel Science and Technology (Apr. 19, 2011) 59 (1): 48-56.
International Search Report and Written Opinion for corresponding International Application No. PCT/US2011/062548 mailed on Oct. 1, 2012.

* cited by examiner

*Primary Examiner* — Robert A Wax
*Assistant Examiner* — Danah Al-Awadi
(74) *Attorney, Agent, or Firm* — Haukaas Fish PLLC; Michael H. Haukaas

(57) ABSTRACT

The invention provide a silica nanoparticle comprising a non-porous matrix of silicon-oxygen bonds, wherein the matrix comprises organic agents conjugated to silicon or oxygen atoms in the matrix, the organic agents are conjugated to the matrix through linker L groups, wherein the linker L comprises, for example, an ester, urea, thiourea, or thio ether group, and wherein the diameter of the nanoparticle is about 15 nm to about 200 nm. The invention also provides novel methods of making and using the silica nanoparticles described herein.

24 Claims, 18 Drawing Sheets

| Probe | Structure | Modality for imaging |
|---|---|---|
| Pyrene | 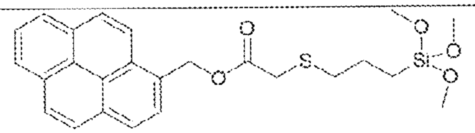 | fluorescence (ex. 340 nm; em. 376 nm [a]) |
| Rhodamine | 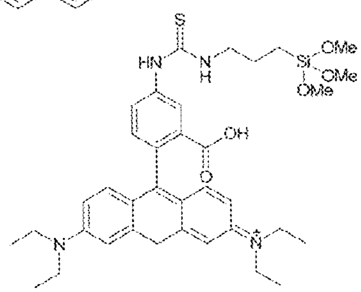 | fluorescence (ex. 560 nm; em. 580 nm) |
| IR783 | 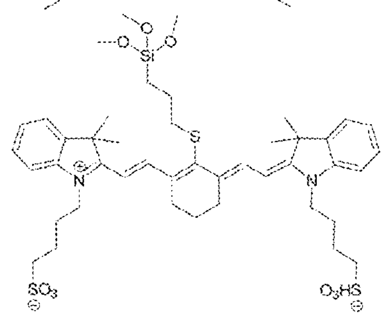 | fluorescence (ex. 780 nm; em. 810 nm) |
| Gd-EDTA-sil | 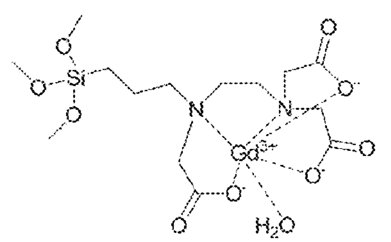 | Magnetic resonance imaging (MRI) |
| 64Cu-EDTA-sil | 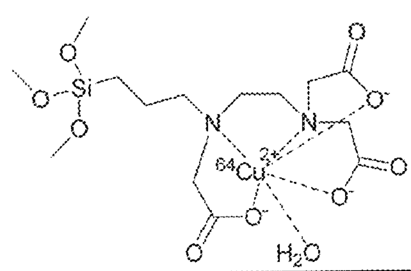 | Positron emission tomography (PET) |

*Figure 14*

SILICA NANOPARTICLE AGENT CONJUGATES

RELATED APPLICATIONS

This application is a National Stage Application of PCT/US2011/062548, filed on Nov. 30, 2011, which claims priority under 35 U.S.C. §119(e) to U.S. Provisional Patent Application No. 61/418,230, filed Nov. 30, 2010 and which applications are incorporated herein by reference. A claim of priority to all, to the extent appropriate, is made.

GOVERNMENT SUPPORT

This invention was made with government support under Grant No. 0748834-CAREER, awarded by the National Science Foundation. The United States Government has certain rights in the invention.

BACKGROUND OF THE INVENTION

Nanomedicine is an emerging field that is expected to alter the landscape of oncology. In the past 20-30 years, efforts have been mainly devoted to the development of polymeric nanomedicine technology (micelles, nanoparticles, polymer-drug conjugates, and the like) that can be formulated by copolymer self-assembly, nanoprecipitation or conjugation, which can accumulate in tumors via Enhanced Permission and Retention (EPR), a passive targeting mechanism.

Although significant progress has been made, the conventional formulations usually afford drug delivery nanostructures with random and wide-ranging particle sizes. The size of drug delivery vehicles has been strongly correlated with their in vivo biodistribution, penetration in tumor tissue and intracellular trafficking. Particle size of a therapeutic nanoparticle, therefore, has a significant impact on antitumor efficacy.

Size control has been achieved recently with the use of top-down technology. However, it is still a significant obstacle to make large quantity of nanoparticles with controlled sizes, especially nanoparticles with diameters less than 100 nm, which size is favorable for tumor accumulation. Accordingly, what is needed are new nanoparticles that can be prepared on a large scale with controlled sizes.

SUMMARY

Nanoparticulate drug delivery vehicles, exemplified by micelles and nanoparticles (NPs) roughly in the 1-200 nm size range, have attracted much interest in recent decades as alternative modalities for cancer treatment and diagnosis. The size of these drug delivery vehicles has been strongly correlated with their in vivo biodistribution, penetration in tumor tissue and intracellular trafficking. Their size therefore has significant impact on antitumor efficacy. However, it is challenging to make large quantity of monodisperse NPs with controlled sizes, especially particles smaller than 100 nm, for drug delivery applications.

A novel drug delivery platform based on drug conjugated silica NPs with nearly any desired size from 20 to 200 nm is described herein. The NPs can be readily prepared on a multi-gram scale. Various studies of size effects both in vitro and in vivo demonstrate that drug conjugated silica NPs of less then 50 nm in diameter have significantly superior properties than their larger sized counterparts, indicating their suitability for applications in cancer therapy.

The invention thus provides nanoparticles, including silica drug-conjugated nanoparticles, and methods for using and preparing them. Degradable nanoparticles and nanoparticles of monodisperse particle sized can be prepared using the methods described herein.

Accordingly, the invention provides a silica nanoparticle comprising a non-porous matrix of silicon-oxygen bonds, wherein the matrix comprises organic agents conjugated to silicon or oxygen atoms in the matrix, the organic agents are conjugated to the matrix through linker L groups, wherein the linker L comprises an ester, acetal, urea, thiourea, or thio ether group, and wherein the diameter of the nanoparticle is about 15 nm to about 200 nm. The organic agents can be located at the surface of the nanoparticle, inside the surface of the nanoparticle, or both. The organic agent can be a drug, a diagnostic agent, a surface modification agent, or a combination thereof.

The silica nanoparticle can degrade under physiological conditions, for example, inside the body of an animal. The organic agent can be hydrolyzed from the linker L of the silica nanoparticle with controlled release kinetics under such physiological conditions. The linker L can be responsively degradable.

The surface of the nanoparticles can include surface-modifying groups. The surface-modifying group can include polyethylene glycol (PEG) groups, amine groups, carboxyl groups, and the like. The PEG groups can be of any suitable molecular weigh, for example, about 500 to about 20,000 Da, or about 1,000 to about 10,000 Da. The drug loaded in the nanoparticle can be, for example, paclitaxel, camptothecin, docetaxel, doxorubicin, or other hydroxyl-containing drugs. The diagnostic agent can be, for example, an optical imaging agent, a magnetic resonance imaging agent, or a positron emission tomography agent. Examples of diagnostic agents include fluorescent dyes, such as pyrene, rhodamine, and near infra-red dyes such as IR783. Other examples of diagnostic agents that can be conjugated to nanoparticles include reagents such as gadolinium complexes (e.g., Gd-EDTA) for MRI or radio isotope analysis, such as $^{99m}$Tc or $^{64}$Cu (e.g., $^{64}$Cu-EDTA) for positron emission tomography analysis.

In various embodiments, the linker L can be one or more of:

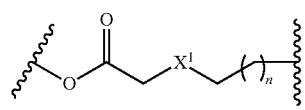

wherein n is 0-8 and $X^1$ is $CH_2$ or S;

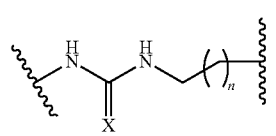

wherein n is 0-8 and X is O or S; or c) —$(C_1$-$C_8)$alkyl-S—.

The silica nanoparticle silica nanoparticle matrix can also include one or more Si-ester-Si groups, Si-acetal-Si groups, or both; wherein the Si-ester-Si group comprises a moiety of Formula I:

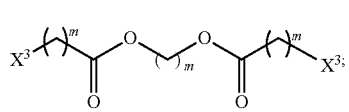

(I)

wherein each m is independently 1-8 and each $X^3$ is a silicon atom of the silica nanoparticle matrix; and wherein the Si-acetal-Si group comprises a moiety of Formula II:

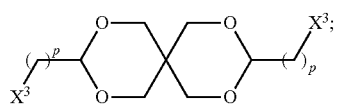

(II)

wherein each p is independently 1-8 and each $X^3$ is a silicon atom of the silica nanoparticle matrix. For example, the silica nanoparticle matrix can include one or more Si-ester-Si groups, Si-acetal-Si groups, or both; wherein the Si-ester-Si group comprises a moiety of Formula IA:

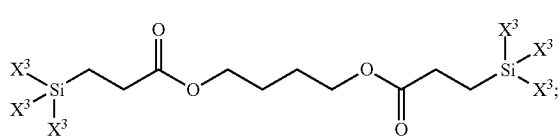

(IA)

wherein each $X^3$ is an oxygen atom of the silica nanoparticle matrix; and wherein the Si-acetal-Si group comprises a moiety of Formula IIA:

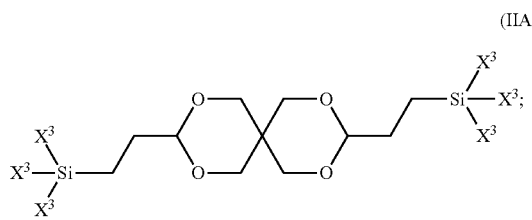

(IIA)

wherein each $X^3$ is an oxygen atom of the silica nanoparticle matrix.

The silica nanoparticle can have a variety of precisely controlled monodisperse sizes. For example, the diameters of the silica nanoparticles can be substantially monodisperse diameters of about 190 nm to about 200 nm, about 170 nm to about 180 nm, about 160 nm to about 170 nm, about 150 nm to about 160 nm, about 140 nm to about 150 nm, about 100 nm to about 110 nm, about 90 nm to about 100 nm, about 80 nm to about 90 nm, about 40 nm to about 60 nm, about 40 nm to about 50 nm, about 20 nm to about 30 nm, or about 15 nm to about 25 nm.

The invention also provides a method of preparing organic agent conjugated silica nanoparticles comprising:

a) combining tetraethyl orthosilicate (TEOS) or tetramethyl orthosilicate (TMOS) and optionally one or more Si-ester-Si compounds, Si-acetal-Si compounds, or both;

wherein the Si-ester-Si compound comprises a moiety of Formula IB:

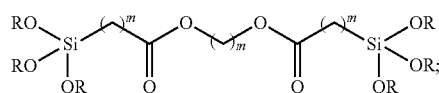

(IB)

wherein each m is independently 1-8 and each R is independently $(C_1$-$C_4)$alkyl; and wherein the Si-acetal-Si compound comprises a moiety of Formula IIB:

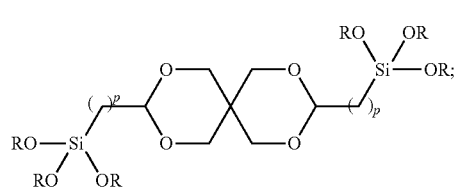

(IIB)

wherein each p is independently 1-8 and each R is independently $(C_1$-$C_4)$alkyl;

with methanol or ethanol; water, and ammonium hydroxide, to provide a first mixture;

b) adding a plurality of organic agents to the first mixture, wherein each organic agent is conjugated to a trialkoxysilane group, to provide a second mixture; and c) stirring or agitating the second mixture;

to provide the organic agent conjugated silica nanoparticles, wherein the silica nanoparticles comprise non-porous matrixes of silicon-oxygen bonds, wherein the matrix comprises organic agents conjugated to silicon or oxygen atoms in the matrix, the organic agents are conjugated to the matrix through linker L groups, wherein the linker L comprises an ester, urea, thiourea, or thio ether group, and wherein the diameter of the nanoparticle is about 15 nm to about 200 nm.

The surfaces of the silica nanoparticles can be modified by combining the second mixture with PEG conjugated trialkoxysilanes, to provide silica nanoparticles with PEG moieties conjugated to the surface of the nanoparticles. The silica nanoparticles can be isolated by, for example, centrifugation or filtration.

The invention also provides a method of preparing organic agent conjugated silica nanoparticles comprising:

a) combining cyclohexane, hexanol, and a non-ionic surfactant comprising a phenyl moiety substituted by a $(C_6$-$C_{10})$ alkyl group and a PEG group having 6-12 ethylene oxide units, to provide a first mixture;

b) combining the first mixture with water, tetraethyl orthosilicate (TEOS) or tetramethyl orthosilicate (TMOS), optionally one or more Si-ester-Si compounds, Si-acetal-Si compounds, or both;

wherein the Si-ester-Si compound comprises a moiety of Formula IB:

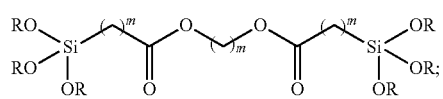

(IB)

wherein each m is independently 1-8 and each R is independently $(C_1$-$C_4)$alkyl; and wherein the Si-acetal-Si compound comprises a moiety of Formula IIB:

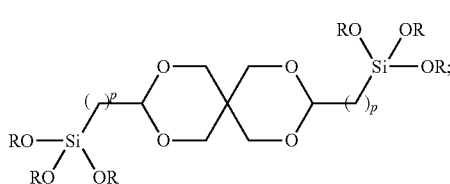

(IIB)

wherein each p is independently 1-8 and each R is independently $(C_1-C_4)$alkyl, and a plurality of organic agents, wherein each organic agent is conjugated to a trialkoxysilane group, to provide a second mixture; and c) combining the second mixture with ammonium hydroxide with stirring or agitation, to provide the organic agent conjugated silica nanoparticles, wherein the silica nanoparticles comprise non-porous matrixes of silicon-oxygen bonds, wherein the matrix comprises organic agents conjugated to silicon or oxygen atoms in the matrix, the organic agents are conjugated to the matrix through linker L groups, wherein the linker L comprises an ester, urea, thiourea, or thio ether group, and wherein the diameter of the nanoparticle is about 15 nm to about 200 nm.

The surfaces of these silica nanoparticles can also be modified by combining organic agent conjugated silica nanoparticles with PEG conjugated trialkoxysilanes, to provide silica nanoparticles with PEG moieties conjugated to the surface of the nanoparticles. The silica nanoparticles can be isolated by centrifugation or filtration.

The invention yet further provides methods of enhancing the penetration of a drug into a tumor comprising administering an effective amount of a plurality of silica nanoparticles described herein to a mammal that has a tumor, wherein the particles enter the tumor, and the nanoparticles release the drug to the tumor. In some embodiments, the diameter of one or more of the drug conjugated silica nanoparticles is less than about 100 nm. Also provided is a method for delivering a therapeutic agent to an animal in need of treatment with the agent comprising administering silica nanoparticles as described herein to the animal, wherein the therapeutic agent releases from the linker L under the physiological conditions of the animal, thereby delivering the therapeutic agent to the animal.

The invention yet further provides a pharmaceutical composition comprising a plurality of silica nanoparticles described herein and a pharmaceutically acceptable diluent, excipient, or carrier.

The invention also provides for the use of the nanoparticles and compositions described herein for use in medical therapy and diagnostic analysis. The medical therapy can be treating cancer, for example, breast cancer, lung cancer, pancreatic cancer, prostate cancer, or colon cancer. The diagnostic analysis can be, for example, imaging an organ or a tumor. The invention also provided for the use of nanoparticles or a composition as described herein for the manufacture of a medicament to treat cancer tumors. The medicament can include a pharmaceutically acceptable diluent, excipient, or carrier. The invention further provides for the use of the nanoparticles described herein for the manufacture of medicaments useful for the treatment of adverse conditions in a mammal, such as the treatment of cancerous tumors. Also provided are useful methods and chemical intermediates for the preparation of the particles and compositions disclosed herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 14. Examples of various imaging probes that can be incorporated to silica nanoparticles, according to various embodiments.

DETAILED DESCRIPTION

Definitions

Figure 1A:
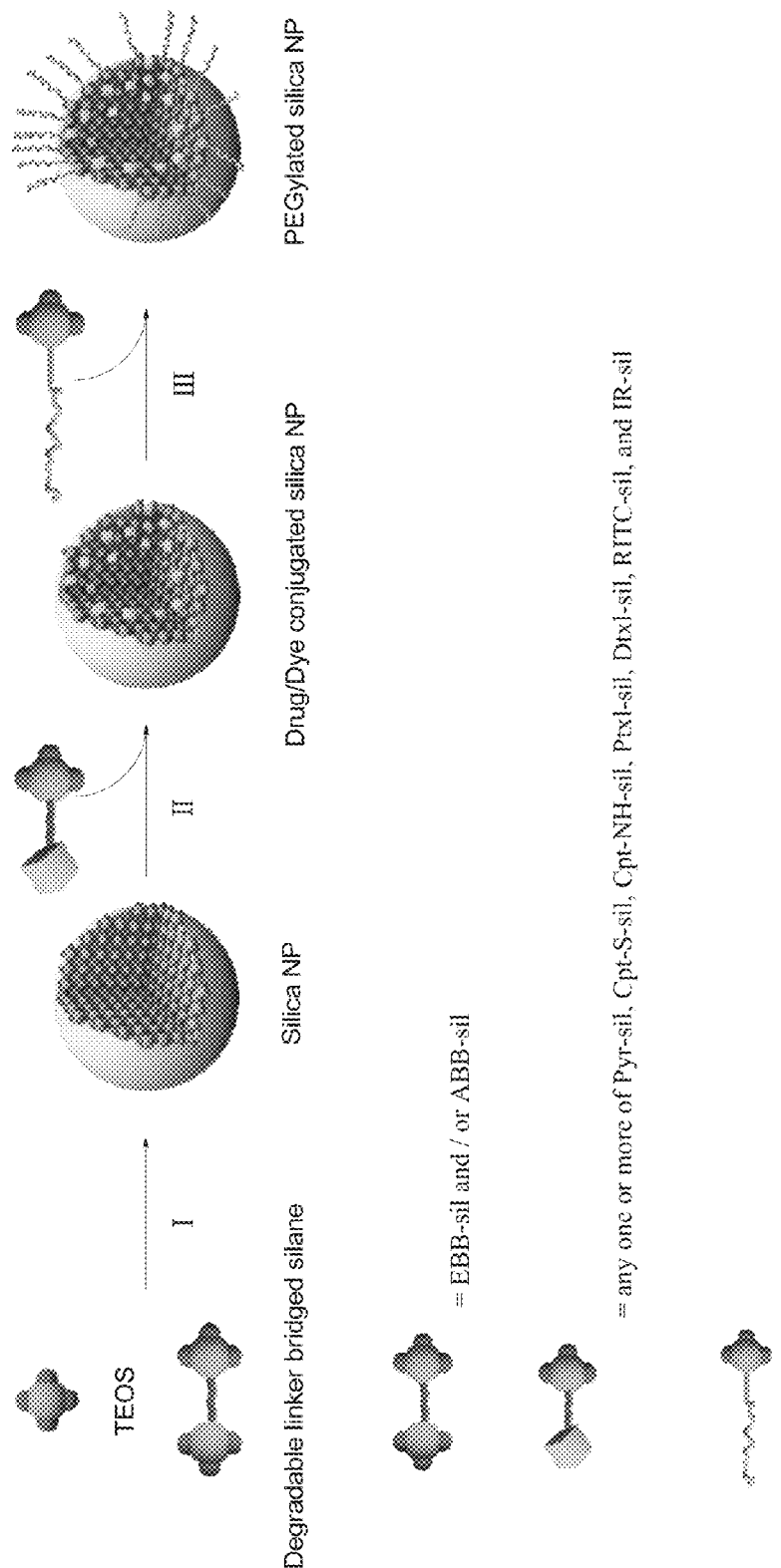
FIG. 1. Drug conjugated silica nanoparticle preparation and starting materials. (A): Schematic showing of the preparation of drug conjugated silica nanoparticles: I, $NH_3.H_2O$/MeOH as the Stöber method; II, $NH_3.H_2O$ for compounds EBB-sil, Pyr-sil, or Cpt-S-sil, NaF for ABB-sil; III surface PEGylation using mPEG-sil; (B): sil conjugate starting materials of various embodiments that can be used to prepare nanoparticles of the invention.

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "trialkoxysilane" refers to a group that includes a silicon atom tri-substituted by alkoxy groups. The alkoxy groups can be, for example, ($C_1$-$C_8$)alkoxy groups or ($C_1$-$C_4$) alkoxy groups. Specific examples include trimethoxy silanes ($Me_3Si$—) and triethoxy silianes ($Et_3Si$—).

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "responsively degradable" refers to the property of a particle or linking group in a particle where the particle or group is degradable and the degradation is triggered by a particular signal. The signal can be, for example, a change in pH (either an increase or decrease), a change in redox potential, or the presence of UV light or near infrared light.

Nanoparticle Drug Delivery Systems

Nanoparticulate drug delivery vehicles are typically prepared through bottom-up approaches, such as self-assembly of amphiphilic copolymers and nanoprecipitation of hydrophobic polymers for the preparation of micelles and nanoparticles (NPs), respectively. The micellation and nanoprecipitation methods allow for facile preparation of vehicles in gram- or larger scale. However, the drawback of these methods is readily apparent. The resulting micelles or NPs typically have a broad size distribution, which can be problematic for clinically viable drug formulations.

Recently there has been increasing amounts of evidence showing that NP size plays a vital role in controlling systemic and lymphatic biodistribution, in vivo targeting and tumor penetration of particulate drug delivery vehicles (Perrault et al., Nano Lett. 9, 1909-1915 (2009); Fox et al., Acc. Chem. Res. 42, 1141-1151 (2009)). NPs with monodisperse size distribution can be prepared via top-down approaches, taking advantage of the fast-evolving micro- and nano-fabrication technologies (Gratton et al., Proc. Natl. Acad. Sci. U.S.A. 105, 11613-11618 (2008)). However, preparation of sub-100 nm NPs in large-scale (gram- or larger scale) for their preclinical or clinical applications is still technically challenging and expensive. To the best of applicants' knowledge, there are no fabrication approaches that allow for the formulation of drug delivery NPs that suitably address both size homogeneity and NP scalability issues.

To address these issues, a unique strategy has been developed that allows for the formulation of drug conjugated silica nanoparticles on at least gram-scale, with monodisperse sizes, controllable from about 20 to about 200 nm (FIG. 1). Monodisperse silica NPs can be prepared on a large scale with discrete particle sizes via acid or base induced hydrolysis and condensation reaction of tetraethyl orthosilicate (TEOS) or tetramethyl orthosilicate (TMOS) (Barbe et al., Adv. Mater. 16, 1959-1966 (2004)). Besides TEOS and TMOS, other silane coupling agents containing a trialkoxysilane group (sil) can be incorporated into silica NPs through the similar hydrolysis and condensation reactions (Stein et al., *Adv. Mater.* 12, 1403-1419 (2000)). As described herein, it was discovered that when a therapeutic agent linked to a trialkoxysilane group through a degradable linker, referred to as a "drug containing silane coupling agent (Drug-sil)", is used for co-condensation with TEOS or TMOS, drug molecules can be incorporated into silica NPs with well controlled NP sizes by taking advantage of unique properties of silica NPs.

Figure 1B:
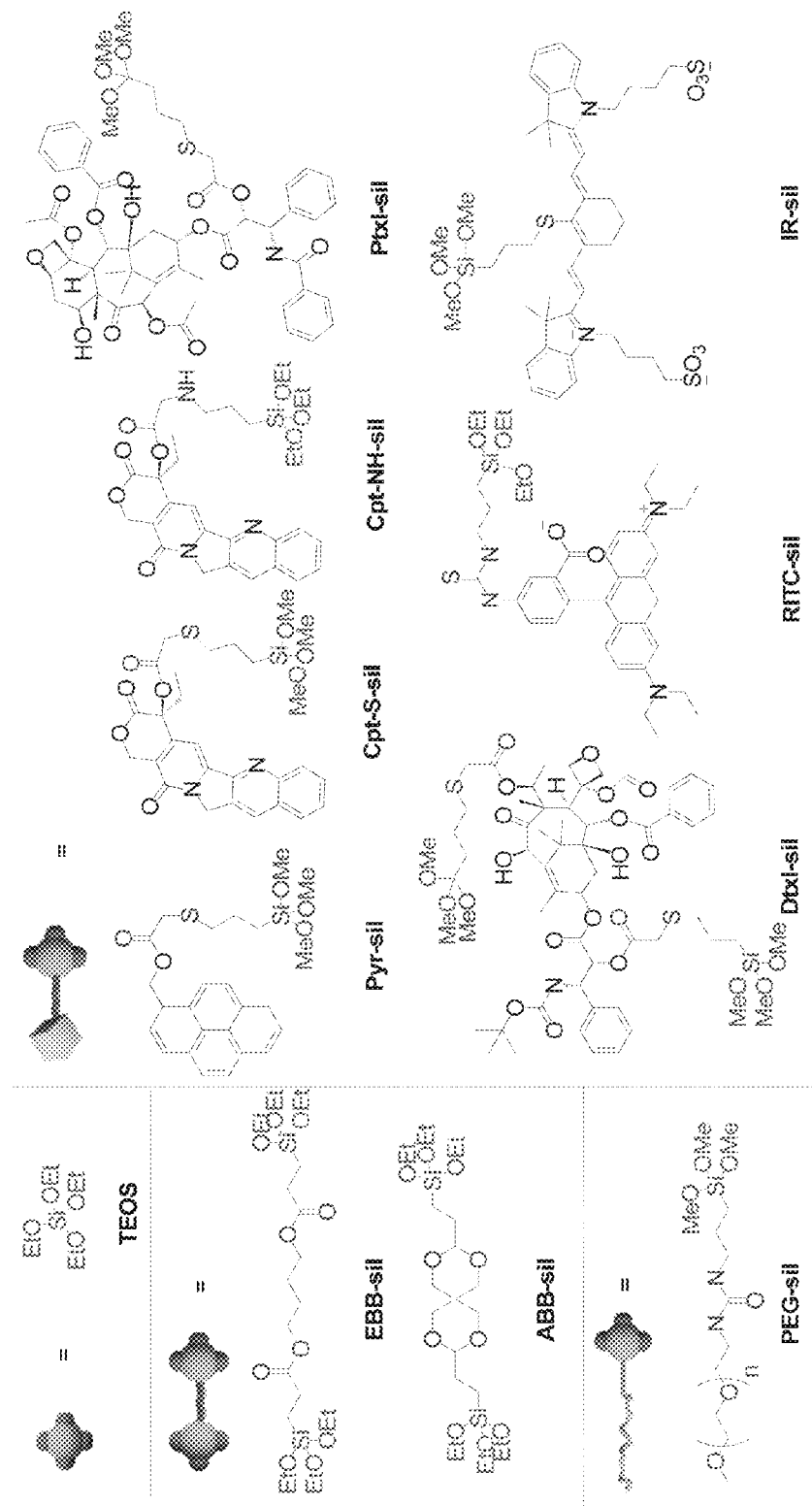

As illustrated in FIG. 1A, the size controlled silica NPs were first prepared (I) via the Stöber method from TEOS, optionally with degradable linker bridged silanes (EBB-sil and/or ABB-sil) followed by (II) the incorporation of a drug or dye using drug/dye containing silane coupling agents (one or more of Pyr-sil, Cpt-S-sil, Cpt-NH-sil, Ptxl-sil, Dtxl-sil, RITC-sil, and IR-sil) under mild conditions. Additionally, the NP surface can be modified, for example, using a polyethylene glycol (PEG) containing silane coupling agent mPEG-sil. EBB-sil, ABB-sil Pyr-sil, Cpt-S-sil, Cpt-NH-sil, Ptxl-sil, Dtxl-sil, RITC-sil, IR-sil, and mPEG-sil are illustrated in FIG. 1B.

Figure 2A:
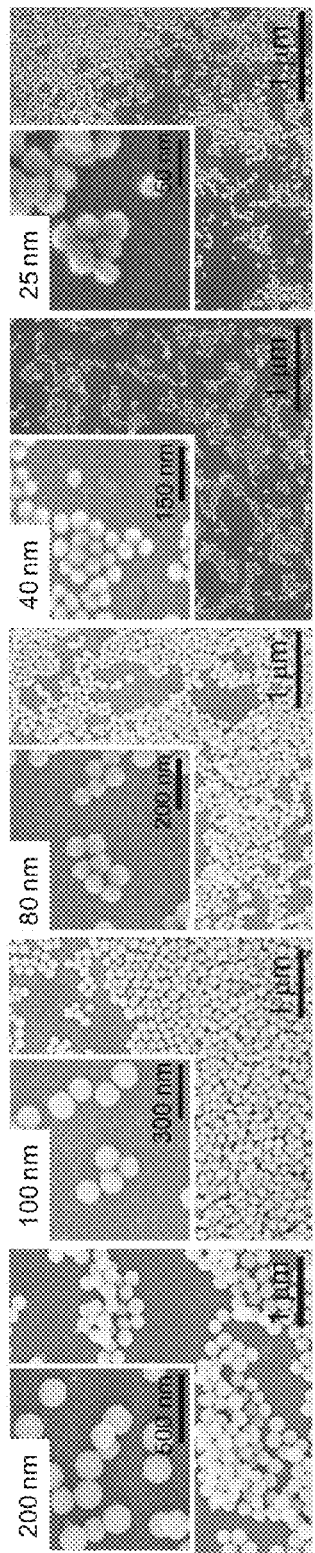
FIG. 2. (A) SEM images of Pyr-OH conjugated silica NPs with controlled sizes; (B) SEM images of CPT conjugated monodispersed silica NPs with controlled sizes.

To further demonstrate this concept, Pyr-sil containing pyrenemethanol (Pyr-OH) was used as a model drug. As expected, Pyr-sil was incorporated into silica NPs through formulation under several designed conditions via well-know Stöber method (Stober et al., *J. Colloid Interface Sci.* 26, 62-& (1968)), resulting in silica NPs with precisely controlled, highly monodisperse sizes (FIG. 2A; Table 1) ranging from about 25 to about 200 nm.

TABLE 1

Reaction conditions of size-controlled Pyr-NC via the Stöber method.

| Method | MeOH (mL) | DI water (μL) | NH$_4$OH (μL) | TEOS (μL) |
|---|---|---|---|---|
| St-A | 1.0 | 360 | 70 | 31.2 |
| St-B | 1.0 | 360 | 70 | 62.5 |
| St-C | 1.0 | 360 | 80 | 62.5 |
| St-D | 1.0 | 360 | 90 | 62.5 |
| St-E | 1.0 | 360 | 100 | 62.5 |
| St-F | 1.0 | 360 | 110 | 62.5 |
| St-G | 1.0 | 270 | 240 | 62.5 |
| St-H | 15.0 | 5400 | 1200 | 939 |

Particles with degradable linkers were prepared by a microemulsion method, the details of which are shown in Table 2.

TABLE 2

Reaction conditions of size-controlled silica NCs with degradable linkers via reverse microemulsion method.

| Method | Solvent | Triton x 100 (mg) | TEOS (μL) | EBB-sil (μL) | ABB-sil (μL) | degrad. domain (wt. %) |
|---|---|---|---|---|---|---|
| Trx-A | cyclohexane | 1.77 | 0 | 80 | 0 | 100% |
| Trx-B | decane | 1.77 | 0 | 80 | 0 | 100% |
| Trx-C | cyclohexane | 1.77 | 40 | 0 | 40 | 60.6% |

Pyr-OH was conjugated to silica NPs through an ester bond, therefore it can be hydrolyzed with controlled release kinetics under physiological condition. The narrow, monomodal particle size distributions of the drug conjugated silica NPs are in sharp contrast to the multimodal particle size distribution typically observed with polymeric nanomedicines (see Farokhzad et al., *Proc. Natl. Acad. Sci. U.S.A.* 103, 6315-6320 (2006); and Cheng et al., *Biomaterials* 28, 869-876 (2007)). The NPs described herein with well defined sizes are ideal candidates for investigating the size effect of drug delivery vehicles both in vitro and in vivo.

Figure 2B:
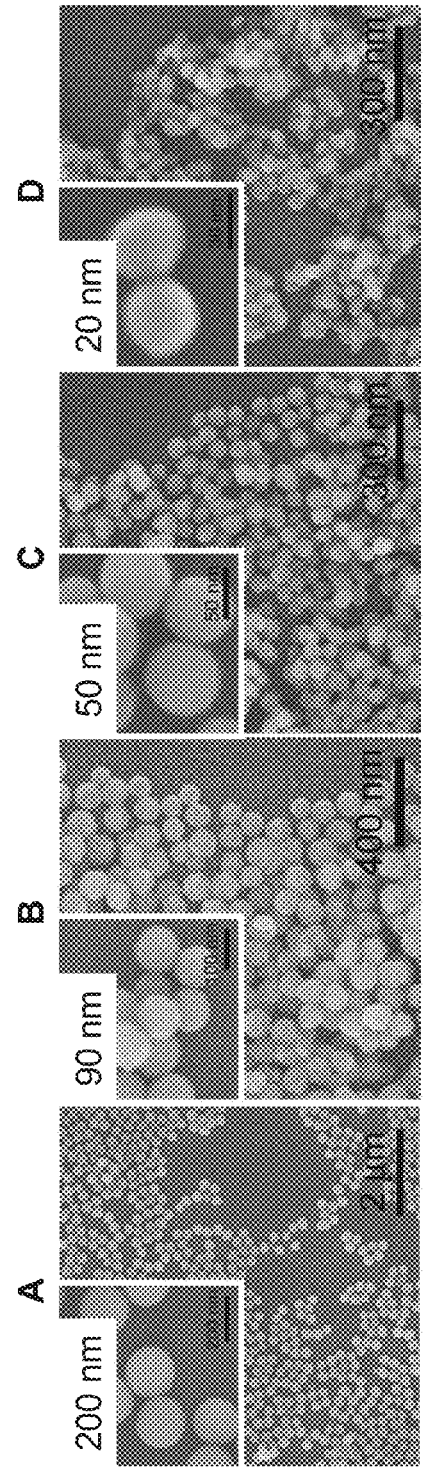

Camptothecin (Cpt), an anticancer drug, can be readily incorporated into silica NPs. Compound 3 (Cpt-sil) was prepared by conjugating a trimethoxysilane group to the 20-OH group of Cpt, thereby forming a hydrolysable ester bond. Cpt-sil was then incorporated into silica NPs using aforementioned method (FIG. 1A). As expected, Cpt containing silica NPs (Cpt-NPs) also had remarkably narrow size distribution as a result of the unique conditions and reagent ratios. Cpt-NPs with several discrete sizes were prepared by tuning the condensation conditions (FIG. 2B; Table 3). The size of the resulting Cpt conjugated silica NPs were 222.7±16.5, 96.1±8.8, 51.5±3.8 and 26.3±2.5 nm. The incorporation efficiencies were above 80% with drug loading as high as 16.9% wt. %, which loading is rarely reported for conventional conjugates.

TABLE 3

Preparation of drug-/dye-silica nanoconjugates[a].

| Entry | Name of NC | Drug/ Dye | Formulation[b] | Method[c] | D[d] (nm) | SD[e] (nm) | CV %[f] | I.E.[g] (%) | LD[h] (wt. %) |
|---|---|---|---|---|---|---|---|---|---|
| 1 | Pyr20 | Pyr | TEOS/Pyr-sil (29.4/1) | St-A | 26.6 | 2.7 | 10.2 | N/A | N/A |
| 2 | Pyr35 | Pyr | TEOS/Pyr-sil (29.4/1) | St-B | 36.3 | 2.9 | 8.0 | N/A | N/A |
| 3 | Pyr50 | Pyr | TEOS/Pyr-sil (29.4/1) | St-C | 43.4 | 3.9 | 9.0 | N/A | N/A |
| 4 | Pyr65 | Pyr | TEOS/Pyr-sil (29.4/1) | St-D | 64.1 | 3.1 | 4.8 | N/A | N/A |
| 5 | Pyr80 | Pyr | TEOS/Pyr-sil (29.4/1) | St-E | 84.4 | 7.6 | 9.0 | N/A | N/A |
| 6 | Pyr100 | Pyr | TEOS/Pyr-sil (29.4/1) | St-F | 104.4 | 8.8 | 8.4 | N/A | N/A |
| 7 | Pyr200 | Pyr | TEOS/Pyr-sil (29.4/1) | St-G | 195.3 | 12.8 | 6.6 | N/A | N/A |
| 8 | Cpt20 | Cpt | TEOS/Cpt-S-sil/ PEG-sil (2.2/1/0.14) | St-A | 26.3 | 2.5 | 9.5 | 81.2 | 24.0 |
| 9 | Cpt50 | Cpt | TEOS/Cpt-S-sil/ PEG-sil (2.2/1/0.14) | St-C | 51.5 | 3.8 | 7.4 | 82.9 | 24.0 |

TABLE 3-continued

Preparation of drug-/dye-silica nanoconjugates[a].

| Entry | Name of NC | Drug/Dye | Formulation[b] | Method[c] | D[d] (nm) | SD[e] (nm) | CV %[f] | I.E.[g] (%) | LD[h] (wt. %) |
|---|---|---|---|---|---|---|---|---|---|
| 10 | Cpt100 | Cpt | TEOS/Cpt-S-sil/PEG-sil (2.5/1/0.14) | St-F | 96.1 | 8.8 | 9.2 | 86.5 | 16.9 |
| 11 | Cpt200 | Cpt | TEOS/Cpt-S-sil/PEG-sil (2.2/1/0.14) | St-G | 222.7 | 16.5 | 7.4 | 80.7 | 24.0 |
| 12 | Cpt-N20 | Cpt | TEOS/Cpt-NH-sil/PEG-sil (3.8/1/0.20) | St-A | 25.9 | 2.4 | 9.3 | 79.3 | 15.9 |
| 13 | Cpt-N50 | Cpt | TEOS/Cpt-NH-sil/PEG-sil (3.8/1/0.20) | St-C | 56.2 | 5.2 | 9.3 | 83.2 | 16.6 |
| 14 | Cpt-N200 | Cpt | TEOS/Cpt-NH-sil/PEG-sil (3.8/1/0.20) | St-G | 197.3 | 15.9 | 8.1 | 81.0 | 16.2 |
| 15 | Ptxl50 | Ptxl | TEOS/Ptxl-sil/PEG-sil (8.1/1/0.40) | St-C | 51.8 | 4.9 | 9.5 | 80.7 | 13.4 |
| 16 | Dtxl50 | Dtxl | TEOS/Dtxl-sil/PEG-sil (8.1/1/0.40) | St-C | 106.9 | 10.0 | 9.4 | 73.1 | 15.4 |
| 17 | Dtxl100 | Dtxl | TEOS/Dtxl-sil/PEG-sil (8.1/1/0.40) | St-F | 55.0 | 5.2 | 9.5 | 67.4 | 14.3 |
| 18 | RITC20 | RITC | TEOS/RITC-sil/PEG-sil (58.8/1/3) | St-A | 23.7 | 2.3 | 9.7 | N/A | N/A |
| 19 | RITC50 | RITC | TEOS/RITC-sil/PEG-sil (58.8/1/3) | St-C | 49.2 | 4.9 | 10.0 | N/A | N/A |
| 20 | RITC200 | RITC | TEOS/RITC-sil/PEG-sil (58.8/1/3) | St-G | 188.9 | 14.4 | 7.6 | N/A | N/A |
| 21 | IR20 | IR783 | TEOS/IR783-sil/PEG-sil (58.8/1/3) | St-A | 26.5 | 2.6 | 9.8 | N/A | N/A |
| 22 | IR50 | IR783 | TEOS/IR783-sil/PEG-sil (58.8/1/3) | St-C | 47.8 | 4.7 | 9.8 | N/A | N/A |
| 23 | IR200 | IR783 | TEOS/IR783-sil/PEG-sil (58.8/1/3) | St-G | 206.9 | 16.2 | 7.8 | N/A | N/A |
| 24 | Cpt-EB20 | Cpt | EBB-sil/Cpt-S-sil/PEG-sil (6.1/1/0.3) | Trx-A | 23.5 | 2.3 | 9.8 | 87.5 | 13.8 |
| 25 | Cpt-EB50 | Cpt | EBB-sil/Cpt-S-sil/PEG-sil (6.0/1/0.3) | Trx-B | 45.5 | 4.2 | 9.2 | 93.3 | 14.6 |
| 26 | Cpt-AB20 | Cpt | TEOS/ABB-sil/Cpt-S-sil/PEG-sil (3.0/3.0/1/0.3) | Trx-C | 24.6 | 2.4 | 9.8 | 90.6 | 14.2 |
| 27 | Ptxl-EB20 | Ptxl | EBB-sil/Ptxl-sil/PEG-sil (9.0/1/0.40) | Trx-A | 22.7 | 2.2 | 9.7 | 77.4 | 8.8 |
| 28 | Cpt50*[i] | Cpt | TEOS/Cpt-S-sil/PEG-sil (88.2/1/9.0) | St-C | 46.2 | 4.6 | 10.0 | 84.8 | 1.0 |
| 29 | PLGA-PEG90[j] | N/A | PEG-PLGA | NPP | 91.8 | 36.0 | 39.2 | N/A | N/A |

[a]Methods and components used for formulations are described in FIG. 1;
[b]Components used for the silica NC formulation are presented in weight ratios;
[c]The volume ratio of MeOH/DI water/concentrated ammonia/TEOS were tuned in
St method to control the NC sizes: St-A, 32.0/11.5/2.24/1.00; St-B, 16.0/5.76/1.12/1.00; St-C, 16.0/5.76/1.28/1.00; St-D, 16.0/5.76/1.44/1.00; St-E, 16.0/5.76/1.60/1.00; St-F, 16.0/5.76/1.76/1.00; St-G, 16.0/4.32/3.84/1.00.
Cyclohexane was used as oil phased in Trx-A and -C; decane was used in Trx-B;
[d][e] The NC sizes were characterizes by SEM. Average diameter (D) and standard deviation (SD) were calculated by measuring 100 NCs in SEM images;
[f]CV % = SD/D;
[g]The incorporation efficiency (I.E.) was determined by monitoring and quantifying the concentration of free drugs in the supernatant using HPLC by centrifuging down the NPs;
[h]Real drug loading (LD) was calculated based on the feeding ratio of the drug to NC and I.E. value;
[i]gram scale preparation of Cpt50* with 0.939 mL TEOS;
[j]poly(lactide-co-glycolide)-b-methoxy-PEG (PLGA-PEG) nanoparticle prepared by nanoprecipitation (NPP) method is used as a negative control for comparing to the monodisperse silica NCs.

The NP sizes were characterizes by SEM. Average diameter and standard deviation (SD) were calculated by measuring 100 NPs in SEM images. The incorporation efficiency was determined by monitoring and quantifying the concentration of free drugs in the supernatant by HPLC after centrifuging down the NPs. Drug loadings was calculated based on the feeding ratio of drugs and incorporation efficiency (the actual percentage of drug added that is incorporated into the nanoparticles during the formulation process).

To incorporate Cpt efficiently without disrupting the drug structure, the Stöber method was modified to incorporate Cpt under milder conditions. For example, the following experimental procedure can be followed. The drug was incorporated at neutral pH with NaF. Silica NPs of various sizes were first prepared using the Stöber method described in Section 2.1 of Example 1 without adding Pyr-sil. Prepared NPs (4.1 mg) were redispersed in a mixture of 0.7 mL EtOH and 0.2 mL DI water followed by addition of 1.7 mg Cpt-sil in 100 μL DMSO solution. After the mixture was stirred for 10 minutes (to homogenization), 25 μL NaF solution in water (10 mg/mL) was added. The pH of this mixture was ~7. The supernatant of the mixture was monitored by HPLC to quantify the unreacted drugs in order to determine the incorporation efficiency of drugs to NPs. Drug loadings were calculated based on the feeding ratio of drugs and incorporation efficiency. It was assumed that TEOS was completely hydrolyzed. The NPs were collected by centrifugation at 13.2 k rpm and the supernatant was removed. The isolated NPs were washed by ethanol (1 mL) for three times and redispersed in DI water or 1×PBS buffer before use.

Using this modification, Cpt can be incorporated with high efficiency, as well as high drug loading. The resulting method provides a significant improvement compared to conventional mesoporous silica NPs in drug delivery applications. For example, mesoporous silica NPs only allows incorporation of drugs by less controllable means, such as simple absorption, typically leading to low incorporation efficiency and uncontrollable release profile of payload (Vallet-Regi et al., *Angew. Chem.*, Int. Ed. 46, 7548-7558 (2007)). The inventive particles described herein are not mesoporous silica particles.

Figure 3:
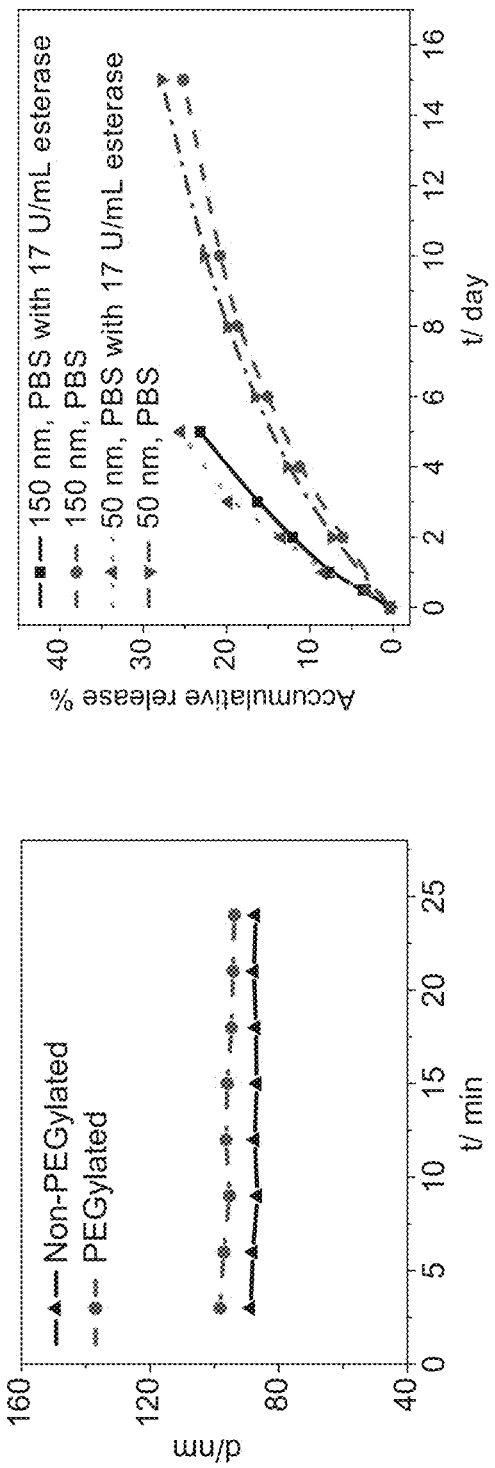
FIG. 3. Stability of PEGylated and non-PEGylated silica NPs in PBS (1×) (left graph); release kinetics of 50 nm and 150 nm Cpt conjugated silica NPs in PBS (1×) or PBS (1×) with 17 U/mL esterase at 37° C. (right graph).

Good control over the drug incorporation by the methods described herein for drug conjugated silica NPs can be attributed to the successful strategy of using Drug-sil as a building block for co-condensing into silica NPs, leading to covalent conjugation of drug to silica NPs. Because of the ease and excellent control over the formulation, the preparation of these drug conjugated silica NPs can be easily scaled up to provide gram-quantities. This scalable unit operation, amenable to manufacturing large quantities, is important for the development of drug delivery vehicles for clinical translation (Farokhzad et al., *ACS Nano* 3, 16-20 (2009)). Particle stability in physiological condition is also a prerequisite for effective drug delivery in vivo. Silica NPs displayed remarkable stability in PBS (1×), and NP size remained essentially non-changed for 25 minutes (FIG. 3, left graph).

To prolong systemic circulation and reduced aggregation of NPs in blood, the surface of the NPs was modified by 1-(2-(2-methoxyethoxy)ethyl)-3-(3-(trimethoxysilyl)propyl)urea (mPEG$_{5k}$-sil) (11) to obtain NPs with surface modified by PEG (denoted as PEGylated; FIG. 1A). The surface modification of silica NPs was easily achieved using a PEG containing silane coupling agent, such as mPEG$_{5k}$-sil. A variety of other surface properties (for example, positively or negatively charged surfaces) can also be obtained because a large number of silane coupling agents are immediately available. For example, modification with (3-aminopropyl)trimethoxysilane (Aldrich) or [3-(2-aminoethylamino)propyl] tri-methoxysilane can be carried out to provide for a positively charged surface (Aldrich). Reagents such as carboxyethylsilanetriol sodium salt (Gelest) can be used to prepare particles having a negatively charged surface. For PEGylated surface such as those described herein, one may use reagents such as mPEG-silane (Laysan Bio, Inc.). The ease of surface modification is another advantage of the drug conjugated silica NPs described herein (see Bagwe et al., *Langmuir* 22, 4357-4362 (2006)).

Figure 4:
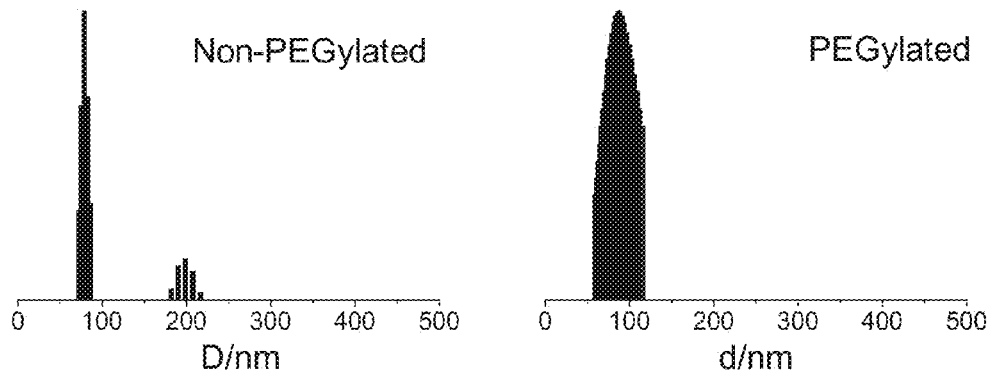
FIG. 4. Size distribution of PEGylated and non-PEGylated silica NPs in PBS (1×) for 4 hours at room temperature, measured by DLS.

PEGylated silica NPs have slightly larger hydrodynamic diameters than the non-PEGylated counterparts, while a smaller PDI of size distribution indicates enhanced stability in PBS (1×) because PEGylation imparts steric stability to silica NPs in salt solutions. When exposed to PBS (1×) for 4 hours, non-PEGylated silica NPs started to aggregate (FIG. 4, left graph), while PEGylated silica NPs remained a single distribution of sizes (FIG. 4, right graph), as determined by dynamic light scattering (DLS) measurements.

Drug burst release is a long-standing formulation challenge of nanocarriers with drug simply encapsulated or adsorbed (for example, mesoporous silica NPs), which causes undesirable side-effect and reduced therapeutic efficacy (Soppimath et al., *J. Controlled Release* 70, 1-20 (2001)). Conventional nanoencapsulates typically "burst" and release 60-90% of their payloads within a few to tens of hours because the release of drug is controlled solely by diffusion (Musumeci et al., *Int. J. Pharm.* 325, 172-179 (2006)). Because the drug release kinetics of drug conjugated silica NPs are determined not only by diffusion, but also by the hydrolysis of the ester bond linker, the release kinetics of drug from silica NPs are more controllable with no or significantly reduced burst release effect (FIG. 3, right graph). The release kinetics of Cpt-NP in PBS (1×) or PBS (1×) with 17 U/mL esterase at 37° C. were measured using HPLC. Cpt released from the Cpt-NP (50 nm) in PBS (1×) were 7.4% at Day 2 and 22.7% at Day 10, respectively, with no burst effect.

In the presence of esterases, which are abundant in cytoplasm, hydrolization was accelerated and Cpt was released faster. The release of Cpt of 50 nm Cpt-NPs was slightly faster than that of 150 nm Cpt-NPs, both in PBS (1×) and PBS (1×) with 17 U/mL esterase, presumably due to the larger surface area of smaller NPs, which have more drug molecules exposed. The surface-to-volume ratio of a given mass of 50 nm NPs is theoretically three fold of that of 150 nm NP. Moreover, because of the slow release, Cpt-NPs exhibit substantially lowered toxicity than free Cpt in LNCaP cells (Table 4).

TABLE 4

IC$_{50}$ values of 20 nm, 50 nm and 200 nm Cpt conjugated silica NPs to LNCaP prostate adenocarcinoma cells determined by MTT assay.

| Agent | IC50 (nM) |
|---|---|
| CPT | 7 |
| CPT-NP, 20 nm | 220 |
| CPT-NP, 50 nm | 510 |
| CPT-NP, 200 nm | 800 |
| NP, 50 nm | >10$^6$ |

With the precisely size controlled NP system, the NP size effect in cellular internalization was probed using silica NPs with different sizes. Silica NPs were covalently labeled using rhodamine B isothiocyanate (FIG. 1, using RITC-sil). Three different size NPs: 20 nm, 50 nm and 200 nm in diameter, were used to investigate the internalization behavior of HeLa cells at 37° C. for 1 hour of incubation. As shown in confocal laser scanning microscopy images (FIG. 5), the smallest NPs (20 nm) were taken up to a greater by HeLa, as indicated by the strong signal of red fluorescence, while the largest NPs (200 nm) were internalized much less, with a majority of NPs staying at the surface of cells. The kinetics of NP internalization was evaluated by using a flow cytometry method.

Figure 6:
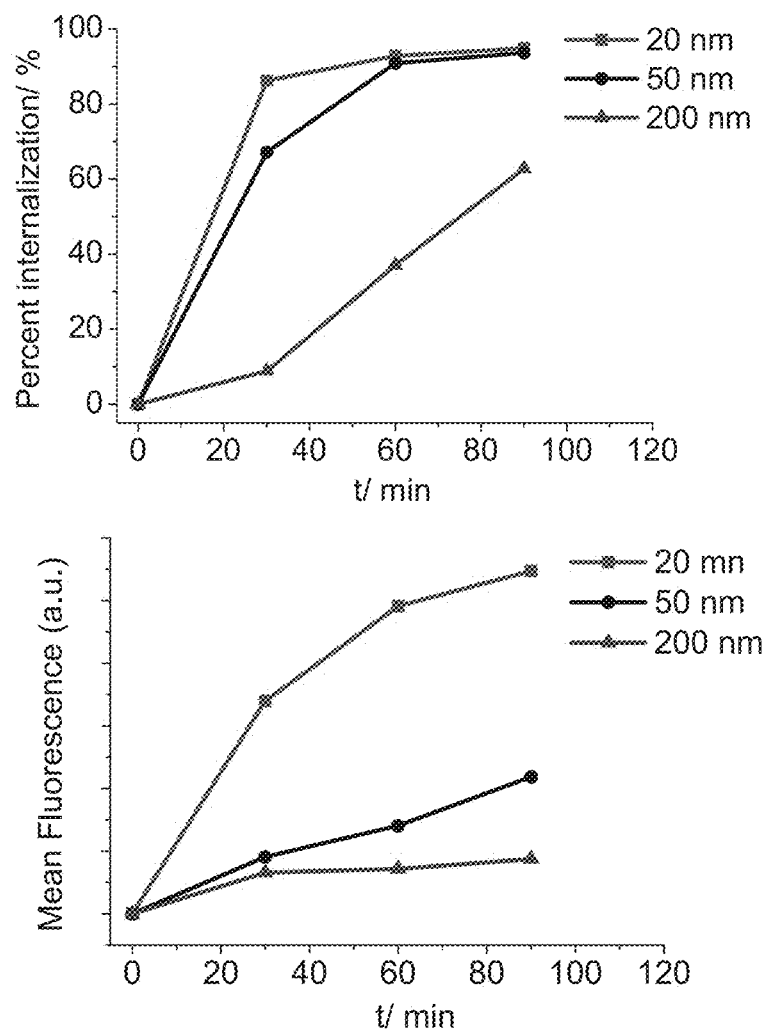
FIG. 6. Internalization profile of rhodamine labeled silica NPs with HeLa cells over 90 min incubation at 37° C. evaluated by percent internalization (top) or mean fluorescence (bottom).

The time schedule of NP uptake was studied from 30 minutes to 90 minutes (FIG. 6). The kinetics of NP internalization exhibited a strong dependence on NP size. A very small percentage (8.85%) of cell population was observed to internalize 200 nm NPs at 30 minutes, while percentages as high as 67.11% and 86.25% were observed for 50 nm and 20 nm NPs, respectively. Both groups treated with 50 nm and 200 nm NPs were nearly saturated after 60 minutes in terms of percentage of internalized cell population. However, cells treated with 50 nm NPs exhibited lower mean fluorescence comparing to cells treated with 20 nm NPs (FIG. 6, bottom). Cells treated with 200 nm NPs internalized only 62.7% of the NPs after 90 minutes incubation, and cells treated with 200 nm NP showed much lower mean fluorescence compared to both 50 nm and 20 nm NPs. Thus, in the range of 20-200 nm NP size, smaller NPs are internalized to a greater degree and faster by HeLa cells. These data clearly illustrate the size dependent endocytotic mechanism of cell entry.

The overall cytotoxicity of Cpt-NP was evaluated and compared with Cpt as a free drug using MTT assays with LNCaP prostate adenocarcinoma cells. The IC$_{50}$ values of Cpt-NP with different sizes, 20 nm, 50 nm, and 200 nm in diameter, are 220, 510 and 800 nM, respectively (Table 4). The in vitro toxicities of Cpt-NP are correlated to the amount of Cpt released and the internalization of NPs by cells. Smaller NPs showed higher toxicity to the cancer cells with lower $IC_{50}$ values. In conjunction with the above release kinetics data and cell internalization behaviors of different size NPs, the higher toxicity can be attributed to the faster release of active Cpt and more rapid internalization by cells for smaller NPs.

Various in vitro and in vivo studies showed that silica NPs can be safely used as drug carriers. Recent studies have shown that silica NPs can decompose in blood within a few days (Finnie et al., *J. Sol-Gel Sci. Technol.* 49, 12-18 (2009)), indicating that this class of NPs can be cleared via the renal system. The in vitro study (MTT assay; Table 4) showed almost no toxicity of blank silica NPs ($IC_{50}$>1 mM). Acute in vivo toxicity experiments were then carried out after i.v. administration of 50 nm and 200 nm silica NPs in C57BL/6 mice at very high doses, up to 250 mg/kg.

There was no mortality or deterioration under general conditions observed in any of the test groups. There were also no treatment related clinical signs and change of body weights. Representative sections of various organs taken 24 hours after injections from control mice receiving PBS and mice receiving silica NPs were stained by hematoxylin and eosin and were evaluated by an independent pathologist. Histopathology of mouse tissues following an intravenous injection of silica nanoparticles via a tail vein was closely examined. Representative sections of various organs taken from control mice receiving PBS and mice receiving 250 mg/kg 50 nm or 200 nm blank silica nanoparticles 24 hour post injection were analyzed. Hematoxylin and eosin stains were used in the analysis. No organs of a mouse given silica nanoparticles showed any acute inflammations. The absence of immune or inflammatory reactions after NP administration supports the conclusion that silica NPs themselves are generally safe. The non-toxicity of the silica NPs led to the investigation of NP properties as a drug delivery platform in vivo.

The distribution of many anticancer drugs in tumor tissues is incomplete due to the large distance between blood vessels in solid tumors, the composition of the extracellular matrix, cell-cell adhesion, high interstitial fluid pressure and lack of convection. The poor penetration of anticancer drugs into tumors can be an important factor limiting their efficacy.

The inefficient penetration also limits the efficacy of many chemotherapeutic treatments. Penetration of NPs into the core of a spheroid, which serves as a tumor model, is limited to particles smaller than 100 nm NP (Goodman et al., *Int. J. Nanomedicine* 2, 265-274 (2007)). Recently, Chan and coworkers reported that 20 nm and 60 nm gold NPs, model drug delivery systems, permeate tumor tissues much more rapid than 100 nm particles in vivo (*Nano Lett.* 9, 1909-1915 (2009)). Therefore the drug conjugated silica NPs system described herein, carrying therapeutic agents with well controlled sizes down to nearly 20 nm in diameter, is an important addition to the art for enhancing solid tumor penetration, thereby allowing for the improvement of a given therapeutic index.

To investigate the impact of the size of silica NPs on tumor penetration, C57BL/6 mice bearing Lewis lung carcinoma (LLC) tumors were sacrificed to harvest the tumors when tumor sizes reached approximately 8.0 mm×10.0 mm Tumors were ex vivo cultured for 48 hours with silica NPs 20 nm, 50 nm and 200 nm in diameter with IR783 labeling. Tumor sections 20 μm in thickness were collected and fluorescence images were taken using a Zeiss Axiovert fluorescence microscope with 780 nm laser excitation with fixed exposure time (FIGS. 7a and 7b). Generally, 20 nm silica NPs penetrated deepest into solid tumor showing much more fluorescence from tumor section edge to centre, while 50 nm NPs distributed less deeply. However, 200 nm NPs stayed almost exclusively on the surface of the tumors. To directly compare the penetration depth of these three different size NPs, a plot profile of fluorescence intensity versus distance from tumor edge (left edge on FIG. 7a) to centre were generated by Image J (FIG. 7c). The penetration depth was defined as the depth at which the fluorescence intensity drops to <5% of the maximum intensity at the edge of tumors. Twenty nm NPs were able to penetrate tumor tissue as deep as 1396 μm, 50 nm NPs penetrated up to 660 μm, and 200 nm NPs penetrated to a maximum of only 88 μm. There was a general trend of decreased permeation as particle size increased. Twenty nm NP can penetrate tumors more effectively because of their more efficient diffusion into tumor interstitial spaces and better vascular permeation.

Figure 7:
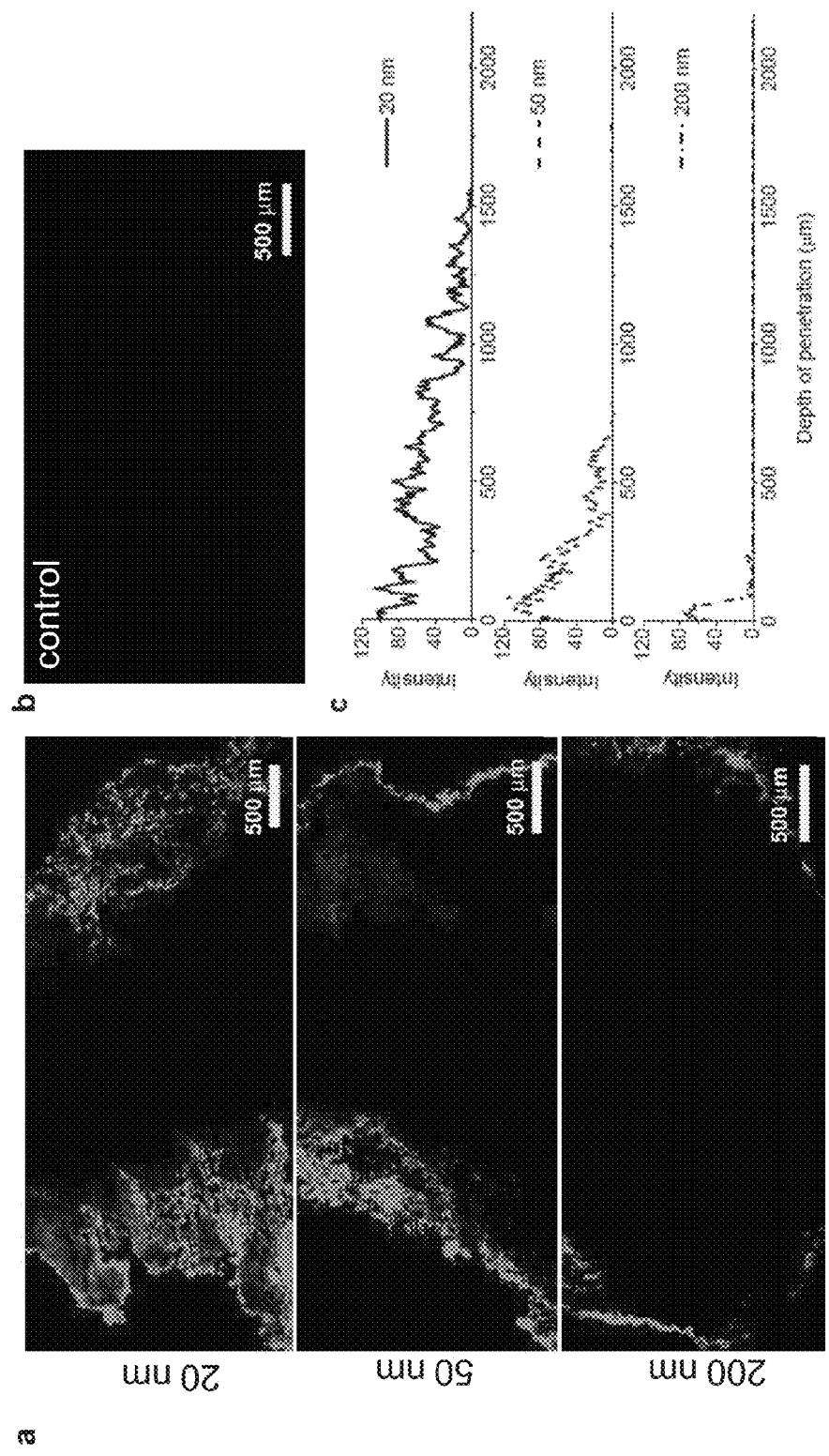
FIG. 7. Size effect on tumor penetration. Lewis lung carcinoma tumors (size: ~8.0 mm×10.0 mm) was ex vivo cultured with silica NPs, 20 nm, 50 nm or 200 nm in diameter with IR783 labeling in cell medium for 48 hours (a). Tumor without any treatment served as the control (b). Tumor sections (intersections, 20 μm in thick) were collected by cryostat and mounted on glass slides. Fluorescence images were taken by fluorescence microscope with 780 nm laser excitation. A tiling image was taken with fixed exposure time to show the NP penetration in tumor sections. Plot profile of fluorescence in tumor section showing the depth of NP penetration (c) was analyzed by Image J.
Figure 15:
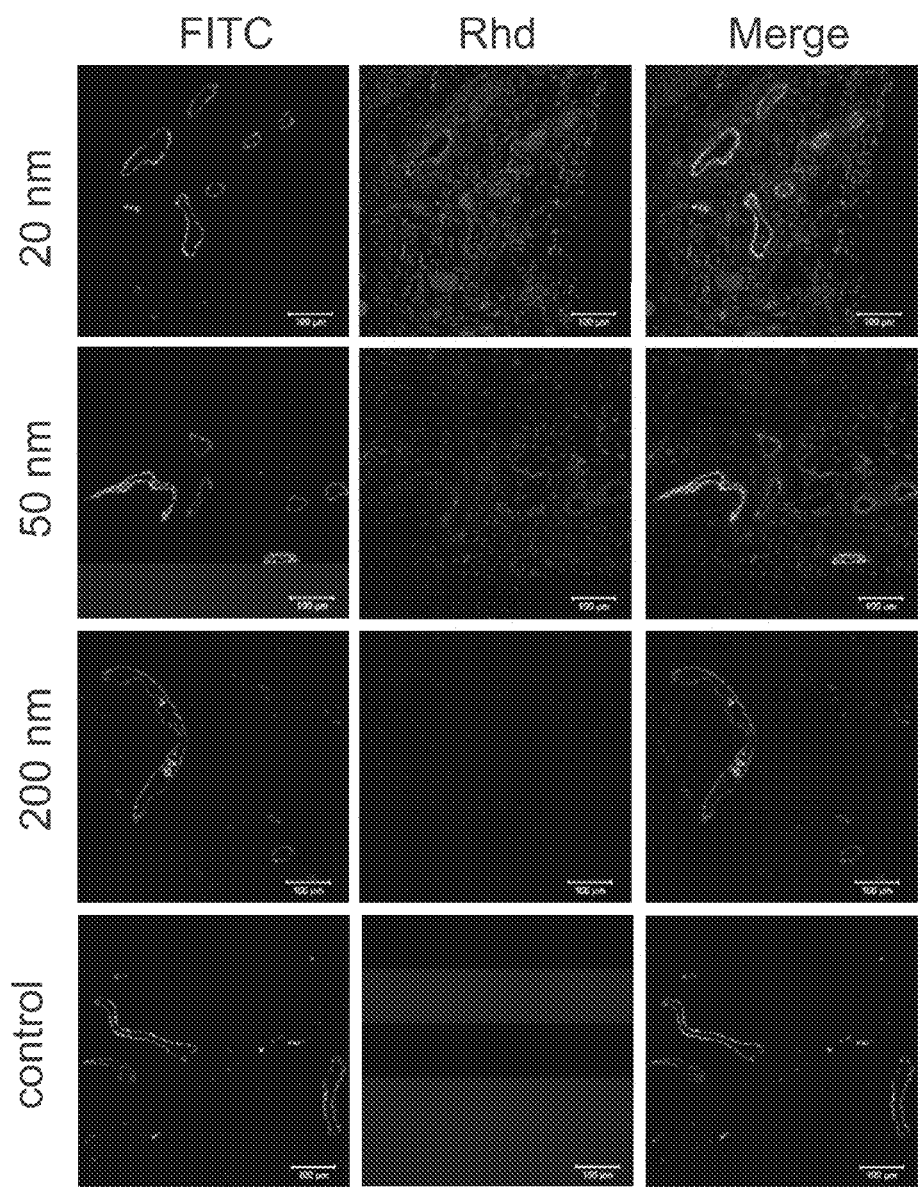
FIG. 15. Size effect on tumor penetration in relation to blood vessels via an in vivo study. C57Bl/6 mice bearing Lewis lung carcinoma (LLC) tumors (size: ~5.0 mm×6.0 mm) were injected intravenously with Rhodamine-labeled silica NPs 20, 50, or 200 nm in diameter at a dose of 500 mg/kg. Mice were euthanized and dissected 24 hours post injection. Tumor sections (intersections, 5 μm in thick) were collected in paraffin and mounted on glass slides. Fluorescence images were taken by Zeiss LSM 700 confocal microscope. Representative two-color composite images showing the perivascular distribution of rhodamine labeled silica NP (red, Rhd channel) in relation to blood vessels (green, FITC channel) in tissue sections from LLC tumors.

In vivo studies were also carried out to investigate the size effect on tumor penetration in relation to blood vessels. C57Bl/6 mice bearing LLC tumors (size: ~5.0 mm×6.0 mm) were injected intravenously with Rhodamine-labeled silica NPs 20, 50, or 200 nm in diameter at a dose of 500 mg/kg. Mice were euthanized and dissected 24 hours post-injection. Tumor sections (intersections, 5 μm in thick) were collected in paraffin and mounted on glass slides. Fluorescence images were taken by a Zeiss LSM 700 confocal microscope. Representative two-color composite images showing the perivascular distribution of rhodamine labeled silica NP (red, Rhd channel, FIG. 15) in relation to blood vessels (green, FITC channel) in tissue sections from LLC tumors. From the images that merge the two channels, the penetration behaviors of different size NPs from blood vessels into the tumor tissues can be clearly observed. Twenty nm diameter NPs can suitably penetrate both vasculature and tumor tissues with a strong red fluorescence signal not only around the blood vessel area but also deep in the interstitial area of tumor tissues. Fifty nm diameter NPs showed lower permeability compared to the 20 nm NPs, while red fluorescence was barely seen for the 200 nm NPs in the merged images. Smaller NPs have higher permeability due to their higher level of tumor accumulation and easier passive diffusion evidenced by the ex vivo tumor penetration study (FIG. 7).

Dreher et al. made use of fluorescently labeled dextrans to demonstrate that vascular permeability and tumor permeation decrease as macromolecule weight increase (3.3 kDa to 2 MDa) (*J. Natl. Cancer Inst.* 98, 335-344 (2006)). Although very low molecular weight dextran (3.3-10 kDa) had rapid rates of interstitial space permeation, it was too small to passively accumulate in a tumor because of its fast migration in tumor tissues. Very small NPs, for example smaller than 5 nm, may behave similar to the low molecular dextran. Data from analysis of the 20 nm NPs described herein indicate they may be close to the optimum size for drug delivery vehicle in terms of tumor penetration and accumulation for cancer treatment.

Size effects were also investigated with respect to tumor accumulation. IR783 labeled silica NPs, 50 nm and 200 nm in diameter, were i.v. administered to Balb/c nude mice bearing LNCaP tumors (approximately 12 mm×12 mm in size) at a dose of 150 mg/kg NPs containing same amount of IR783 dye. The total injection per mouse in terms of fluorescence intensity was measured by diluting IR783 labeled silica NP solutions (Table 5).

TABLE 5

Total injection of fluorescence intensity of IR783-labeled silica NPs for each mouse.

| NP | Total injection of Fluorescence (a.u.) |
|---|---|
| 50 nm | 62592 |
| 200 nm | 44160 |

Figure 8:
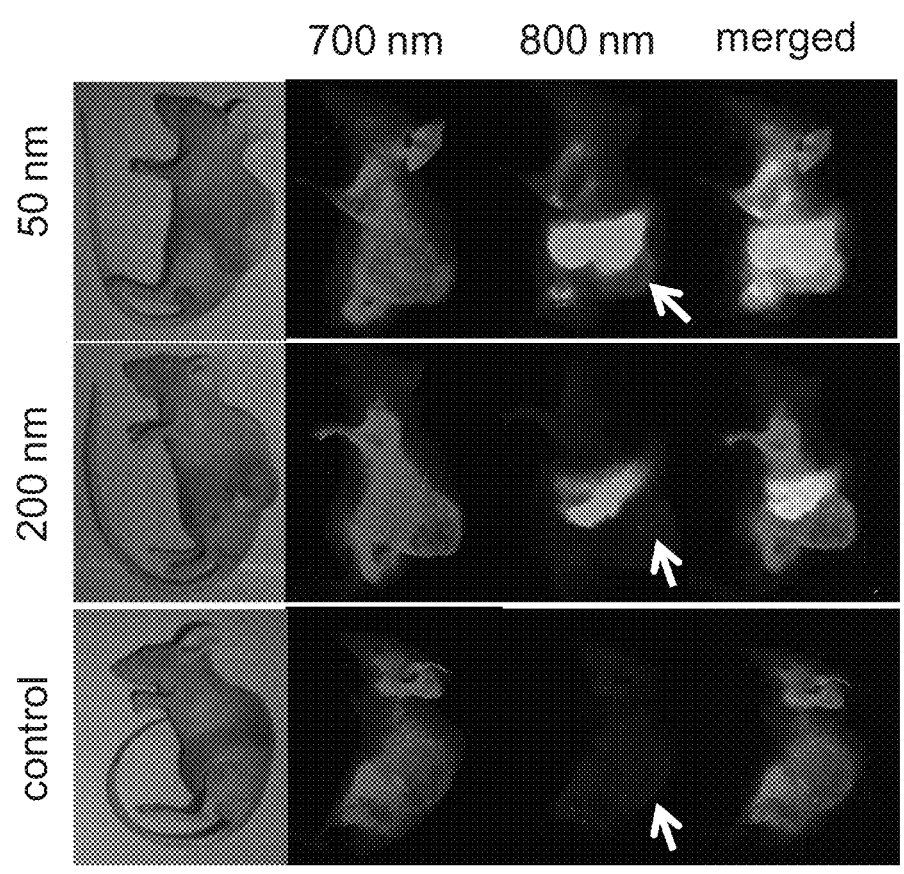
FIG. 8. Size effect on biodistribution. Balb/c nude mice bearing LNCaP tumors (size: ~12 mm×12 mm) were injected intravenously with IR783-labeled silica NPs 50 or 200 nm in diameter at a dose of 150 mg/kg. Mice were euthanized 24 hours post injection, fixed in 10% formalin. Whole body images were taken by an Odyssey infrared mouse imaging system at both 700 nm channel (autofluorescence of mouse body) and 800 nm channel (IR783). Arrows indicate the positions of tumors.
Figure 9:
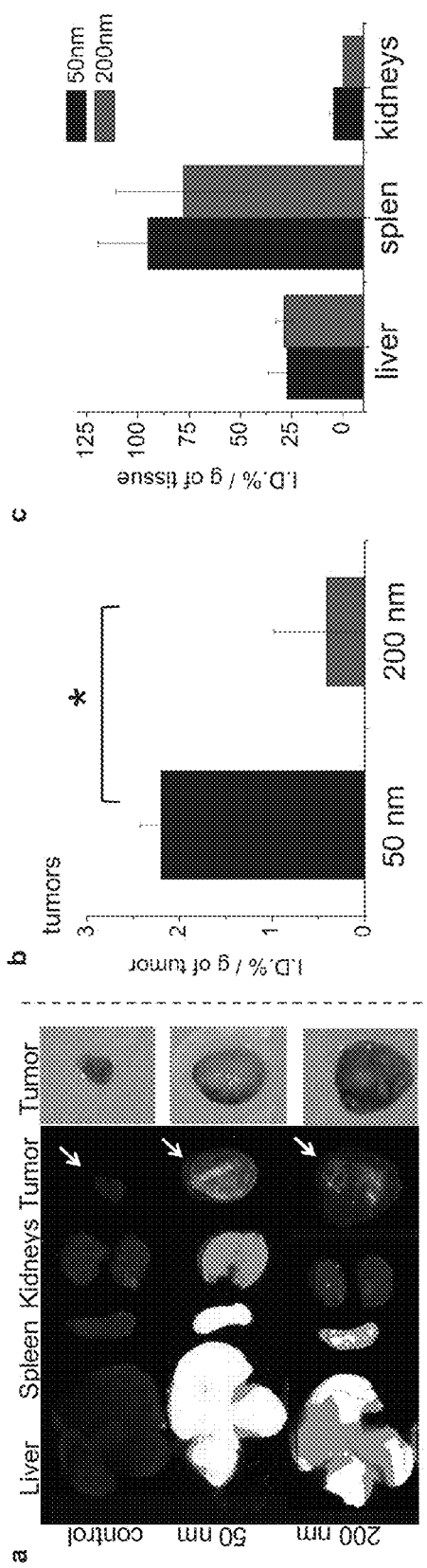
FIG. 9. (a) Balb/c nude mice bearing LNCaP tumors (size: ~12 mm×12 mm) were injected intravenously with IR783-labeled silica NPs 50 or 200 nm in diameter at a dose of 150 mg/kg. Mice were euthanized and dissected 24 hours post injection. The fluorescence images of each organ was taken ex vivo using an Odyssey infrared mouse imaging system. Tumors (b) and other organs (c) were harvested and fluorescence at 800 nm was measured ex vivo to evaluate the tumor accumulation of silica NPs (average±SD; n=2; *p<0.05).

Whole body images were taken by an Odyssey infrared imaging system 24 hours post injection at both 700 nm channel (showing autofluorescence of mouse body) and 800 nm channel (IR783) with fixed exposure time. The total fluorescence intensity of IR783-labeled silica NPs for each mouse was 62,592 (a.u.) for 50 nm NPs and 44,160 (a.u.) for 200 nm NPs. FIG. 8 shows that clear tumor accumulation was observed for 50 nm NPs, while nearly negligible amount of fluorescence was observed for 200 nm NP at the tumor area. Arrows indicate the positions of tumors. All tumors, as well as livers, spleens and kidneys were harvested after the mice were euthanized and were measured for fluorescence intensity at 800 nm ex vivo (FIG. 9). All organ measurements were carried out on tissue of no than 3 mm thick, with >80% transmission (Table 6).

TABLE 6

Percent transmission of various mouse tissues.

| Tissue | Thickness (mm) | Transmission (%) |
|---|---|---|
| spleen | 1.5 | 96.3 |
| kidneys | 2.5 | 100.0 |
| lung | 2 | 100.0 |
| heart | 3 | 64.4 |
|  | 2 | 100.0 |
| liver | 4 | 80.0 |
|  | 6 | 23.6 |
|  | 2 | 100.7 |
| tumor | 4 | 75.0 |
|  | 6 | 11.2 |

Data is presented as percent injected dose per gram of tissues. The statistical analysis was undertaken using a Student's t-test. P-values<0.05 were considered statistically significant. Data reported are average±standard deviation.

Figure 5:
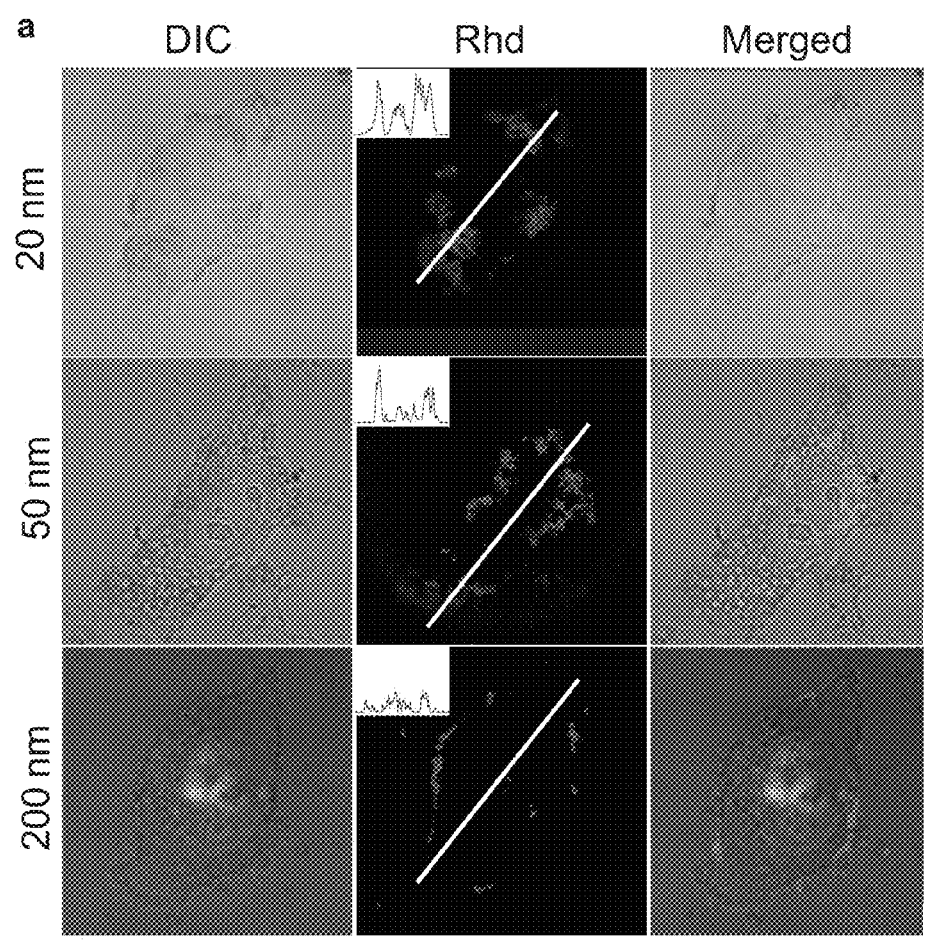
FIG. 5. Size effect on cell internalization. Confocal laser scanning microscopy images of HeLa cells after 1 hour incubation at 37° C. with 20 nm, 50 nm and 200 nm silica NPs with rhodamine labeling. Left column: differential interference contrast (DIC), middle column: rhodamine channel (Rhd), right column: merged.
Figure 10:
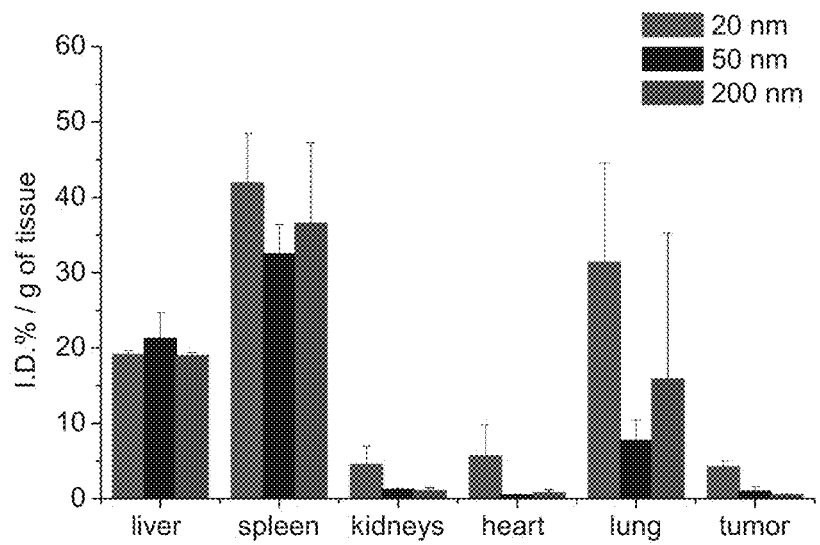
FIG. 10. C57Bl/6 mice bearing LLC tumors (size: ~5 mm×6 mm) were injected intravenously with IR783-labeled silica NPs 20 (left bar), 50 (middle bar), or 200 (right bar) nm in diameter at a dose of 500 mg/kg. Mice were euthanized and dissected 24 hours post injection. Various organs were fixed in 10% formalin. The fluorescence of each organ was measure ex vivo at 800 nm using an Odyssey infrared mouse imaging system (average±SD; n=3).

The values of % injected dose/g of tumors at 24 hours for the 50 nm and 200 nm NP group were 2.2±0.2 and 0.4±0.5 (average±SD; n=2) respectively. The accumulation of 50 nm NPs in tumors was 5.5 fold higher (n=2; *p<0.05) with statistical significance. The ability of 50 nm NPs maintain a significantly higher concentration in the tumor at 24 hours can be attributed to an enhanced permeation and retention (EPR) effect, better tumor penetration as demonstrated in FIG. 7, and increased cancer cell internalization as shown in FIGS. 5 and 6. As noted previously, 200 nm NPs or larger NPs have poor tumor accumulation because of less tumor penetration and cell uptake. Biodistribution patterns of the liver, spleen and kidneys are not significantly different for the two groups (FIG. 9c). Size effect of biodistribution was also evaluated in C57Bl/6 mice bearing LLC tumors (FIG. 10). Accumulation of 20 nm NPs in tumor was 3.2 fold higher than 50 nm NPs, and 7.0 fold higher than 200 nm NPs.

Figure 11:
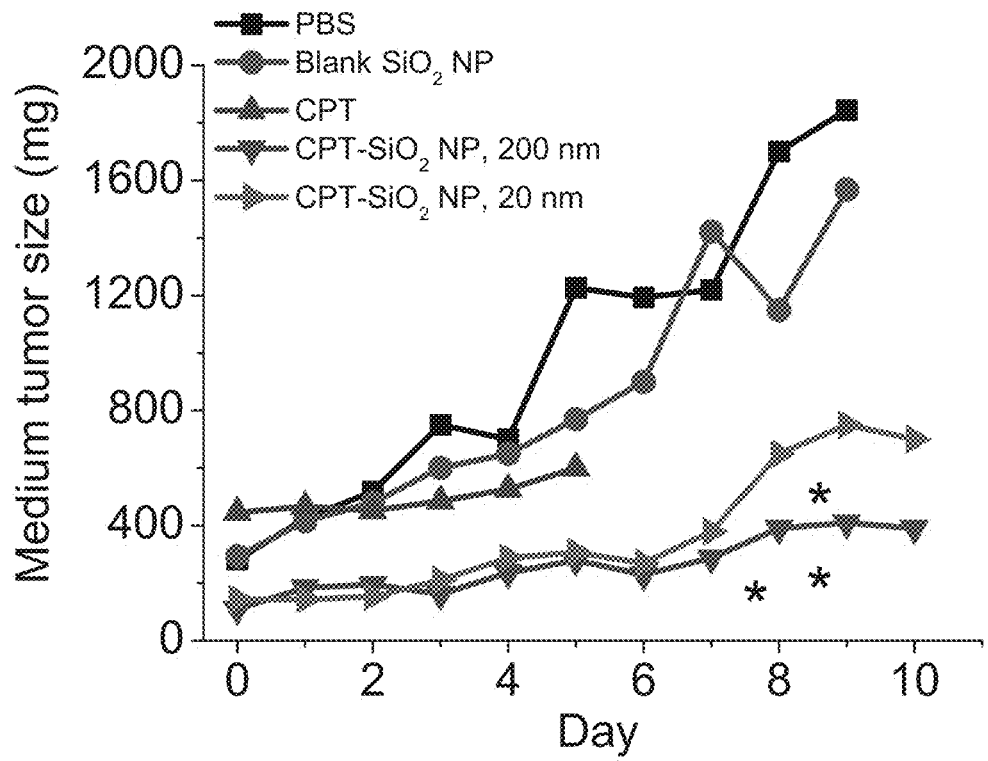
FIG. 11. In vivo antitumor efficacy studies. Delay and inhibition of LLC tumor growth for C57Bl/6 mice with treatment of CPT conjugated silica NPs in different sizes. Both CPT-NPs 20 nm and 200 nm delayed tumor growth at Day 6 and 7 (*p<0.05 vs. control group (PBS)).

The efficacy of the drug conjugated silica NPs was next evaluated using xenograft models of LLC tumor developed by s.c. injection of LLC cells in the flank of C57BL/6 mice. After tumors has developed to ~300 mm³, comparative efficacy studies were performed by dividing animals into five groups (n=5) in a way to minimize weight and tumor size differences among the groups. Using Cpt as a reference point, the following regimens were administered by a single i.v. injection: a, PBS; b, PEGylated blank silica NPs; c, emulsified Cpt, 30 mg/kg; d, Cpt-NP, 200 nm, 25 mg/kg; e, Cpt-NP, 20 nm, 25 mg/kg. Tumor size and body weight were then monitored for 10 days. The results show that a single i.v. administration of 200 nm or 20 nm Cpt-NPs is significantly more efficacious than free Cpt (FIG. 11). Both Cpt-NPs 20 nm and 200 nm in diameter delayed tumor growth at Day 7 and 6, respectively, with statistical significance comparing with control group receiving PBS (p<0.05 by t-test). None of the animals of the PBS or blank silica NP group exhibited tumor regression. All animals in free Cpt group reached end point with >20% body weight loss at about day 5.

Formulation of clinically applicable, mono-disperse nanoparticles with controlled sizes for drug delivery is a formidable task. Described herein are drug conjugated silica NPs formulated with excellent size control, well controlled surface chemistry, as well as high drug loading, high loading efficiencies, controlled release profiles and synthetic scalability and universality. Improved tumor penetration by 20 nm drug conjugated silica NPs compared to larger particles was demonstrated. This disclosure opens a new direction for size controlled nanomedicines for improved cancer treatments.

Degradable Nanoparticles.

Degradable silica-drug conjugated nanoparticles (NPs) with controlled sizes can be prepared by co-condensation of two silane precursors. In some embodiments, one silane precursor can be a drug-containing trialkoxysilane (drug-Si), and the second silane precursor can be, for example, tetraethyl orthosilicate (TEOS) and/or a degradable organo-group bridged trialkoxysilane (Si-bridge-Si). The drug can be conjugated to the trialkoxysilane through a responsively degradable linker. The surface of this silica nanoparticle (NP) can be modified by using a function group-containing trialkoxysilane, such as a PEG group linked to a trialkoxysilane.

Figure 12:
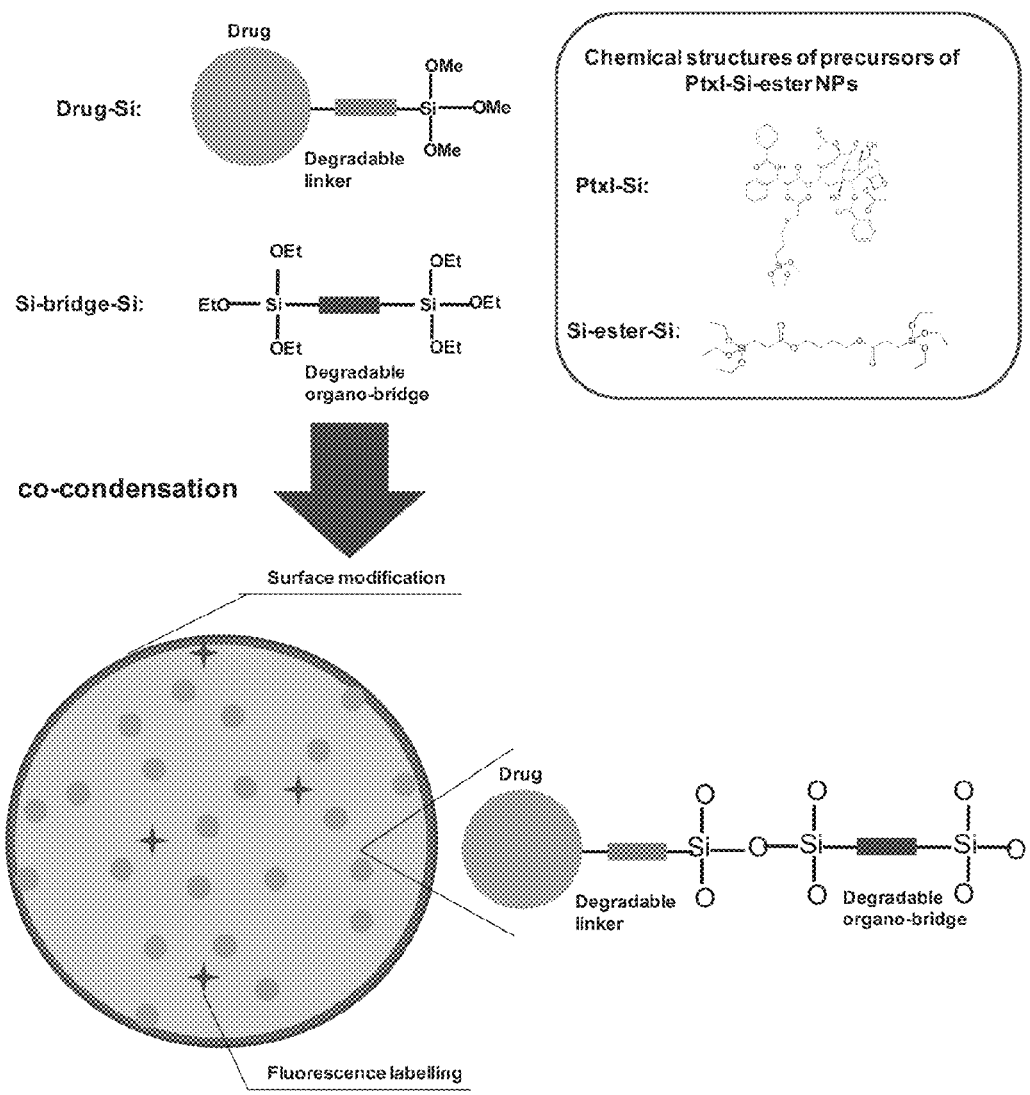
FIG. 12. Degradable silica-drug conjugated nanoparticles and their preparation, according to one embodiment. Examples of Ptxl-Si-ester (Ptxl-Si) and degradable linkers (Si-ester-Si) nanoparticle precursors are shown, according to various embodiments.

Fluorescence labeling of the NPs can be achieved by co-condensation of a fluorescent dye-containing trialkoxysilane. One schematic structure of a silica NPs is illustrated in FIG. 12, which shows the preparation of a Ptxl-Si-ester NP from paclitaxel conjugated to a trimethoxysilane group (Ptxl-Si) and an ester-bond-bridged triethoxysilane group (Si-ester-Si).

The unique strategy described herein allows for the formulation of degradable, silica-drug conjugated nanoparticles in gram-scale with monodisperse size controllable between 20 and 200 nm. Thus, methods are provided that allow for the controlled formulation of degradable silica-drug conjugated nanoparticle systems with controllable size and in large quantities, thereby providing a new class of silica-drug conjugated nanoparticles. Important features of this class of nanoparticles include precisely controllable size, degradability and scalability. Compared to monodispersed nanoparticles prepared by top-down techniques, small sized particles (<100 nm) of the silica-drug conjugated nanoparticles are more easily prepared and the methods can be more easily scaled up. These nanoparticles and methods for preparing them therefore represent a major breakthrough of nanomedicine and have broad clinical applications.

Preparation of Drug-Silicate Conjugates for Incorporation into Nanoparticles.

To demonstrate the concept a size controlled preparation of silica-drug nanoparticle preparation, 1-pyrenemethanol containing trimethoxysilane (Pyr-Si) was prepared for use as a model for the drug-Si group. The Pyr-Si conjugate can be prepared as illustrated by the reactions illustrated in Scheme 1.

Scheme 1.

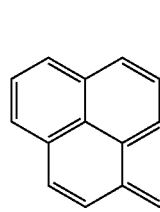 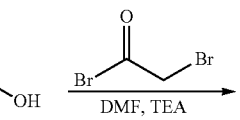

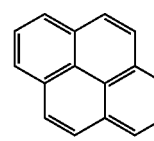 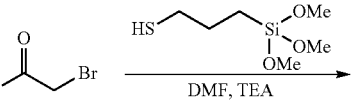

Pyr—Br

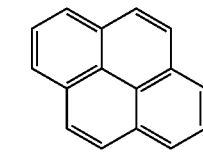

Pyr—Si

First, 1-pyrenemethanol was converted to Pyr-Br by reacting with bromoacetyl bromide, which can be further reacted with 3-(trimethoxysilyl)propane-1-thiol to form Pyr-Si. The structures of Pyr-Br and Pyr-Si were confirmed by analysis of their $^1$H NMR spectra.

A similar strategy was applied for paclitaxel-conjugated particles. Ptxl-Si was obtained by a two step sequence of reactions, shown in Scheme 2. The structure of Ptxl-Br was confirmed by analysis of MALDI mass spectrometry. Nanoparticles prepared from Ptxl-Si conjugates can be used to treat, for example, ovarian cancer and colon cancer.

Scheme 2.

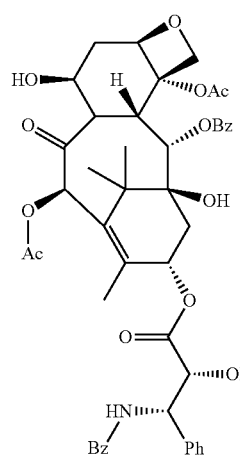 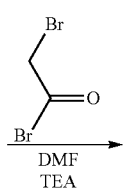

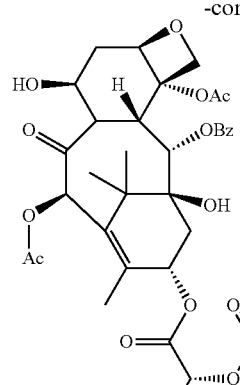 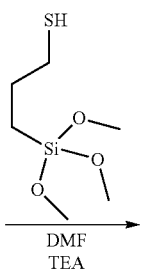

Ptxl-Br

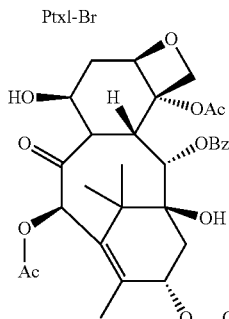

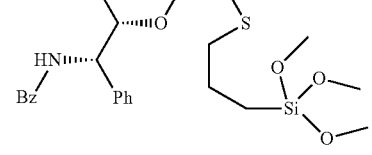

Ptxl-Si

Figure 13:
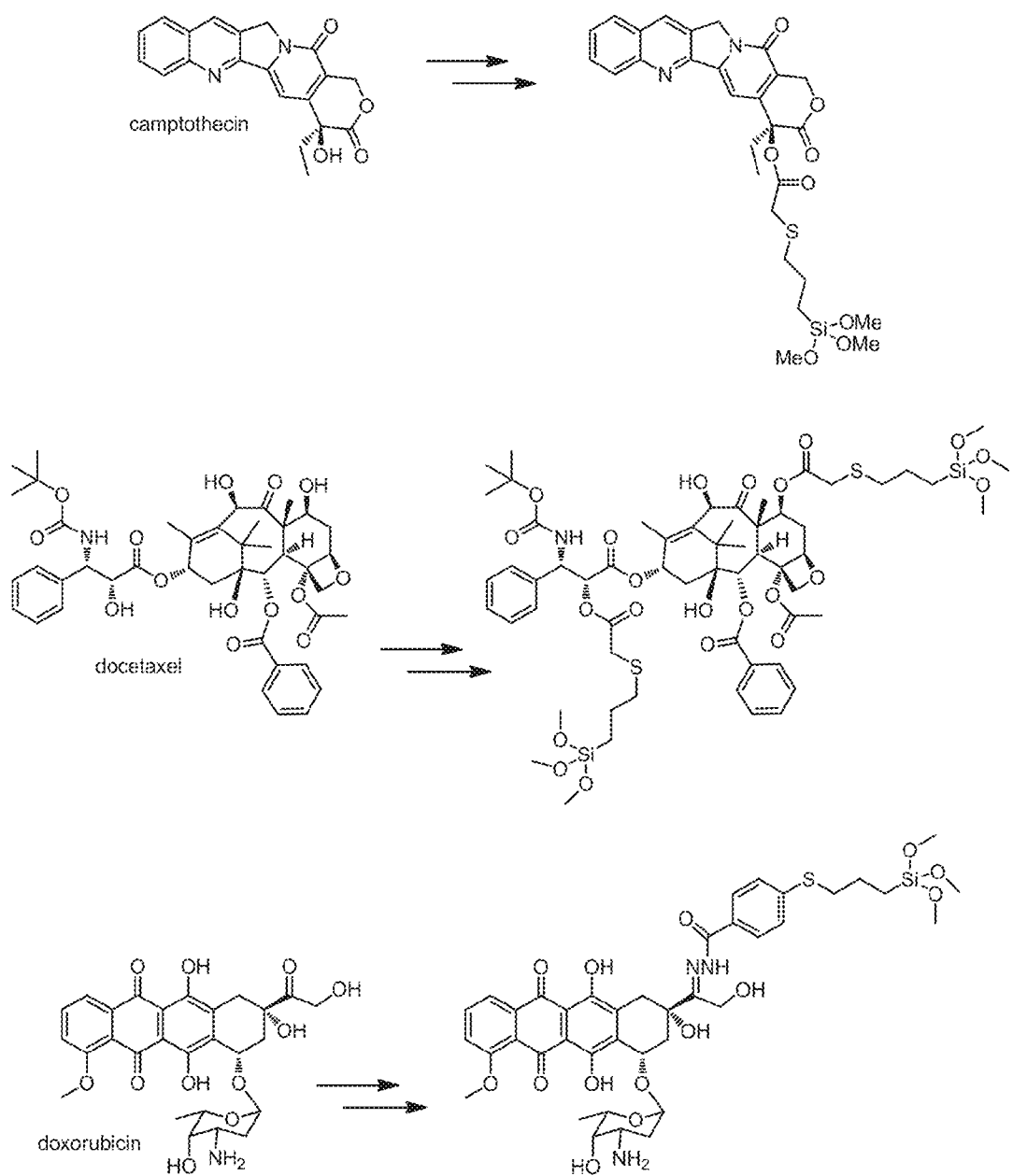
FIG. 13. Examples of anticancer drugs that can be incorporated to silica nanoparticles, according to various embodiments.

Similar methods can be used to prepare drug-sil groups from any hydroxyl-containing, amine-containing, or carboxylic acid-containing drug, to provide a variety of new drug delivery systems. Examples of drugs that can be conjugated to a silicon atom to provide drug-sil groups include camptothecin, paclitaxel, docetaxel and doxorubicin, among others. FIG. 13 illustrates examples of various other linking groups and the drug-sil molecules that can be prepared by modification of the drug with a linker and silane group. Camptothecin-nanoparticle conjugates can be used to treat, for example, breast cancer, lung cancer, and ovarian cancer. Docetaxel-nanoparticle conjugates can be used to treat, for example, breast cancer, lung cancer, prostate cancer, stomach cancer, and head/neck cancer. Doxorubicin-nanoparticle conjugates can be used to treat, for example, breast cancer, lung cancer, ovarian cancer, prostate cancer, stomach cancer, head/neck cancer, and other conditions known to be treated by doxorubicin.

Drug-sil molecules can also be used as linkers in the preparation of the silica nanoparticles. See for example, the structure of the drug-sil conjugate in FIG. 13.

Nanoparticles having various conjugated moieties can be prepared for use as diagnostic reagents. FIG. 14 shows several examples of imaging probes that can be incorporated into silica nanoparticles by modifying their structures, for example, to include the silicate moieties as shown in the figure.

Synthesis of Degradable Organo-Group Bridged Trialkoxysilanes.

To prepare "degradable" silica NPs, organo-group bridged trialkoxysilanes were used to form the matrix of the silica NPs in place of some or all of the TEOS. Representative syntheses of Si-ester-Si and Si-acetal-Si groups are shown below in Scheme 3. The structures were confirmed by analysis of $^1$H NMR spectra. Compared to the starting materials, the proton of vinyl groups disappeared in both cased after conjugation to silica, indicating completion of the hydrosilation reaction.

Scheme 3. Preparation of Si-ester-Si and Si-acetal-Si compounds.

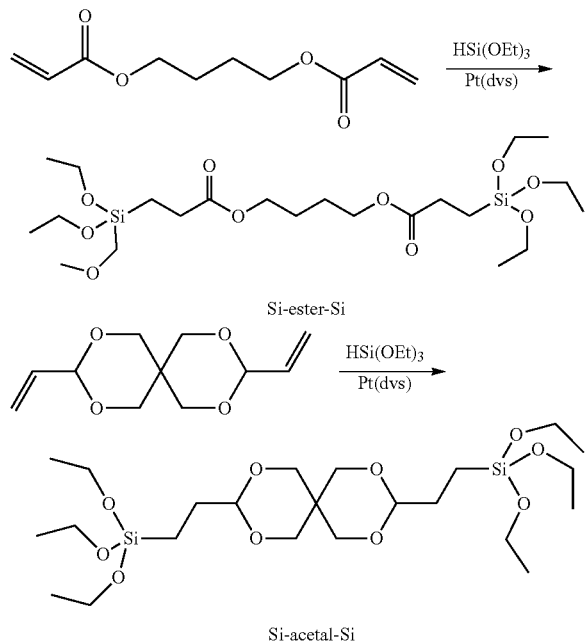

Preparation of Silica-Drug Conjugated Nanoparticles.

Pyr-Si was used as a drug-Si model to formulate silica-drug conjugated nanoparticles using the Stober method by co-condensation with TEOS. Highly monodispersed silica-drug conjugated nanoparticles with precisely controllable sizes were obtained. Silica NPs with diameters of about 25 to about 200 nm were obtained by varying the condition from the standard Stober method (FIG. 1b). By varying the ratios of water, ammonium hydroxide, and TEOS, the desired sized particles could be precisely controlled (see Tables 1-3).

For example, to prepare 25 nm diameter Pyr-Si NPs, 1 mL methanol, 0.45 mL DI water and 90 µL concentrated ammonia hydroxide were mixed. TEOS (31.2 µL) was then added to the mixture, followed by the addition of Pyr-Si as a solution in DMSO. The mixture was gently stirred for 12 hours to form the NPs. The NPs were collected by centrifugation at 13.2 K rpm and were washed with ethanol three times. The NP sizes were measured by both Dynamic Light Scattering (DLS) and Scanning Electron Microscopy (SEM). All of the NPs obtained were highly monodispersed with narrow PDI. These results confirmed the achievement of a successful strategy for preparing silica-drug NPs with controllable sizes.

Ptxl-Si was then prepared to illustrate the preparation of a degradable Ptxl-Si-ester NP for therapeutic purposes. Highly monodispersed inorganic-organic hybrid silica NPs, 25 nm in diameter were obtained by using a reverse microemulsion system (size confirmed by SEM analysis). In this reverse microemulsion system, Triton X-100 and n-hexanol were used as a surfactant and a co-surfactant, respectively. A 7.5 mL aliquot of cyclohexane, 1.8 mL of n-hexanol and 1.77 mL of Triton X-100 were mixed together under stirring for 20 minutes. Then 480 µL DI water, 80 µL Si-ester-Si and 20 µL of dichloromethane solution of Ptxl-Si were added in 20 minute intervals. Afterward, 80 µL of 28% ammonium hydroxide was added to initiate the reaction. The reaction proceeded to completion, after 24 hour. The NPs were collected by centrifugation at 13.2 K rpm for 30 minutes.

Because the therapeutic agent is conjugated to the NP matrix through an ester bond, this Ptxl-Si-ester NP can be used as a controlled release drug formulation. To make the silica-drug NP itself degradable, Si-ester-Si instead of TEOS was used to form the matrix of inorganic-organic hybrid silica NPs. When the silica NP itself was made biodegradable, the resulting particle can then used for in vivo drug delivery applications. This degradation can be responsive to certain signals by strategically designing the structure of the "bridge" in Si-bridge-Si. For example, Si-acetal-Si (Scheme 3) NPs can offer an acid responsively degradable drug delivery system. Thus, the controlled size, drug loading, drug release and scalability of optionally degradable silica-drug conjugated nanoparticles has been demonstrated. Aqueous and solid formulations of the particles can be prepared for use as therapeutic agents.

Other drug conjugated NPs can be prepared by the following procedure. For the preparation of 200 nm drug conjugated silica NPs, 1 mL methanol, 0.27 mL DI water and 0.24 mL concentrated ammonia can be mixed. Then 62.5 µL TEOS can be added to the mixture, followed by gentle stirring. Then 62.5 µL TEOS or a Si-bridge-Si compound can be added to the mixture, followed by the addition of 2 mg drug-sil in 20 µL of DMSO. The mixture is stirred gently (for example, at 100 rpm) at room temperature (~23° C.) to form the NPs. The NPs can then be collected by centrifugation, for example, at 13.2 k rpm. The NPs can be purified by washing with an alcoholic solvent, such as ethanol. The NP sizes and shapes can then be characterized, for example, by SEM at 5 kV. For further analysis, one drop of a dilute sample of silica NPs in ethanol can be placed onto a silicon wafer to dry in air. Size analysis can then be performed on captured digital images manually. Synthetic procedures are similar for different size drug conjugated silica NPs, except for the concentrations of TEOS, water and ammonia. Tables 1-3 summarize conditions for preparing silica NPs of various sizes.

Ex vivo tumor penetration study can be carried out with, for example, 12-13 week old female C57BL/6 mice bearing LLC tumors, which can be sacrificed to harvest the tumors when the tumors grow to a size of about 6.7 mm×8.0 mm Tumors can be ex vivo cultured with silica NPs 20 nm, 50 nm or 200 nm in diameter with IR783 labeling at concentration of 3 mg/mL NP in cell medium for 48 hours. Tumor without any treatment can serve as a control. Tumor sections (e.g., 20 µm in thick) can be collected by cryostat and mounted on glass slides for analysis. Fluorescence images can be taken by a Zeiss Axiovert 200M fluorescence microscope with 780 nm laser excitation. A tiling image can be taken with fixed exposure time to show the NP penetration in tumor sections. Plot profile of fluorescence in tumor sections can be analyzed by Image J.

Conjugation Using Linker L Groups.

Organic agents, such as therapeutic agents (drugs) and diagnostic agents and be linked to trialkoxysilane groups for incorporation into the silica nanoparticles through a linker, for example a linker group L. Linker groups L may also link together two trialkoxy silane groups to provide degradable silica nanoparticles. Suitable linkers L are those described in this patent and also include all other suitable linking groups and residues known in the art.

The mechanical and degradation properties, e.g. hydrolytic properties, of a linker comprising an organic agent may be determined by incorporating and/or modifying a linking group into the linker chain. Among other properties, selecting molecular weight and chemical composition of a linking group can advantageously affect the mechanical properties of the silica nanoparticle. The silica nanoparticles of the invention may comprise linkers within the silica matrix wherein an organic agent and a linking group(s) are bonded together through degradable linkages, such as ester, thioester, amide, carbonate, and many others known in the art, as well as combinations thereof. These linkages form biodegradable bonds that can be hydrolyzed, broken by proteolysis, or broken by other biological of biochemical processes when placed under physiological conditions, such as in contact with an appropriate medium, e.g. body tissues or fluids, to release the organic active agents.

In some embodiments, the linking group(s) may be selected in coordination with the actual agent(s) to impart desirable physical, chemical, and biological properties, such as fast or slow degradation in the presence of esterases, such as those found in body tissues and/or fluids, and the like. Other desirable characteristics that are influenced by the linker type are mechanical strength, flexibility, and ability to withstand application of mechanical stress without failure, low sticking to a surface so that adhesion to delivery vehicles and neighboring surfaces may be minimized, e.g. when implanted in an animal or human. Also important is resistance to sterilization conditions by different methods, e.g. gamma irradiation, electron beam (E beam), treatment with ethylene oxide, or other chemical or physical treatments providing sterilization.

Suitable linking groups typically comprise a divalent organic residue of molecular weight about 25, 40, 75, 100, 130 Daltons to about 100, 170, 250, 330, 400, 520 Daltons. In one embodiment, L comprises a divalent, branched or unbranched, saturated or unsaturated ($C_1$-$C_{25}$) hydrocarbon chain, where one or more carbon atoms may be further substituted by —O—, ($C_1$-$C_6$) alkoxy, ($C_3$-$C_6$) cycloalkyl, ($C_1$-$C_6$) alkanoyl, ($C_1$-$C_6$) alkanoyloxy, ($C_1$-$C_6$) alkoxycarbonyl, ($C_1$-$C_6$) alkylthio, azido, cyano, nitro, halo, hydroxy, oxo, carboxy, aryl, aryloxy, heteroaryl, heteroaryloxy, or —$NR^2$— wherein R is H or ($C_1$-$C_6$)alkyl. In one embodiment, the linking group(s) may be a ($C_3$-$C_{20}$) dicarboxlyic acid hydrocarbon residue.

In one embodiment, the linker L may be a linking group that may be present a chain along with the organic agent(s) through bonds that release the agent(s) under certain environmental conditions. Examples of bonds are esters, thioesters, amides, thioamides, urethanes, carbamates, thiocarbamates, carbonates, thiocarbonates, and any others than fulfill a similar function. This includes combinations and mixtures thereof. The linking bonds may comprise other groups, and atoms, including P, C, O, S, halogens, metals, and other inorganic and organic atoms provided that they form labile bonds that may release the agent(s) conjugated to the linker under appropriate circumstances. The linking group(s) may be selected as well to impart to the nanoparticle desirable physical, chemical, and/or biological properties. Suitable linking groups are widely known in the art, and need not be fully detailed here. Examples are described in U.S. Pat. Nos. 6,613,807; 6,328,988; 6,365,146; 6,468,519; 6,486,214; 6,497,895; 6,602,915; 6,613,807; U.S. Published Patent Appins. 2002/0071822 A1; 2002/0106345 A1; 2003/0035787 A1; 2003/0059469 A1; 2003/0104614 A1; 2003/0170202 A1; U.S. Ser. Nos. 09/508,217; 10/368,288; 10/622,072; 10/646,336; 10/647,701; and International Patent Applications WO 99/12990; WO 01/28492; WO 01/41753; WO 01/58502; WO 02/09767; WO 02/09768; WO 02/09769; WO 03/005959; WO 03/046034; WO 03/065928; and WO 03/072020.

In some embodiments, the linking group L can be a divalent organic radical having a molecular weight (MW) about 25, or 40 Daltons to about 200, or 400 Daltons.

L may also be any substituted and unsubstituted hydrocarbon unit, such as, for example, propane, butane, pentane, etc. A suitable number of carbon atoms includes any number of carbon atoms that will result in a functional linker, e.g., about 2 to about 20 carbon atoms, about 2 to about 18 carbon atoms, about 4 to about 16 carbon atoms, about 4 to about 14 carbon atoms, about 6 to about 16 carbon atoms, about 8 to about 12 carbon atoms, or about 6 to about 10 carbon atoms. Further, the nature of the linking group L is not critical provided the linker possesses acceptable mechanical and chemical properties and release kinetics to form silica nanoparticles for the selected therapeutic application. For example, the linking group L can be a divalent organic radical having a molecular weight of from about 100, 200, 250, or 400 to about 500, 600, 700, or 800 Dalton, and a length of from about 5, 10, 30, or 40 to about 50, 75, or 100 Angstroms using standard bond lengths and angles. The linking group may be biologically inactive, or may itself possess biological or other activity.

One silica nanoparticle comprises L representing a residue of a linking group that, independently from one another, comprises linear or branched ($C_3$-$C_{20}$) aliphatic, alicyclic or aromatic residue that may be further substituted, as described above. In various embodiment, the active agent can be paclitaxel, camptothecin, docetaxel, doxorubicin, rapamycin, dasatinib, cyclopamine, cyclosporine A, FK506, or other hydroxyl-containing drugs, or a combination thereof. The linker can be a hydrocarbon chain (e.g., about 4 to about 20 carbon atoms) that includes an ester group and a thioether within the chain. The nature and presence of the linking group L is not critical as long as it does not negatively impact the linker's properties and release kinetics for the selected therapeutic application.

In one embodiment, the linking group L can comprises a divalent organic residue of molecular weight about 25, 40, 60, 100, 130, or 150 Daltons to about 80, 110, 125, 140, 170, 250, 370, or 400 Daltons, and any combination thereof. In another embodiment the linking group(s) L comprises a length of about 5, 10, 15, 20, or 25 Angstrom to about 30, 35, 45, 50, 75, or 100 Angstrom using standard bond lengths and angles. In some embodiments, the linking group may comprise other functional groups including hydroxy, mercapto, amine, halo, SH, —O—, —C=O, —N=, —P=, or carboxylic acid, as well as others that may be used to modify the properties of the linker.

In one embodiment, the linking group may incorporate other biodegradable groups such as alpha-ester (lactate, glycolate), ε-caprolactone, ortho-ester, or enzymatically biodegradable groups such as amino acids. In another embodiment, the linking group may be a water-soluble, non-biodegradable segment such as a polyethylene glycol (PEG), polyvinyl alcohol (PVA) or polyvinyl pyrrolidone (PVP). In yet another embodiment, the linking group may be a water-insoluble, non-biodegradable segment such as polypropylene glycol (PPG), polyetherurethane (PEU), or poly(n-alkyl ether). In still another embodiment, the linker may be an amorphous or semicrystalline biodegradable polymer, such as poly(d,l-lactide), poly(trimethylene carbonate), poly(dioxanone), polyanhydridepoly(orthoester) poly(glycolide), poly(1-lactide) poly(ε-caprolactone) and co-polymers of ε-caprolactone, glycolide, trimethylene carbonate, dioxanone, d,l-lactide, 1-lactide and d-lactide. In another embodiment, the linking group may have surfactant properties, such as a Pluronic block copolymer with polyethylene glycol and polypropylene glycol blocks, and in another it may have polar or charged moieties, including carboxylic acid groups from poly (acrylic acid) and poly(alginates), sulfonic acid groups from poly(2-acrylamido-2-methyl-propanesulfonicacid) (AMPS), hydroxy groups from poly(vinyl alcohol), polysaccharides and poly(alginates), and amino groups from poly(L-lysine), poly(2,2-dimethylaminoethyl methacrylate) and poly(amino acids).

In addition, the linking group may be a divalent, branched or unbranched, saturated or unsaturated, hydrocarbon chain, having from 1 to 25 carbon atoms, wherein one or more, e.g. 1, 2, 3, or 4, of the carbon atoms is optionally replaced by (—O—), (—S—), (—P—), or (—NR—), and wherein the chain is optionally substituted with one or more, e.g. 1, 2, 3, or 4, substituents comprising ($C_1$-$C_6$) alkoxy, ($C_3$-$C_6$) cycloalkyl, ($C_1$-$C_6$) alkanoyl, ($C_1$-$C_6$) alkanoyloxy, ($C_1$-$C_6$) alkoxycarbonyl, ($C_1$-$C_6$) alkylthio, azido, cyano, nitro, halo, hydroxy, oxo, carboxy, aryl, aryloxy, heteroaryl, or heteroaryloxy, among others. The linking group may be a divalent ($C_2$-$C_{22}$) branched or unbranched, saturated or unsaturated hydrocarbon chain optionally further substituted with one or more, e.g. 1, 2, 3, or 4, substituents comprising ($C_1$-$C_6$) alkoxy, ($C_3$-$C_6$) cycloalkyl, ($C_1$-$C_6$) alkanoyl, ($C_1$-$C_6$) alkanoyloxy, ($C_1$-$C_6$) alkoxycarbonyl, ($C_1$-$C_6$) alkylthio, azido, cyano, nitro, halo, hydroxy, oxo, carboxy, aryl, aryloxy, heteroaryl, or heteroaryloxy, among many others.

The linking group may be a divalent, branched or unbranched, saturated or unsaturated ($C_3$-$C_{31}$) hydrocarbon chain, preferably of uneven number of carbons, with one or more optionally substituted by —O— or —NR— (wherein R is H or ($C_1$-$C_6$)alkyl); or a divalent, branched or unbranched, saturated or unsaturated, hydrocarbon chain, having from about 3, 6, or 9 to about 12 or 15 carbon atoms, wherein one or more, e.g. 1, 2, 3, or 4, of the carbon atoms is optionally replaced by —O— or —NR— or —S—, and wherein the chain is optionally substituted on carbon with one or more, e.g. 1, 2, 3, or 4, substituents selected from the group consisting of ($C_1$-$C_6$) alkoxy, ($C_3$-$C_6$) cycloalkyl, ($C_1$-$C_6$) alkanoyl, ($C_1$-$C_6$) alkanoyloxy, ($C_1$-$C_6$) alkoxycarbonyl, ($C_1$-$C_6$) alkylthio, azido, cyano, nitro, halo, hydroxy, oxo, carboxy, aryl, aryloxy, heteroaryl, and heteroaryloxy. The linking group may be a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—S—), (—P—), or (—NR—); or a divalent branched or unbranched, saturated or unsaturated, hydrocarbon chain, having from 3 to 15 carbon atoms; or a divalent, branched or unbranched, (C6-C10) hydrocarbon chain; or a divalent ($C_7$-$C_9$) hydrocarbon chain, or a divalent C8 hydrocarbon chain.

Thus, different embodiments may be prepared changing the chemical structure of the linker for the desired silica nanoparticle. For example, in one embodiment, the linker may be prepared from an agent(s) of chemical formula $Z_1$—$R^1$—$Z_2$ and a linker precursor of formula $X_1$-L-$X_2$, wherein $Z_1$, $Z_2$, $X_1$, and $X_2$, independently from one another, comprise functional groups that are able to form degradable bonds in situ. Examples of these functional grouped are shown in Table 7 below.

TABLE 7

Functional Groups and Linking Bonds.

| Agent Functional Group ($Z_1$ or $Z_2$) | Linker Functional Group ($X_1$ or $X_2$) | Linking Bond (A) |
|---|---|---|
| —$CO_2H$ | —OH | ester |
| —$CO_2H$ | —SH | amide |
| —$CO_2H$ | —NHR | thioester |
| —OH | —$CO_2H$ | ester |
| —SH | —$CO_2H$ | thioester |
| —NHR | —$CO_2H$ | amide |

An organic agent and a linker precursor or two linker precursors may be linked, for example, by condensation, to provide a linking group wherein each linking bond A, independently from one another, comprises a bond that is degradable in situ, e.g. in vivo when administered to a living organism. Examples of breakable bonds comprise an ester, thioester, thioamide, azo, carbonate, or amide. Depending on the reactive functional groups $Z_1$ and $Z_2$ present in the organic agent, a corresponding functional group $X_1$ or $X_2$ may be selected for the linking group to provide one or more of the breakable bonds described above in the formation of the linker L. The linkers may be prepared in at least two general manners or embodiments, which embodiments are expanded by the addition, and various permutations, of the methods illustrated by the preparatory schemes herein.

Pharmaceutical Formulations

The nanoparticles described herein can be used to prepare therapeutic pharmaceutical and diagnostic compositions. The nanoparticles may be added to compositions as a dry powder or in the form of a liquid dispersion. The nanoparticles described herein can be formulated as pharmaceutical or diagnostic compositions and can be administered to a mammalian host, such as a human patient, in a variety of forms. The forms can be specifically adapted to a chosen route of administration, e.g., oral or parenteral administration, by intravenous, intramuscular, topical or subcutaneous routes.

The nanoparticles may be systemically administered in combination with a pharmaceutically acceptable vehicle, such as an inert diluent or an assimilable edible carrier. For oral administration, nanoparticles can be enclosed in hard or soft shell gelatin capsules, compressed into tablets, or incorporated directly into the food of a patient's diet. Nanoparticles may also be combined with one or more excipients and used in the form of ingestible tablets, buccal tablets, troches, capsules, elixirs, suspensions, syrups, wafers, and the like. Such compositions and preparations typically contain at least 0.1 wt. % of nanoparticles. The wt. % of nanoparticles in the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the nanoparticles, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the nanoparticles may be further incorporated into sustained-release preparations and devices.

The nanoparticles may be administered intravenously or intraperitoneally by infusion or injection. Dispersions of the nanoparticles can be prepared in water, optionally mixed with a nontoxic surfactant. Dispersions can also be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders adapted for the extemporaneous preparation of sterile injectable or infusible solutions or dispersions, optionally encapsulated in liposomes. The ultimate dosage form should be sterile, fluid and stable under the conditions of manufacture and storage. A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable compositions can be prepared by incorporating the nanoparticles in a desired amount in the appropriate solvent with various of the other ingredients enumerated above, as required, followed by filter sterilization. In the case of sterile powders for the preparation of sterile injectable compositions, methods of preparation can include vacuum drying and freeze drying techniques, which yield a powder of the nanoparticles plus any additional desired ingredient present in the previously sterile-filtered solutions.

For topical administration, nanoparticles may be applied in pure form, however, it will generally be desirable to administer the nanoparticles to the skin as a composition or formulation, for example, in combination with a dermatologically acceptable carrier, which may be a solid, liquid, or gel.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which nanoparticles can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user. Examples of dermatological compositions for delivering active agents to the skin are known to the art; for example, see U.S. Pat. No. 4,608,392 (Jacquet et al.), U.S. Pat. No. 4,992,478 (Geria), U.S. Pat. No. 4,559,157 (Smith et al.), and U.S. Pat. No. 4,820,508 (Wortzman). Such dermatological compositions can be used in combinations with the compounds described herein.

Useful dosages of the nanoparticles described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of nanoparticles, or a composition thereof, required for use in treatment will vary not only with the particular compound or salt selected but also with the route of administration, the nature of the condition being treated, and the age and condition of the patient, and will be ultimately at the discretion of an attendant physician or clinician.

The nanoparticles can be conveniently administered in a unit dosage form, for example, containing 5 to 1000 mg/m$^2$, conveniently 10 to 750 mg/m$^2$, most conveniently, 50 to 500 mg/m$^2$ of nanoparticles or drug-in-nanoparticles per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The nanoparticles described herein can be effective anti-tumor agents and can have higher potency and/or reduced toxicity as compared to formulations of the respective drug that is not conjugated to a nanoparticle. The invention provides therapeutic methods of treating cancer in a mammal, which involve administering to a mammal having cancer an effective amount of a nanoparticles composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a drug-conjugated nanoparticles to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

General Experimental Information

All chemicals including tetraethyl orthosilicate (TEOS, 99.999%), pyrenemethanol (Pyr-OH) and camptothecin (Cpt) were purchased from Sigma-Aldrich (St Louis, Mo., USA) and used as received unless otherwise noted. mPEG$_{5k}$-triethoxysilane (mPEG-sil) (FIG. 1b) was purchased from Laysan Bio (Arab, Ala., USA) and used as received. All anhydrous solvents were purified by passage through dry alumina columns and kept anhydrous using molecular sieves. The polyclonal rabbit anti-human Von Willebrand Factor (Factor VIII-related antigen) was purchased from Dako (Carpinteria, Calif., USA). The FITC-conjugated goat polyclonal secondary antibody to rabbit IgG was purchased from Abcam (Cambridge, Mass., USA).

The low resolution electrospray ionization mass spectrometry (LR-ESI-MS) experiments were performed on a Waters Quattro II Mass Spectrometer. Matrix Assisted Laser Desorption/Ionization-Time of Flight mass spectrometry (MALDI-TOF MS) spectra were collected on an Applied Biosystems Voyager-DE™ STR system. HPLC analyses were performed on a System Gold system (Beckman Coulter, Fullerton, Calif., USA) equipped with a 126P solvent module, a System Gold 128 UV detector and an analytical C18 column (Luna C18, 250×4.6 mm, 5 Phenomenex, Torrance, Calif., USA). The NMR experiments were conducted on a Varian U500, a VXR500 or on a UI500NB (500 MHz) NMR spectrometer. The sizes and monodispersities of silica particles were determined on a Hitachi 54800 high resolution Scanning Electron Microscope (SEM). The real time monitoring of the drug (dye)-silica NC sizes and monodispersities were done by ZetaPlus dynamic light-scattering (DLS) detector (15 mW laser, incident beam=676 nm, Brookhaven Instruments, Holtsville, N.Y., USA).

The solid forms of NCs were obtained by lyophilizing the NC/lyoprotectant solution using a Freezone benchtop lyophilizer (Fisher Scientific, Fairland, N.J., USA). The HeLa cells (ATCC, Manassas, Va., USA) used for MTT assays and cellular internalization studies were cultured in MEM medium containing 10% Fetal Bovine Serum (FBS), 1000 units/mL aqueous Penicillin G and 100 µg/mL streptomycin (Invitrogen, Carlsbad, Calif., USA). The absorbance wavelength on a microplate reader (Perkin Elmer, Victor$^3$™ V, Waltham, Mass., USA) was set at 590 nm for MTT assay. The Lewis lung carcinoma (LLC) cells (ATCC) were cultured in DMEM medium containing 10% FBS, 1000 units/mL aqueous Penicillin G and 100 µg/mL streptomycin. The confocal microscopy images for cell internalization studies were taken on a Zeiss LSM700 Confocal Microscope (Carl Zeiss, Thornwood, N.Y., USA) using a 63×/1.4 oil lens with excitation wavelength set at 405 nm and 555 nm. The flow cytometry analysis of cells was conducted with a BD FACSCanto 6 color flow cytometry analyzer (BD, Franklin Lakes, N.J., USA).

For the ex vivo study, the flash frozen tumor tissue embedded with optimum cutting temperature (O.C.T.) compound (Sakura Finetek, USA) was sectioned (20 µm thick) with a Leica CM3050S cryostat and mounted on glass slides. The tissue sections were observed on a fluorescence microscope (Zeiss Axiovert 200M, city, state, country) with 780 nm excitation wavelength. For the in vivo study, the formalin-fixed, paraffin-embedded tumor sections measuring 5 µM in thickness were prepared by the Veterinary Diagnostic Laboratory histopathology service at University of Illinois at Urbana-Champaign (Urbana, Ill., USA). The tissue sections were analyzed under Zeiss LSM700 confocal microscope for in vivo tumor penetration study. For biodistribution studies, the organs were fixed in 10% formalin; the fluorescence of the whole organ was measure ex vivo at 800 nm wavelength emission using Odyssey infrared mouse imaging system (LI-COR, Lincoln, Nebr., USA). The histopathological characterizations of tissues for mononuclear cell infiltrates (neutrophils and macrophages) were performed at College of Veterinary Medicine North Carolina State University. C57BL/6 mice (female) were purchased from Charles River Laboratories (Wilmington, Mass., USA). Feed and water were available ad libitum. The study protocol was reviewed and approved by the Animal Care and Use Committee (IACUC) of University of Illinois at Urbana Champaign. For both ex vivo and in vivo studies, C57BL/6 mice were injected subcutaneously in the right flank with 1×10$^6$ Lewis lung carcinoma (LLC) cells suspended in a 1:1 mixture of HBS buffer and matrigel (BD Biosciences, Franklin Lakes, N.J., USA).

Example 1

Preparation and Analysis of Therapeutic Nanoparticles

This example describes the synthesis of drug- and drug model-containing trialkoxysilanes (Drug-sil) and the preparation of therapeutic nanoparticles using Drug-sil compounds.

1. Preparation of Drug-sil Compounds 1.1. Synthesis of pyrenemethyl 2-((3-(trimethoxysilyl)propyl)thio)acetate (Pyr-sil)

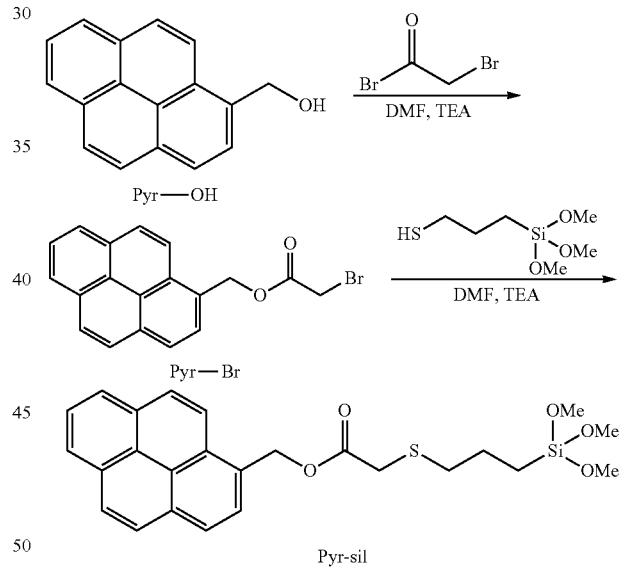

Pyren-1-ylmethyl 2-bromoacetate (Pyr-Br): Pyrenemethanol (Pyr-OH) (109.6 mg, 0.47 mmol) in 1.0 mL DMF (anh) was treated with 180 µL TEA (anh, 1.29 mmol) and 2-bromoacetyl bromide (132.2 µL, 1.50 mmol) in 1 mL dichloromethane. The mixture was stirred at RT (~23° C.) for 17 hours. After the solvent was evaporated, the crude product was purified by silica gel column (Hex/EtOAc=2/1) to give 167 mg final product as a yellow solid (yield 90%). $^1$H NMR (CDCl$_3$, 500 MHz): δ 8.28-8.03 (m, 9H, ArH), 5.94 (s, 2H, ArCH$_2$), 3.90 (s, 2H, CH$_2$Br). ESI: 375, [M+Na]$^+$.

Pyrenemethyl 2-((3-(trimethoxysilyl)propyl)thio)acetate (Pyr-sil): Pyr-Br (40.2 mg, 0.11 mmol) in 0.5 mL DMF (anh) was treated with 180 µL TEA (anh, 1.29 mmol) and (3-mercaptopropyl)trimethoxysilane (210 µL, 1.10 mmol). The mixture was stirred at RT for 11 h. After the solvent was evaporated, the crude product was purified by silica gel column (Hex/EtOAc=3/1). HPLC purity: >95%. ¹H NMR (CDCl₃, 500 MHz): δ 8.31-8.03 (m, 9H, ArH), 5.91 (s, 2H, ArCH₂), 3.51 (s, 9H, (CH₃O)₃Si), 3.29 (s, 2H, CH₂Br), 2.62 (t, 2H, SCH₂), 1.67 (m, 2H, CH₂), 0.65 (t, 2H, CH₂Si). ¹³C NMR (CDCl₃, 500 MHz): δ 170.99, 132.09-121.49, 65.75, 50.80, 41.96, 35.75, 33.74, 22.63. ESI: 469.2, [M+H]⁺.

1.2. Synthesis of Cpt-S-sil

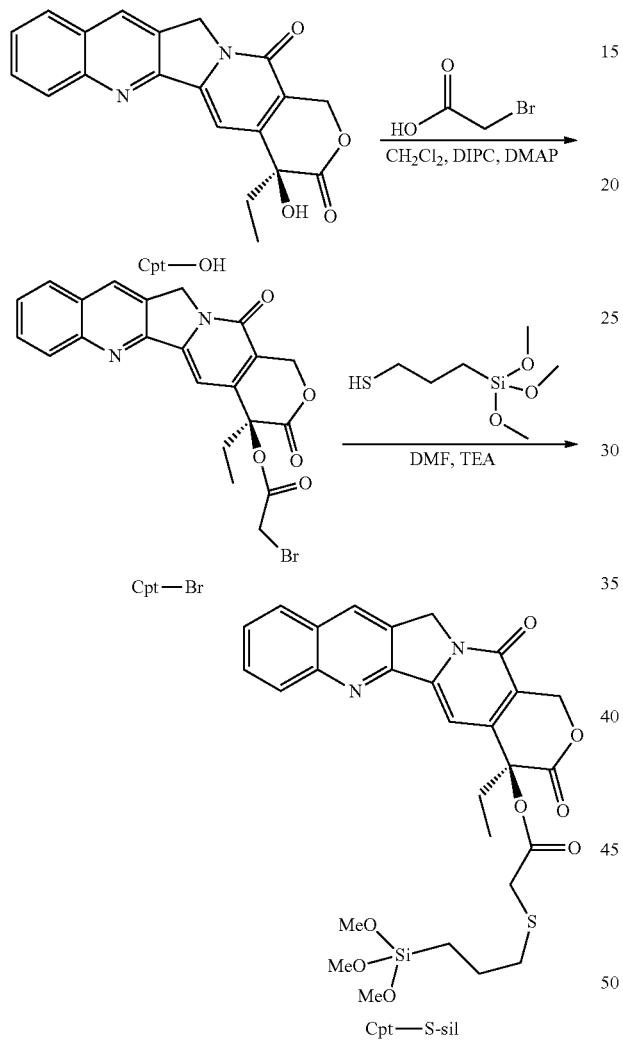

Cpt-Br: Camptothecin (Cpt) (10.4 mg, 0.030 mmol) was suspended in 0.5 mL dichloromethane (anh) followed by addition of 4-dimethylaminopyridine (0.4 mg, 0.003 mmol), bromoacetic acid (30 mg, 0.18 mmol) and diisopropylcarbodiimide (26 μL, 0.18 mmol). The mixture was stirred at RT for 24 hours. The reaction was monitored by HPLC. After the solvent was evaporated in vacuum, the crude product was purified by silica column (CH₂Cl₂/MeOH=100/1). ¹H NMR (CDCl₃, 500 MHz): δ 8.40 (s, H), 8.22 (d, H), 7.94 (d, H), 7.84 (t, H), 7.67 (t, H), 7.28 (s, H), 5.70 (d, H), 5.42 (d, H), 5.30 (s, 2H), 3.84 (m, 2H), 2.32 (q, H), 2.20 (q, H), 1.00 (t, 3H). ¹³C NMR (CDCl₃, 500 MHz): δ 167.07, 166.21, 157.51, 152.05, 149.18, 146.79, 145.14, 131.40, 130.91, 129.99, 128.66, 128.45, 128.42, 128.32, 120.64, 95.93, 88.63, 67.46, 50.22, 32.07, 25.19, 7.77. HPLC purity: >95%. MALDI: 471.1, [M+H]⁺.

Cpt-S-sil: Cpt-Br (6.5 mg, 0.014 mmol) was dissolved in 0.5 mL DMF (anh). TEA (9 μL, 0.07 mmol) and (3-mercaptopropyl)trimethoxysilane (4 μL, 0.021 mmol) was added and the reaction mixture was stirred at RT for 3 h. After the solvent was evaporated in vacuum, the crude product was purified by prep TLC(CH₂Cl₂/MeOH=100/1). ¹H NMR (CDCl₃, 500 MHz): δ 8.40 (s, H), 8.21 (d, H), 7.94 (d, H), 7.82 (t, H), 7.66 (t, H), 7.35 (s, H), 5.68 (d, H), 5.40 (d, H), 5.29 (s, 2H), 3.47 (s, 9H), 3.84 (s, 2H), 2.65 (t, 2H), 2.28 (q, H), 2.17 (q, H), 1.68 (q, 2H), 0.99 (t, 3H), 0.75 (t, 2H). ¹³C NMR (CDCl₃, 500 MHz): δ 169.41, 167.49, 157.59, 152.57, 149.14, 146.57, 145.90, 131.38, 130.86, 129.96, 128.68, 128.42, 128.26, 120.39, 110.01, 96.19, 88.63, 67.30, 50.20, 46.25, 42.39, 35.54, 31.95, 23.74, 22.36, 7.85. HPLC purity: >95%. ESI: 585.3, [M+H]⁺; 607.3, [M+Na]⁺.

1.3. Synthesis of Cpt-NH-sil

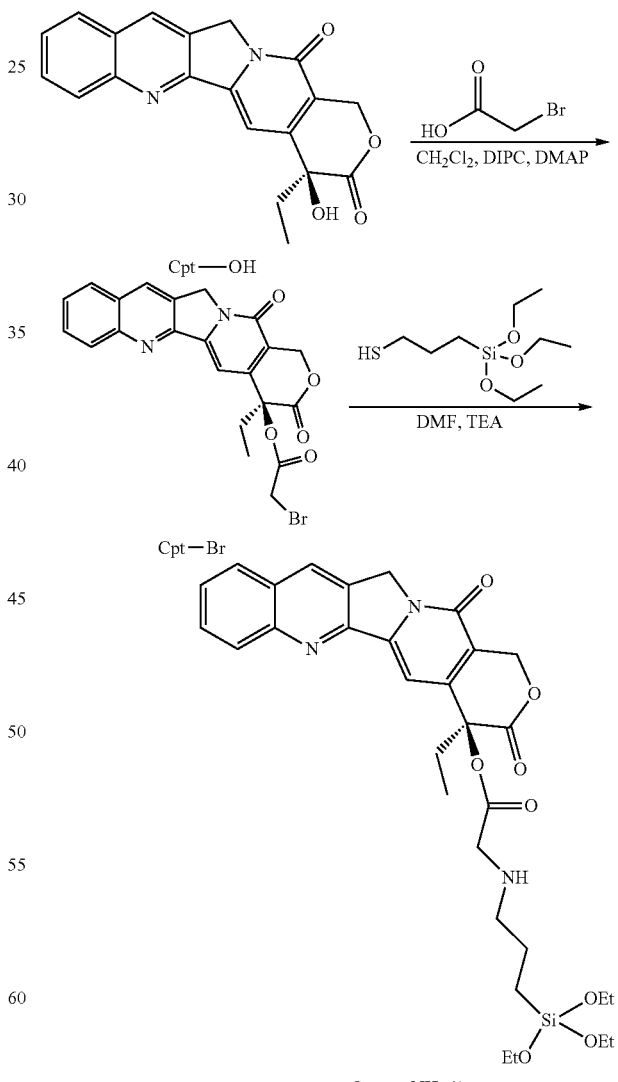

Cpt-Br (6.5 mg, 0.014 mmol) was dissolved in 0.5 mL DMF (anh). TEA (9 μL, 0.07 mmol) and (3-mercaptopropyl)

trimethoxysilane (4 μL, 0.021 mmol) was added and the reaction mixture was stirred at RT for 3 h. After the solvent was evaporated in vacuum, the crude product was purified by prep TLC(CH$_2$Cl$_2$/MeOH=100/1). $^1$H NMR (CDCl$_3$, 500 MHz): δ 8.40 (s, H), 8.20 (d, H), 7.94 (d, H), 7.82 (t, H), 7.65 (t, H), 7.20 (s, H), 5.66 (d, H), 5.40 (d, H), 5.28 (s, 2H), 3.73 (q, 6H), 3.58 (s, 2H), 2.66 (t, 2H), 2.28 (q, H), 2.16 (q, H), 1.63 (m, 2H), 1.20 (t, 9H), 0.96 (t, 3H), 0.63 (t, 2H). $^{13}$C NMR (CDCl$_3$, 500 MHz): δ 172.05, 167.61, 157.39, 152.49, 149.13, 146.61, 145.90, 131.44, 130.90, 129.87, 128.65, 128.44, 128.28, 120.54, 96.23, 76.44, 67.38, 58.87, 52.38, 50.44, 47.97, 31.68, 23.17, 18.50, 7.77. ESI: 610.3, [M+H]$^+$.
1.4. Synthesis of Ptxl-sil
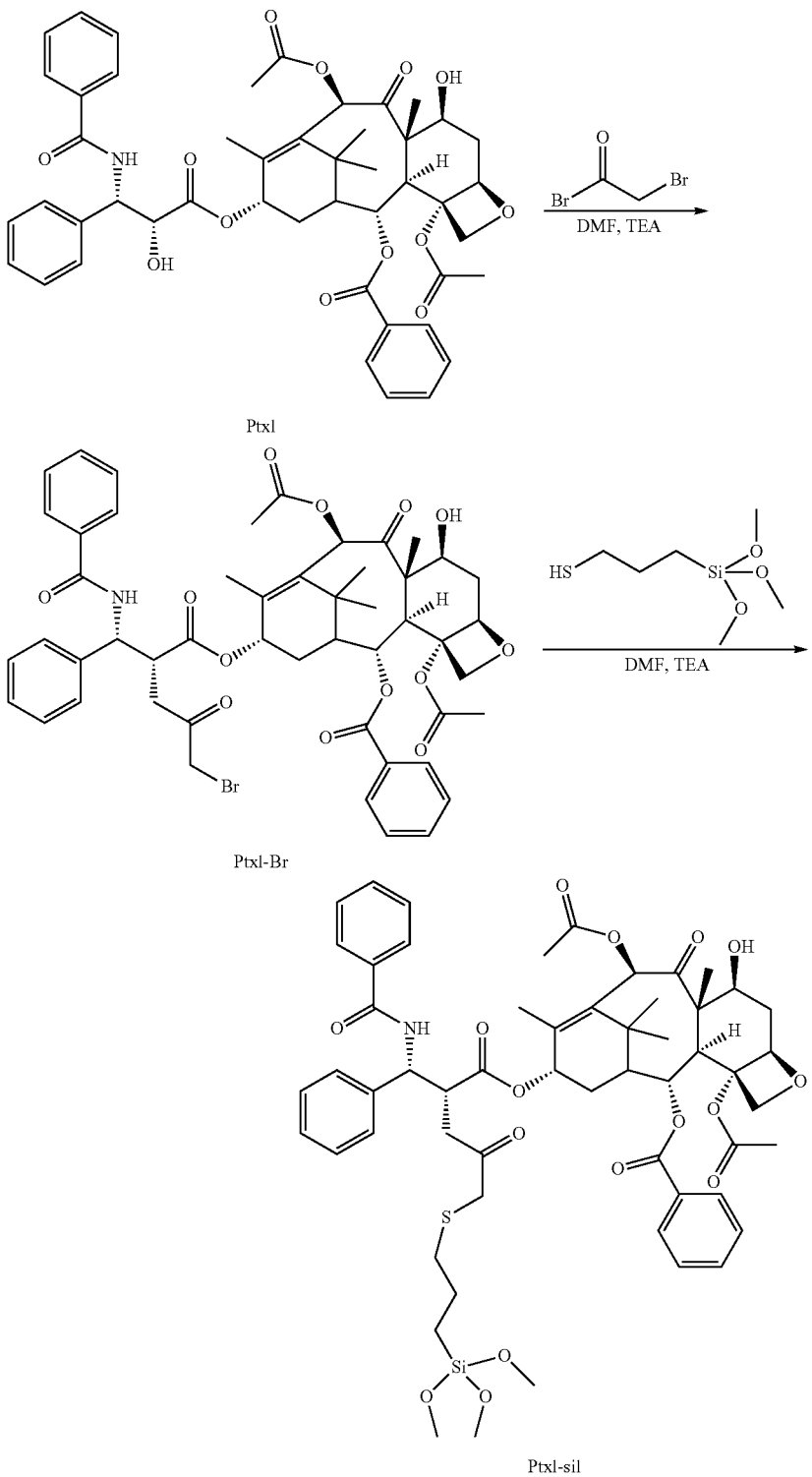
Ptxl
Ptxl-Br
Ptxl-sil Ptxl-Br: Paclitaxel (Ptxl, 19.8 mg, 0.023 mmol) in 1.0 mL THF (anh) was treated with 16.1 μL TEA (anh, 5 eq.) and 2-bromoacetyl bromide (4.7 mg, 0.023 mmol) in 0.1 mL dichloromethane at RT for 24 h. After the solvent was evaporated, the crude product was purified by prep TLC (Hex/EtOAc=1/2). HPLC purity: >95%. MALDI: 998.8, [M+Na]$^+$.

Ptxl-sil: Ptxl-Br (18.2 mg, 0.019 mmol) in 1.0 mL DMF (anh) was treated with 12 μL TEA (anh, 5 eq.) and 10 μL (0.051 mmol) (3-mercaptopropyl)trimethoxysilane at RT for 3 h. After the solvent was evaporated, the crude product was purified by prep TLC (Hex/EtOAc=1/2). HPLC purity: >95%. ESI: 1113.1, [M+Na]$^+$.

1.5. Synthesis of Dtxl-sil

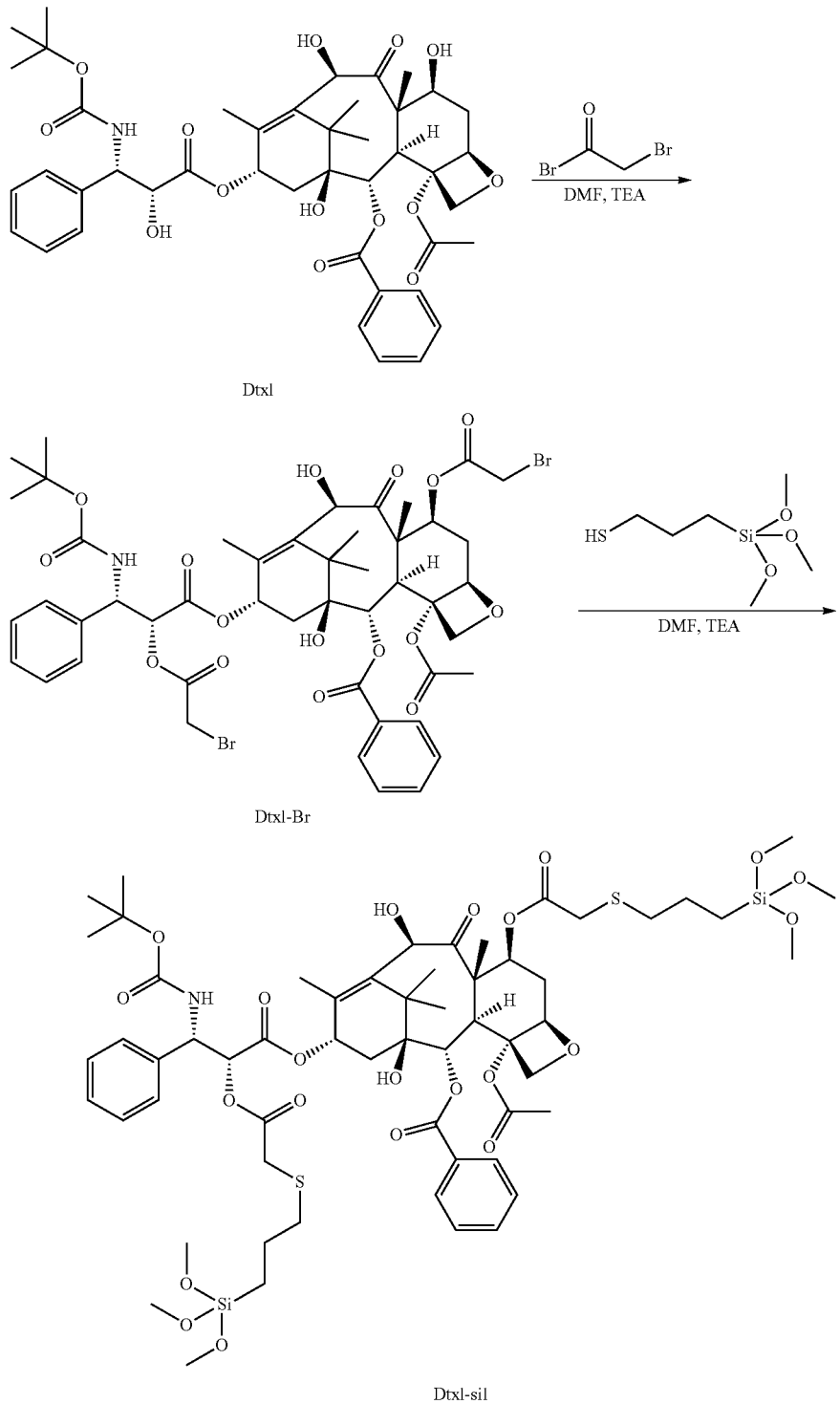

Dtxl-Br: Docetaxel (10.0 mg, 0.012 mmol) in 0.5 mL DMF (anh) was treated with 8.6 μL TEA (anh, 5 eq.), 4-dimethylaminopyridine (0.2 mg, 0.0016 mmol) and 2-bromoacetyl bromide (15 mg, 0.074 mmol) in 0.1 mL dichloromethane at RT for 12 h. After the solvent was evaporated, the crude product was purified by prep TLC (Hex/EtOAc=3/2). HPLC purity: >95%. MALDI: 1072.7, [M+Na]$^+$.

Dtxl-sil: Dtxl-Br (3.4 mg, 0.0032 mmol) in 0.5 mL DMF (anh) was treated with 5 μL TEA (anh) and 2 μL (0.010 mmol) (3-mercaptopropyl)trimethoxysilane at RT for 3 h. After the solvent was evaporated, the crude product was purified by prep TLC (Hex/EtOAc=1/2). HPLC purity: >95%. ESI: 1303.0, [M+Na]$^+$.

1.6. Synthesis of Infrared Dye (IR783) Containing Silane Group (IR783-sil)

IR783 (23.5 mg, 0.031 mmol) in 1.0 mL DMF (anh) was treated with 22 μL TEA (5 eq.) and 30 μL (5 eq.) (3-mercaptopropyl)trimethoxysilane at 55° C. for 12 hours. After the solvent was evaporated, the crude product was directly used for fluorescence labeling. HPLC purity: >80%. ESI (m/z): calcd for $C_{44}H_{61}N_2O_9S_3Si$, 885 [M]. found, 886 [M+H]$^+$.

1.7. Synthesis of an Ester Bond Bridged Silane (EBB-sil)

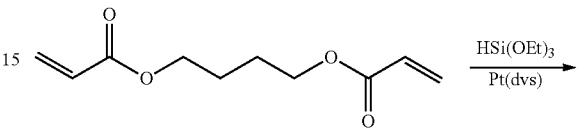

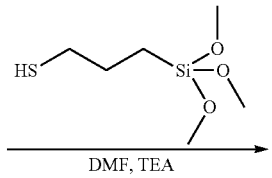

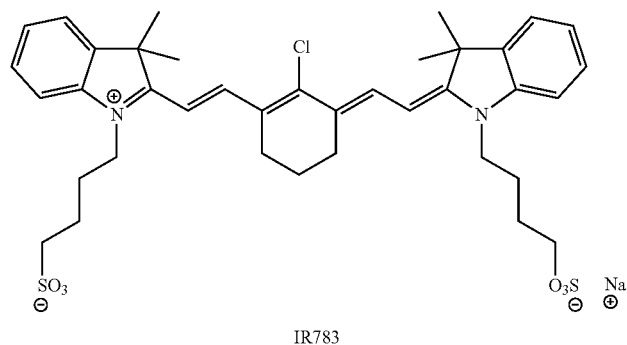

IR783

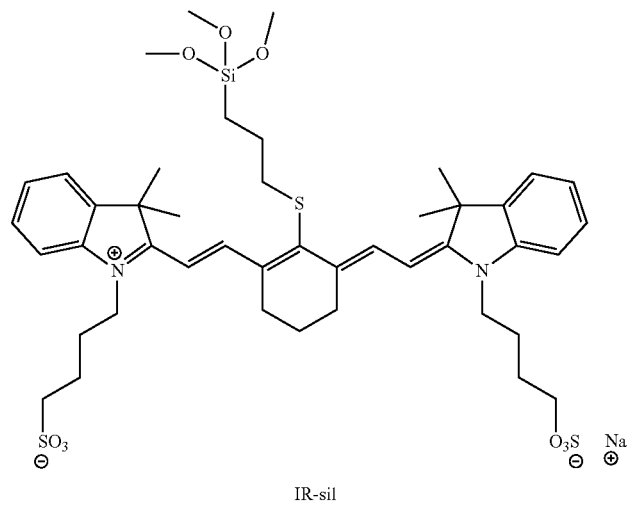

IR-sil

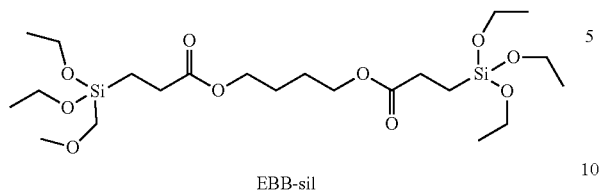

EBB-sil

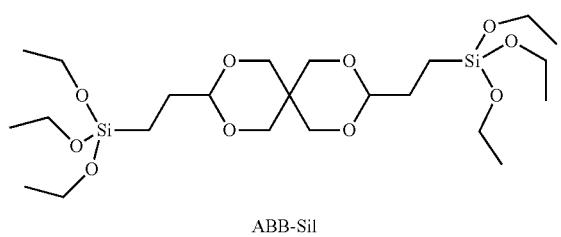

ABB-Sil

To a solution of 1,4-butanediol diacrylate (1 g, 5.05 mmol) in 10 mL benzene (anh), was added triethoxysilane (2.4 mL, 13.2 mmol) followed by addition of platinum(0)-1,3-divinyl-1,1,3,3-tetramethyldisiloxane complex solution (150 µL in xylene, Pt ~2%) as catalyst under the protection of $N_2$. The resulting mixture was stirred at 50° C. for 12 h. After the reaction mixture was cooled to RT, benzene was added. The solution was then quickly passed through silica gel for filtration. The filtrate was reduced under vacuum to remove solvent and low boiling point contaminates. The residue was dried to give the product (2.4 g, 90%). $^1$H NMR (CDCl$_3$, 500 MHz): δ 4.08 (t, 4H, OCH$_2$), 3.86 (q, 12H, SiOCH$_2$), 2.31 (q, 4H, CH$_2$C(O)), 1.69 (m, 4H, CH$_2$), 1.22 (t, 18H, CH$_3$), 1.12 (t, 4H, SiCH$_2$). $^{13}$C NMR (CDCl$_3$, 500 MHz): δ 174.73, 64.28, 59.45, 27.77, 25.61, 18.20, 9.33. ESI: 565, [M+H]$^+$.

1.8. Synthesis of Acetal Bond Bridged Silane (ABB-sil)

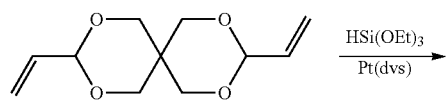

To a solution of 3,9-divinyl-2,4,8,10-tetraoxaspiro[5.5]undecane (1 g, 4.7 mmol) in 10 mL benzene (anh), was added triethoxysilane (2.1 mL, 11.6 mmol) followed by addition of platinum(0)-1,3-divinyl-1,1,3,3-tetramethyldisiloxane complex solution (150 µL in xylene, Pt ~2%) as catalyst under the protection of $N_2$. The resulting mixture was stirred at 50° C. for 12 h. After the reaction mixture was cooled to RT, benzene was added. The solution was then quickly passed through silica gel for filtration. The filtrate was reduced under vacuum to remove solvent and low boiling point contaminates. The residue was dried to give the product (2.4 g, 93%). $^1$H NMR (CDCl$_3$, 500 MHz): δ 4.38 (t, 2H, OCH), 3.82 (q, 12H, SiOCH$_2$), 3.53 (q, 4H, CH$_2$O), 3.32 (d, 4H, CH$_2$O), 1.69 (m, 4H, CH$_2$), 1.20 (t, 18H, CH$_3$), 0.70 (t, 4H, SiCH$_2$). $^{13}$C NMR (CDCl$_3$, 500 MHz): δ 103.92, 70.79, 58.74, 32.63, 28.25, 18.50, 4.15. ESI: 541, [M+H]$^+$.

1.9. Synthesis of Rhodamine β Isothiocyanate (RITC) Containing Silane (RTIC-sil)

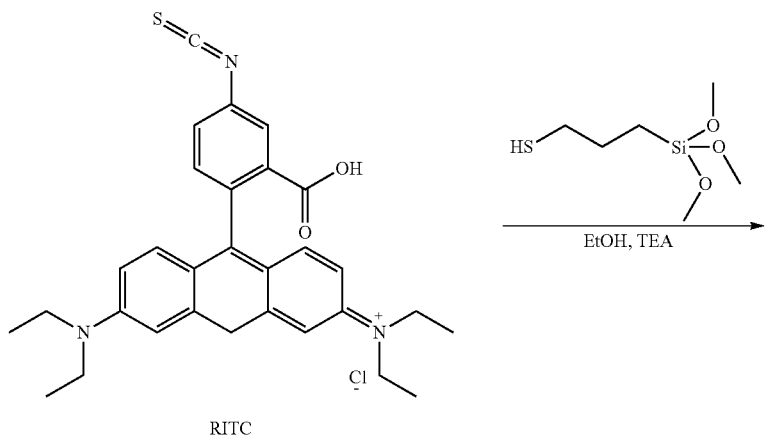

RITC

-continued

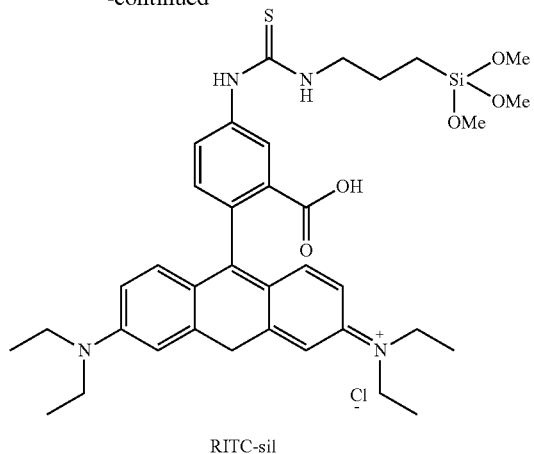

RITC-sil

In a reaction vial containing 3-aminopropyltrimethoxysilane (30 mg, 0.173 mmol) was added an anhydrous ethanol solution (1 mL) of RITC (17 mg, 0.032 mmol) and triethylamine (14.5 mg, 0.144 mmol). The reaction mixture was stirred for 12 h in nitrogen at 50° C. in the dark. The solvent and unreacted triethylamine was removed by vacuum to give RITC-sil, which was used directly without further purification.

2. Preparation of Drug Conjugated Silica NPs 2.1. Preparation of Pyr-OH conjugated silica NPs (Pyr-NPs) via the Stöber method (see Kim et al., *Biomacromolecules* 8, 215-222 (2007), and Ha et al., *Chem. Commun.*, 2881-2883 (2009) for related techniques). For the preparation of 200 nm Pyr-OH conjugated silica NPs, 1 mL methanol, 0.27 mL DI water and 0.24 mL concentrated ammonia were mixed. Then 62.5 µL TEOS was added to the mixture, which was stirred gently for 24 h. An additional 62.5 µL TEOS was added to the mixture followed by the addition of 2 mg Pyr-sil in 20 µL DMSO solution. The mixture was stirred gently (stirring rate was 100 rpm) at RT for 12 hours. The NPs were collected by centrifugation at 13.2 K rpm and washed by ethanol (1 mL) three times. The NP sizes and shapes were characterized by SEM at 5 kV. One drop of a dilute sample of silica NPs in ethanol was placed onto a silicon wafer and was allowed to dry in air. Size analysis was performed on captured digital images manually. Fabrication of monodisperse Pyr-NCs with other sizes was similarly achieved by tuning the concentrations of TEOS, water and ammonia (Table 1 in the Detailed Description above summarizes the conditions used for the preparation of silica NPs of various sizes). Representative SEM images are shown in FIG. 2.

2.2. Preparation of CPT conjugated silica NPs (CPT-NPs) via a modified Stöber method (see Corma et al., *Angew. Chem.*, Int. Ed. 48, 6247-6250 (2009) for related techniques). Silica NPs of various sizes was first prepared using Stöber method described in Section 2.1 above without adding Pyr-sil. Prepared NPs (4.1 mg) were redispersed in a mixture of 0.7 mL EtOH and 0.2 mL DI water followed by addition of 1.7 mg CPT-sil in 100 µL DMSO solution. After the mixture was stirred for 10 min to be homogenized, 25 µL NaF solution in water (10 mg/mL) was added. The pH of this mixture was approximately 7. The supernatant of the mixture was monitored by HPLC to quantify the unreacted drugs to determine the incorporation efficiency of drugs to NPs. CPT-conjugated silica NPs were thus prepared with controlled size, high drug incorporation efficiency and high drug loading. Table 3 in the description above summarizes the NP size, incorporation efficiency, and drug loading data obtained from the prepared NPs.

Drug loading was calculated based on the feeding ratio of drugs and incorporation efficiency (based on complete TEOS hydrolysis). The NPs were collected by centrifugation at 13.2 K rpm and the supernatant was removed. The isolated NPs were washed by ethanol (1 mL) three times and redispersed in DI water or 1×PBS buffer before use.

2.3. Surface PEGylation of silica nanoparticles (NPs). Silica NPs were prepared as described in Section 2.1 and 2.2. After reaction, without isolating the NPs, surface modification was carried out by directly adding a methanol solution of mPEG$_{5k}$-sil (10 mg/mL) at a weight ratio of PEG$_{5k}$-sil/NP=5/27.5. The mixture was stirred for another 12 h. Surface modified NPs were collected by centrifugation at 13.2 k rpm and the supernatant was removed. The isolated NPs were washed by ethanol (1 mL) three times and redispersed in DI water or 1×PBS buffer before use. The preparation of Ptxl-NC was similar except for addition of Ptxl-sil (1.0 mg).

2.4. Rhodamine labeling of silica NPs (RITC-NPs). Trimethoxysilane modified by rhodamine B isothiocyanate (RITC) was prepared from 3-aminopropyltrimethoxysilane and rhodamine B isothiocyanate. In a reaction vial, 30 mg (0.173 mmol) 3-aminopropyltrimethoxysilane was added to 17 mg of the fluorophore RITC (0.032 mmol) in a medium of 1 mL anhydrous ethanol with 14.5 mg triethylamine (0.144 mmol). The reaction proceeded for 12 h at 50° C. in the dark with magnetic stirring, under nitrogen. Solvent and triethylamine was removed by vacuum and the crude product (RITC-sil) was prepared in methanol at 10 mg/mL for direct use.

Silica NPs (27.5 mg) were prepared as described in Section 2.1 without adding Pyr-sil. After reaction, without isolating the NPs, fluorescence labeling was carried out by directly adding a methanol solution of RITC-sil (10 mg/mL, 100 µL). The mixture was stirred for another 12 h. Rhodamine labeled NPs were collected by centrifugation at 13.2 K rpm and the supernatant was removed. The isolated NPs were washed by ethanol (1 mL) for three times and redispersed in DI water or 1×PBS buffer before use.

2.5. IR dye (IR783) labeling of silica NPs (IR-NPs). Silica NPs (27.5 mg) were prepared as described in Section 2.1 without adding Pyr-sil. After reaction, without isolating the NPs, IR dye labeling was carried out by direct adding methanol solution of IR-sil (10 mg/mL, 100 µL). After 6 h, mPEG$_{5k}$-sil (10 mg/mL, 100 µL) was added. The mixture was stirred for another 12 h. IR dye labeled NPs were collected by centrifugation at 13.2 K rpm and the supernatant was removed. The isolated NPs were washed by ethanol (1 mL) three times and redispersed in DI water or 1×PBS buffer before use.

2.6. Preparation of Cpt- or Ptxl-silica NCs using degradable silane EBB-sil or ABB-sil via a reverse micro-emulsion process. During the NC fabrication through the reverse micro-emulsion process, Triton X-100 and n-hexanol were employed as the surfactant and the co-surfactant, respectively. To prepare 20-nm Cpt-NCs containing degradable ester bond (Cpt-EB20, Table 3), cyclohexane (7.5 mL), n-hexanol (1.8 mL) and Triton X-100 (1.77 mL) were mixed and stirred for 20 min DI water (480 µL) and EBB-sil (80 µL) were added over the course of 20 minutes Ammonia hydroxide (28%, 60 µL) was added to initiate the reaction. After 24 h, Cpt-S-sil (17.9 mg, 0.03 mmol) in dichloromethane solution (500µ) was added. The reaction solution was stirred for another 12 h. A methanol solution of PEG-sil (10 mg/mL, 600 µL) was added. The supernatant of the mixture was analysed by HPLC to quantify the unreacted Cpt-S-sil in order to determine the incorporation efficiency of drugs to NCs. The drug loading was determined based on the feed ratio of Cpt-S-sil versus EBB-sil and TEOS, and the incorporation efficiency of Cpt-S-sil to NC. The emulsion was disrupted by the addition of 10-mL ethanol. The NC (Cpt-EB20) was collected by centrifugation at 15 k rpm and washed with ethanol (3×1 mL). Cpt-EB50, Cpt-AB20 and Ptxl-EB20 (entries 23-26, Table 3) were prepared by following similar condition as summarized in Table 3.

3. In Vitro Experiments 3.1. Stability of PEGylated silica NPs in PBS (1×). PEGylated silica NPs (1.5 mg, as described in Section 2.3) were dispersed in 2 mL 1×PBS. The hydrodynamic diameter (which is 30 nm larger than the diameter of the hard cores of NPs measured by SEM) of NPs were measured by DLS and followed for 4 hours. Non-PEGylated NPs were measured similarly as the control.

3.2. Release kinetics study. CPT-NPs with size of 50 nm or 150 nm were prepared using modified Stöber method as described in Section 2.2. CPT-NPs were dispersed in 1×PBS (1.5 mg/mL) and incubated at 37° C. At schedule times, the NPs were centrifuged down at 13.2 K rpm and the supernatant was collected. After the samples were acidified to 8.5% H$_3$PO$_4$, they were injected into HPLC (RP-HPLC column, Luna C18, 250×4.6 mm, 5µ, Phenomenex, Torrance, Calif.) to quantify the released CPT at 370 nm. The precipitated NPs were redispersed in 1×PBS at the same concentration and incubated at 37° C. for the measurement of next time point. The accumulative release of CPT is shown in FIG. 3 (right graph). Similar release kinetics studies were performed in 1×PBS containing 17 U/mL esterase (Sigma-Aldrich, E3019, esterase from porcine liver).

3.3. In vitro toxicity (MTT assay). LNCaP prostate adenocarcinoma cell lines were obtained from ATCC (Manassas, Va., USA). Cells were seeded in 96-well plates at 5,000 cells/well and grown in medium containing 10% fetal bovine serum at 37° C. for 24 h in a humidified 5% CO$_2$ atmosphere. The medium was replaced with fresh medium containing CPT, CPT-NPs in concentrations ranging from 1 nM to 10 µM of CPT or equivalent CPT (CPT-NPs). At each concentration, six wells per plate were treated. The effect of the compounds on cell growth was measured by the MTT assay after 96 h. The medium was removed, the cells were rinsed with PBS, MTT solution was added at a concentration of 0.5 mg/mL, and the plates were incubated for 4 hours at 37° C. The medium was removed and the formazan crystals were solubilized in MTT solubilization solution. Absorbance was measured at 560 nm using a Victor V microplate reader (Perkin Elmer, Waltham, Mass.). The percentage of cell survival was calculated relative to untreated cells, and IC50 values were determined from plots of cell survival versus dose (Table 4).

3.4. Cellular internalization study. The HeLa cell line was used to investigate the uptake of RITC labeled silica NPs of various sizes. HeLa cells (10,000) were seeded in a 4-well chamber slide for 24 h (37° C., 5% CO$_2$). Cells were washed once with opti-MEM. Cells were then incubated for 1 h (37° C., 5% CO$_2$) with opti-MEM (1 ml) containing 100 µg/ml RITC-NPs. The cells were then washed by PBS (1 mL) for three times. Cells were then fixed with 4% paraformaldehyde and subsequently imaged on a 37° C. with confocal laser scanning microscope. Control samples without nanoparticle addition were also imaged.

For kinetics studies of cell uptake, HeLa cells (100,000) were seeded in a 12-well plate for 24 hours and RITC-NPs (100 µg/mL) were incubated with cell in opti-MEM (1 mL) over a time course ranging from 30 minutes to 1.5 hours (37° C., 5% CO$_2$). The cells were then washed by PBS (1 mL) three times and detached by trypsinization. Cells were then fixed with 4% paraformaldehyde for flow cytometry analysis for red fluorescence. Ten thousand cells were measured in each sample. Both percentage of fluorescent cells and mean fluorescence were quantified. The percentage of fluorescence positive cell population versus total live cell population was quantified by flow cytometry. A standard for fluorescence positive cells was set such that 5% of untreated cells were considered positive cells.

4. Ex Vivo and in Vivo Experiments 4.1. Animal and Tumor Model. C57BL/6 mice (female) and Balb/c nude mice (male) were purchased from Charles River, USA. Feed and water was available ad libitum. The study protocol was reviewed and approved by the Animal Care and Use Committee of University of Illinois at Urbana Champaign. For the ex vivo tumor penetration study, C57BL/6 mice were injected subcutaneously in the right flank with 1×10$^6$ LLC cells suspended in a 1:1 mixture of HBS buffer and matrigel (BD Biosciences, Franklin Lakes, N.J., USA). Prior to use in tumor induction, LLC cells were cultured in DMEM medium containing 10% FBS (Fetal Bovine Serum), 1000 units/mL aqueous Penicillin G and 100 µg/mL streptomycin. For the in vivo tumor penetration study, similarly, C57BL/6 mice were injected subcutaneously in the right flank with 10×10$^6$ EL4 cells suspended in a 1:1 mixture of HBS buffer and matrigel. For the in vivo biodistribution study, human xenograft prostate cancer tumors were induced in 8-week old Balb/c nude mice. Mice were injected subcutaneously in the right flank with 4×10$^6$ LNCaP cells suspended in a 1:1 mixture of HBS buffer and matrigel.

4.2. Ex vivo Tumor Penetration Study. Twelve to thirteen week old, female C57BL/6 mice bearing LLC tumors were sacrificed to harvest the tumors when the tumors grew to a size of ~6.7 mm×8.0 mm Tumors (n=3, three mice for each group) were ex vivo cultured with silica NPs 20 nm, 50 nm or 200 nm in diameter with IR783 labeling at concentration of 3 mg/mL NP in cell medium for 48 hours. Tumor without any treatment served as controls. Tumor sections (20 µm in thick) were collected by cryostat and mounted on glass slides. Fluorescence images were taken by Zeiss Axiovert 200M fluorescence microscope with 780 nm laser excitation. A tiling image was taken with fixed exposure time to show the NP penetration in tumor sections. Plot profile of fluorescence in tumor sections was analyzed by Image J.

4.3. In vivo Tumor Penetration Study. LLC tumor-bearing C57Bl/6 mice were divided randomly into groups of three and were treated when the mean tumor diameter was in the range 5 to 6 mm Animals received 0.2 mL of 50 mg/mL rhodamine labeled silica NPs with different sizes (20, 50, or 200 nm in diameter). Animals were killed and tumors excised at 24 hours following injection. Tumors were collected and fixed in 10% formalin and then embedded in paraffin prior to tissue sectioning and immunohistochemical staining. Tissue sections measuring 5 μM in thickness were cut from each tumor, mounted on glass slides, and allowed to air-dry. Fluorescence was detected using a Zeiss LSM 700 confocal microscope with four laser point scanning Tissue sections were imaged with a 10×/0.3 lens. Developing tumor neovasculature within each tumor section was identified by the expression of Von Willebrand Factor (Factor VIII-related antigen) by incubating slides with a rabbit polyclonal anti-human Factor VIII antibody (1:200) for 30 minutes at room temperature. Following primary antibody incubation, glass slides were stained with a FITC-conjugated goat polyclonal anti-rabbit antibody (1/250) for 4 hours in the dark, then coverslipped using VECTASHIELD mounting media (Burlingame, Calif.). FITC fluorescence representing endothelial cells was visualized using 488 nm laser excitation. Rhodamine fluorescence, representing silica nanoparticles, was visualized with 555 nm excitation. See FIG. 15.

4.4. In vivo Biodistribution Study.

A. Balb/c nude mice bearing LnCaP tumor (size: ~12 mm×12 mm) were divided into groups of two, minimizing tumor size variations between groups. Mice were injected intravenously with IR783-labeled silica NPs, 50 or 200 nm in diameter, at a dose of 150 mg/kg. Mice were euthanized 24 hours post injection, fixed in 10% formalin. Whole body images were taken by Odyssey infrared imaging system at 800 nm. Mouse organs (tumor, liver, spleen, and kidneys) were then harvested. The fluorescence of tissues was directly assayed using an Odyssey infrared imaging system. The measurements of various organs were validated using a phantom of free IR783 solution on top of tissues of various thicknesses. The thickness of each organ measured was no more than 3 mm, with >80% transmission (Table 6).

To determine a 100% dose, a diluted solution of IR783-labeled silica NPs was measured along with tissues at the same instrument settings. The percent transmission of various mouse tissues with different thicknesses for the fluorescence measurements by an Odyssey infrared mouse imaging system at the 800 nm channel (IR783) is shown above in Table 6.

B. C57Bl/6 mice bearing LLC tumor (size: ~5 mm×8 mm) were divided into groups of three, minimizing tumor size variations between groups. Mice were injected intravenously with IR783-labeled silica NPs, 20, 50, or 200 nm in diameter, at a dose of 500 mg/kg. Mice were euthanized and dissected 24 hours post injection. Various organs were collected and fixed in 10% formalin. The fluorescence of each organ was measure ex vivo at 800 nm using an Odyssey infrared mouse imaging system. Data is presented as percent injected dose per gram of tissues. The statistical analysis was undertaken using a Student's t-test. P-values<0.05 were considered statistically significant. Data reported are average±standard deviation (see FIG. 10).

4.5. In vivo Tumor Reduction Study. Female C57Bl/6 mice, 8-week old, were anesthetized, shaved, and prepared for implantation of the tumor cells. LLC cells were collected from culture, and 1×10⁶ cells suspended in a 1:1 mixture of HBS buffer and matrigel were then injected subcutaneously into right flank of a mouse. After two weeks when tumors had reached ~300 mm³, mice were divided into five groups of five mice, minimizing weight and tumor size difference. Tumor-bearing mice were treated by intravenous injection of PBS (1×), PEGylated blank silica NPs (250 mg/kg), emulsified free CPT (Tween 80 (5%)/DMSO (10%) in PBS (1×), 30 mg/kg), CPT-NP (200 nm, 25 mg/kg) or CPT-NP (20 nm, 25 mg/kg). After dosing, the animals were monitored closely, and measurements of the tumor size for each animal were performed at regular intervals using calipers without knowledge of which injection each animal had received. The tumor volume for each time point was calculated according to the formula (length)×(width)²/2, where the long axis is the length, the short axis is the width. If body weight loss was beyond 20% of pre-dosing weight, the animals were euthanized. When the tumor load reached 2000 mm³ or the animal had become moribund, the mouse was sacrificed. The statistical analysis was undertaken using a Student's t-test (two-tailed), and p-values<0.05 were considered statistically significant. Median tumor growth curves prepared for each group depicted the median tumor size as a function of time. When an animal exited the study due to tumor size or treatment related death, the final tumor size recorded for the animal was included with the data used to calculate the mean size at subsequent time point.

Example 2

Nanocomposite Release Kinetics

Figure 16:
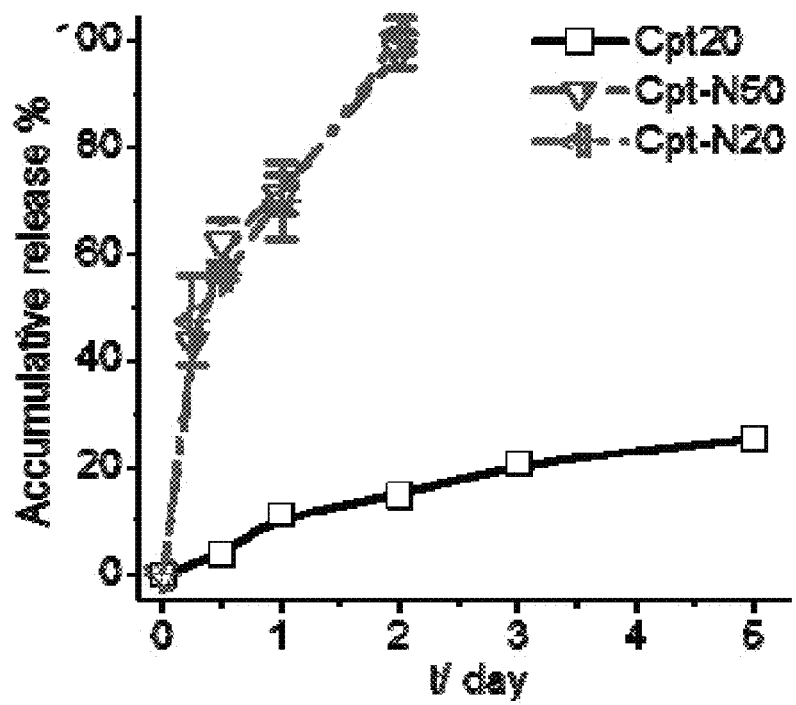
FIG. 16. Release kinetics of Cpt-NCs with different sizes and linkers between drug and NC, in 50% human serum at 37° C.

Drug burst release is a long-standing formulation challenge of nanocarriers with drugs encapsulated in polymeric nanoparticles (NPs) or adsorbed in mesoporous silica NPs. The drug burst causes undesirable dose dumping, significant side effects, and reduced long-term therapeutic efficacy. Because the drug release kinetics of drug-NCs such as the Cpt-S-sil described herein is determined by the hydrolysis of the thioether ester bond linker, the release kinetics of drug from NCs are more controllable and have essentially no burst release (FIG. 16). In human serum, Cpt-S-sil (Cpt20 in FIG. 16) with the hydrophobic thioether ester linker between Cpt and the silica particles showed sustained drug release with 14.8% of CPT being released in 48 hours (FIG. 16). The $IC_{50}$ value of Cpt20 in HeLa cells was found to be 220 μM. When the linker was changed to a hydrophilic amine ester as in Cpt-N20 (entry 12, Table 3), which was prepared by using Cpt-NH-sil as the corresponding drug-containing silane reagent (FIG. 1b), the Cpt release kinetics can be dramatically accelerated with Cpt being 100% released within 48 hours, resulting in a much lower $IC_{50}$ value (9.0 nM). By controlling the feed ratio of Cpt-S-sil/Cpt-NH-sil during Cpt-NC fabrication to the ratios of these two different linkers, the Cpt release half-life can be precisely adjusted ranging from 24 hours to about two weeks.

Experimental Details.

The NC (Cpt20, Cpt-N20 or Cpt-N50) was dispersed in 50% reconstituted human serum (Sigma-Aldrich) (0.6 mg/mL), equally distributed to 20 vials with 1 mL NC solution per vial, and then incubated at 37° C. At selected time intervals, one selected vial of each group was taken out of the incubator. The NC solution was mixed with equal volume of methanol (1 mL) and centrifuged at 15,000 rpm for 10 min. The supernatant (1 mL) was transferred to an Eppendorf tube without disturbing the precipitates (NCs) and tuned to pH 2 with phosphoric acid (85%, 100 µL). The resulting solution was directly injected into HPLC equipped with an analytical C18 column (Luna C18, 250×4.6 mm, 5µ, Phenomenex, Torrance, Calif., USA). A mixture of acetonitrile and water (containing 0.1% TFA) at a volume ratio of 1:3 was used as the mobile phase. The flow rate was set at 1 mL/min. The area of the HPLC peak of the released Cpt ($\lambda_{abs}$=370 nm) was intergraded for the quantification of Cpt as compared to a standard curve of free Cpt prepared separately.

Example 3

Gram Scale Preparation of Drug Conjugated Particles

Besides controlled particle size, drug loading and release kinetics, other issues critical to the clinical translation of NP drug delivery system must be addressable, such as scalability, lyophilizability, and toxicity. These issues can present bottlenecks to the clinical translation of nanomedicines. In this example, silica NPs were used to investigate the relationship between cyroprotectants and final NP sizes.

Figure 17:
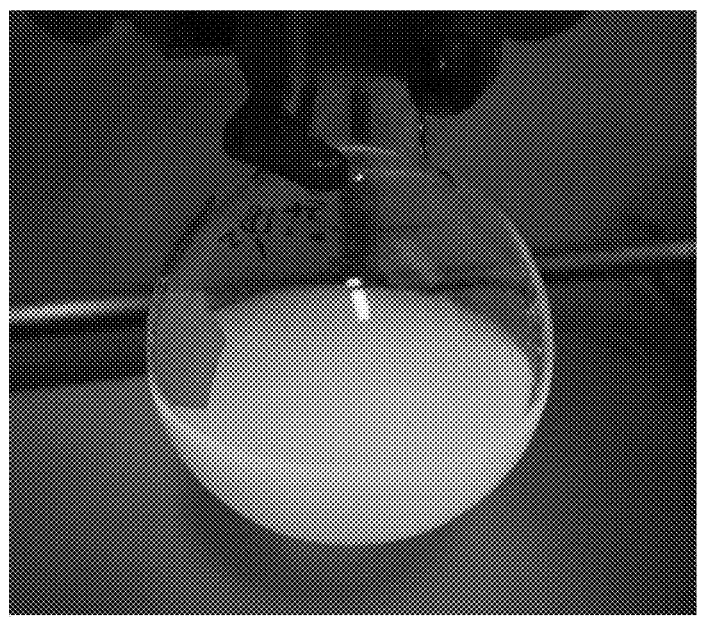
FIG. 17. A photo of a reaction flask of a gram scale preparation of Cpt50.

Fabrication methods described herein can be readily used for the large-scale preparation of NCs (FIG. 17). The preparation of one gram of 50-nm Cpt-NC in one pot provided NCs with the expected size (46.4±4.6 nm) were successfully obtained in quantitative yield within one day (entry 28, Table 3 above). The NP fabrication process that allows preparation of very small drug delivery NPs with remarkable control over size and monodispersity and with excellent scalability is unprecedented and offers clear advantages over other delivery NP preparation methods.

Lyophilization of Silica NPs in the Presence of Lyoprotectants.

Aiming to formulate solid silica NCs without aggregation, the lyophilization of silica NCs was tested in the presence of various lyoprotectants (Table 3-1 below).

TABLE 3-1

Lyoprotectant Mediated Silica NP Stabilization During Lyophilization.

| Entry | Lyo-protectant | m(Lyo)/m(NP)[a] | $D_o$/nm[b] | D/nm[c] | D/$D_o$[d] | Aggr. (Y/N)[e] |
|---|---|---|---|---|---|---|
| 1 | None | N/A | 102.0 | 233.5 | 2.29 | Y |
| 2 | Sodium chloride | 10 | 102.0 | 2295.1 | 22.50 | Y |
| 3 | BSA | 1 | 102.0 | 139.1 | 1.36 | N |
| 4 | BSA | 5 | 102.0 | 120.6 | 1.18 | N |
| 5 | BSA | 10 | 102.0 | 142.0 | 1.39 | N |
| 7 | Dextrose | 1 | 102.0 | 108.1 | 1.06 | N |
| 8 | Dextrose | 5 | 102.0 | 101.5 | 1.00 | N |
| 9 | Dextrose | 10 | 102.0 | 99.5 | 0.98 | N |
| 10 | None | N/A | 69.8 | 558.8 | 8.01 | Y |
| 11 | Sodium chloride | 10 | 69.8 | 2910.7 | 41.70 | Y |
| 12 | BSA | 1 | 69.8 | 103.6 | 1.48 | N |
| 13 | BSA | 5 | 69.8 | 91.0 | 1.30 | N |
| 14 | BSA | 10 | 69.8 | 97.8 | 1.40 | N |
| 15 | Dextrose | 1 | 69.8 | 84.3 | 1.21 | N |
| 16 | Dextrose | 5 | 69.8 | 68.9 | 0.99 | N |
| 17 | Dextrose | 10 | 69.8 | 71.2 | 1.02 | N |

[a]Weight ratio of lyoprotectants to NPs.
[b]Original hydrodynamic diameter in nm of the NP measured by DLS.
[c]Hydrodynamic diameter in nm of the NP post lyophilization measured by DLS.
[d]Ratio of NP diameters after lyophilization to original diameter.
[e]The NPs aggregated (Y) or did not aggregate (N), ocular inspection post lyophilization.

Figure 18:
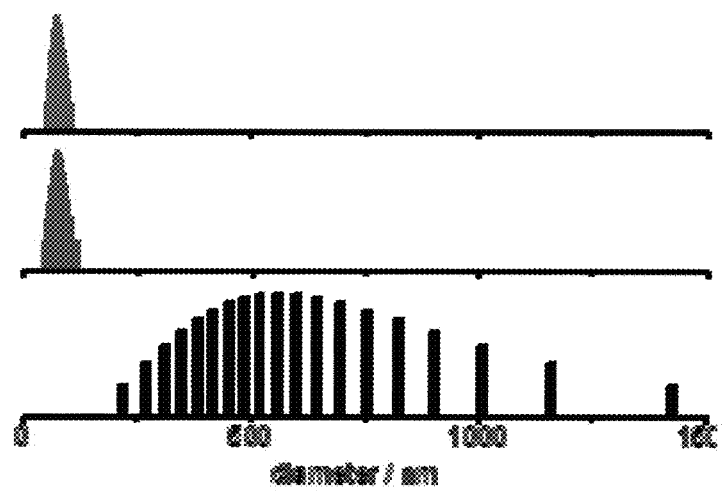
FIG. 18. NC size distributions measured by dynamic light scattering (DLS) before lyophilization (top), after lyophilization in the presence of dextrose (5%) and reconstituted with water (middle), and after lyophilization in the absence of dextrose and reconstituted with water (bottom).

The NPs were prepared via Stöber method. After NP formulation, various lyoprotectants were added and the mixture was subject for lyophilization. BSA: bovine serum albumin (from Fisher). No lyoprotectant was added for Entries 1 and 10. Dextrose was found to be a highly effective lyoprotectant for silica NCs. Silica NCs lyophilized in 1 mL of a 5% dextrose solution (known as D5W, routinely used for drug administration in clinical settings) resulted in the solid formulation of silica NCs with essentially no change of particle sizes after lyophilization and re-constitution in water (FIG. 18).

Experimental Details.

Silica NPs were prepared at TEOS/PEG-sil ratio (wt./wt.) of 19.6:1 using the Stöber method as described previously (St-B and St-D) and analysed with DLS. Various lyoprotectants (Table 3-1) were added at different lyoprotectant/NP ratio (varying from 1:1 to 10:1 wt./wt.) to the NP solution and the solution was lyophilized. The solid-form silica NP/lyoprotectant was reconstituted with 2-mL DI water to provide a NP aqueous solution at a concentration of 10 mg/mL. The reconstituted silica NPs were analysed by DLS (FIG. 18). The silica NP lyophilized in the absence of lyoprotectant and reconstituted with water was used as the negative control.

A gram-scale preparation of 50 nm Cpt conjugated silica NPs (with 1% loading of Cpt) was also be carried out as follows. Methanol (15 mL), 5.40 mL DI water and 1.35 mL concentrated ammonia were mixed. TEOS (939 µL) was added to the mixture, which was stirred gently for 5 hours. A solution of Cpt-S-sil (8.4 mg) in 500 µL DMSO was added to the mixture. The mixture was stirred gently (100 rpm) at room temperature (~23° C.) for 12 hours. The NPs were collected by centrifugation at 15 k rpm and washed by ethanol for three times. The NP sizes and shapes were characterized by Scanning Electron Microscopy (SEM).

Example 4

Therapeutic Methods for the Treatment of Lung Cancer

To access the ability of Cpt-NCs to prevent establishment of a murine lung cancer in an in vivo model, Cpt-NCs were evaluated in the rapidly growing subcutaneous (s.c.) LLC tumor model in C57Bl/6 female mice. The ability of Cpt50 (5 mg/kg) to prevent LLC tumor establishment and growth was assessed by comparing to free Cpt (5 mg/kg) and LLC cancer cells alone without any treatment. The mice were s.c. injected with the mixture of [LLC and Cpt50], [LLC and Cpt] or LLC alone Animals were monitored clinically and the tumors were measured daily without knowledge of the treatment received.

Figure 19:
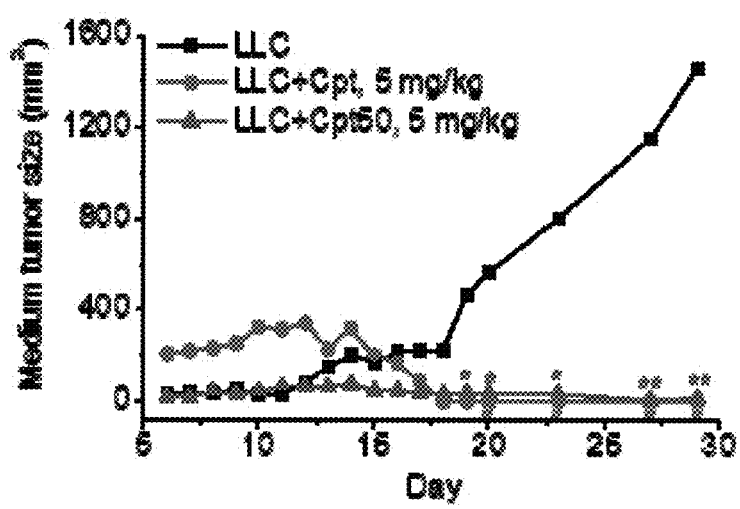
FIG. 19. Tumor growth inhibition and prevention by Cpt-NC. LLC tumor growth over time for C57Bl/6 mice receiving different treatments were monitored. Data is displayed as mean of tumor size. Statistical analysis by T-Test (two tail, *p<0.05, **p<0.01).

As shown in FIG. 19, large tumors were noted where LLC were injected alone. Both Cpt and Cpt50 showed clearly the ability of tumor growth prevention with complete inhibition of tumor growth after Day 20. Statistically significant difference was observed at Day 19 when comparing [LLC+Cpt50] group with the LLC group indicating the start of tumor inhibition from Day 19. Higher significance were observed at Day 27 and 29 (**p<0.01, two tailed t-test). However, statistically significant difference between [LLC+Cpt] group and LLC group was found even at Day 20. This result reveals that Cpt50 has better ability to prevent tumor growth comparing with free Cpt due to its better tumor retention and sustained release profile of the drug.

Figure 20:
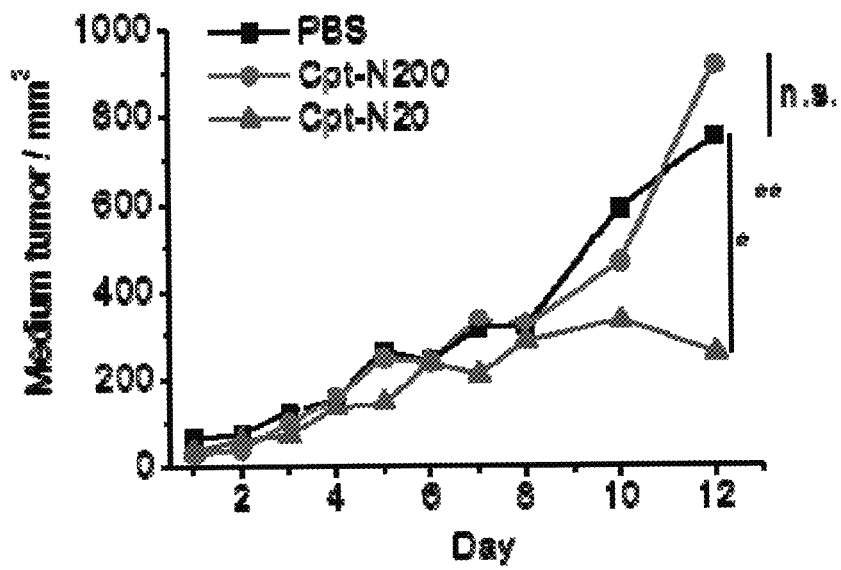
FIG. 20. Delay and inhibition of LLC tumor growth for C57Bl/6 mice with treatment of Cpt-silica nanoconjugates (Student T-test (two-tailed): n.s., not significant; 0.01<*p≤0.05; **p≤0.01). Three doses were administered on Day 1, Day 5 and Day 9.

The antitumor efficacy of Cpt-NCs prepared with Cpt-NH-sil was also evaluated using subcutaneous LLC tumor model on the flank of C57BL/6 mice (FIG. 20). Mice treated with Cpt-N20 (three doses every four days, 40 mg/kg) showed the delay of tumor growth with statistical significance as compared with mice treated with PBS buffer as control (*p<0.05, two tailed t-test). However, Cpt-N200 did not show any efficacy as compared with PBS group. Cpt-N20 clearly outperformed Cpt-N200 due to its smaller size for enhanced tumor targeting and penetration as demonstrated.

Experimental Details.

In Vivo Tumor Prevention Study.

Female C57Bl/6 mice, 12-13 weeks old, were anesthetized, shaved, and prepared for implantation of the tumor cells. LLC cells were collected from culture, and 750,000 cells were then mixed with Cpt50 and immediately injected subcutaneously into one flank of a mouse. The dose of equivalent Cpt was 5 mg/kg. Equivalent injections of cells with free CPT solubilized with Tween 80 (5%)/DMSO (10%) or PBS were also performed (n=5). The simultaneous injection procedure is required to assure that the cancer cells and the treatment are delivered to the same subcutaneous pocket as it would be easy to accidentally inject into different spaces when performing two separate injections. The ability of the tumor cells to attach and grow in the subcutaneous space was demonstrated by the untreated control. The animals were monitored closely, and measurements of the tumor size for each animal were performed at regular intervals using calipers without knowledge of which injection each animal had received. The tumor volume for each time point was calculated according to the formula (length)×(width)$^2$/2, where the long axis is the length, the short axis is the width. When the tumor load reached 2000 mm3 or the animal had become moribund, the mouse was sacrificed.

In Vivo Tumor Reduction Study.

Female C57Bl/6 mice, 8-week old, were anesthetized, shaved, and prepared for implantation of the tumor cells. LLC cells were collected from culture, and 1×10$^5$ cells suspended in a 1:1 mixture of HBS buffer and matrigel were then injected subcutaneously into right flank of a mouse. After two weeks when tumors had reached ~40 mm$^3$, mice were divided into three groups of five mice, minimizing weight and tumor size difference. Tumor-bearing mice were treated by intravenous injection of PBS (1×), Cpt200 (40 mg/kg) or Cpt20 (40 mg/kg). After dosing, the animals were monitored closely, and measurements of the tumor size for each animal were performed at regular intervals using calipers without knowledge of which injection each animal had received. The tumor volume for each time point was calculated according to the formula (length)×(width)/2, where the long axis is the length, the short axis is the width. If body weight loss is beyond 20% of pre-dosing weight, the animals were euthanized. When the tumor load reached 1000 mm$^3$ or the animal had become moribund, the mouse was sacrificed. The statistical analysis was undertaken using a Student's t-test (two-tailed), and p-values<0.05 were considered statistically significant. Median tumor growth curves prepared for each group depicted the median tumor size as a function of time. When an animal exited the study due to tumor size or treatment related death, the final tumor size recorded for the animal was included with the data used to calculate the mean size at subsequent time point.

Example 5

Therapeutic Methods for the Treatment of Breast Cancer

To further study the effect of particle size, a xenograft human breast cancer model was chosen. Subcutaneous MCF-7 tumors developed on the flank of athymic nude mice were used to evaluate the antitumor efficacy of the drug-silica nanoconjugates with different sizes. The nude mice were implanted with an estrogen pellet and 1,000,000 MCF-7 cells per site. After tumors had developed to ~40 mm$^3$, comparative efficacy studies were performed by dividing animals into six groups (n=20 or 24) to minimize weight and tumor size differences among the groups.

Using Cpt as a reference point, the following regimens were administrated by i.v. injection: 1) PBS; 2) PEGylated blank silica NPs; 3) Irinotecan (a marketed Cpt analogue), 100 mg/kg; 4) Cpt-N200, 20 mg/kg; 5) Cpt-N50, 20 mg/kg; 6) Cpt-N20, 20 mg/kg. The tumor size and body weight were then monitored for 26 days. Both Cpt-N50 and Cpt-N20 showed the effect of delaying the tumor growth as early as Day 4 (*p<0.05, One-way ANOVA, Fisher.) compared to the PBS group (FIGS. 21 and 22), while Cpt-N200 showed the efficacy started from Day 8.

Irinotecan at a five times higher dose also showed the efficacy of inhibiting tumor growth with statistical significance from Day 8 as compared with the PBS group. Significant body weight loss was also observed for the Irinotecan group (FIG. 22), which indicates sever toxicity and side effect for this treatment. However, Cpt-N50 and Cpt-N20 did not show such toxicities (FIG. 22) but exhibited comparable efficacy with Irinotecan at much lower doses. The results indicate that Cpt-N50 and Cpt-N20 can be as efficacious as Irinotecan on hormone sensitive breast tumors but with much less systemic toxicity.

Figure 21:
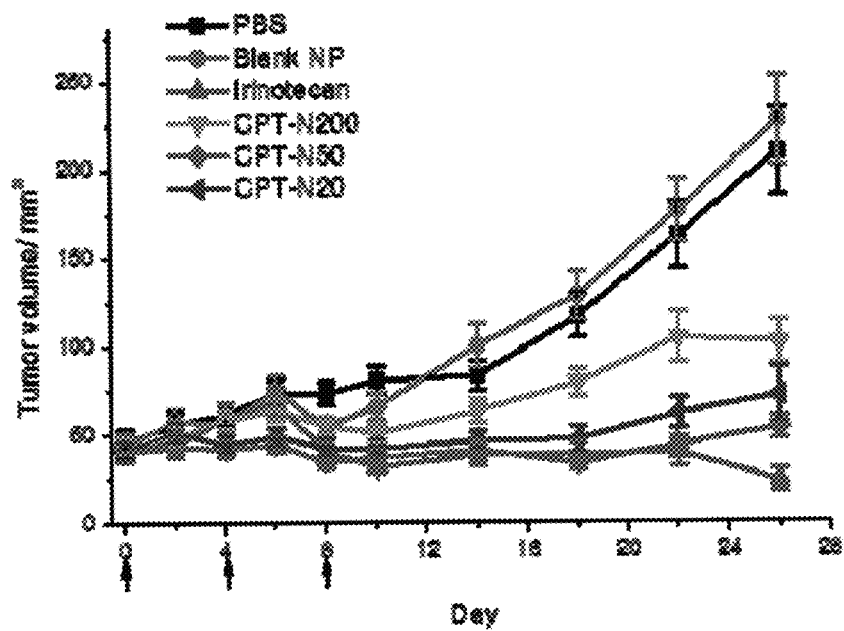
FIG. 21. In vivo antitumor efficacy studies. Delay and inhibition of MCF-7 tumor growth for athymic nude mice with treatment of Cpt-NC (Student T-test (two-tailed): n.s., not significant; 0.01<*p≤0.05; **p≤0.01). Three doses were administered, one on each of Day 0, Day 4 and Day 8.
Figure 22:
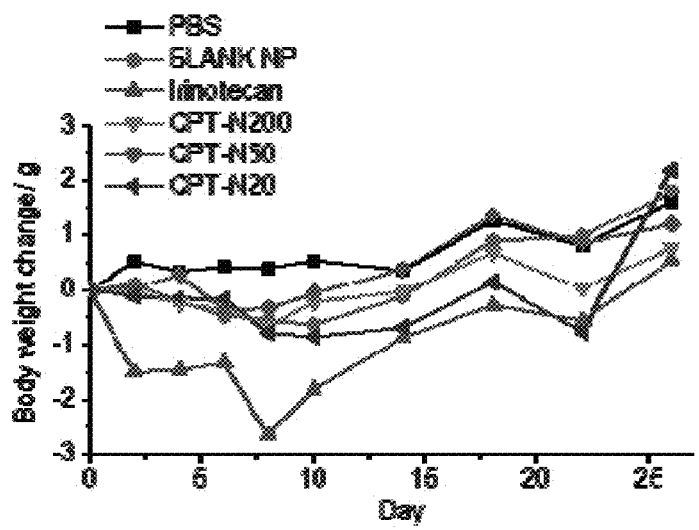
FIG. 22. Body weight change for PBS, irinotecan and Cpt-NCs with different sizes.

As observed for the LLC tumor model, Cpt-N50 and Cpt-N20 outperform Cpt-N200 in tumor growth inhibition with statistical significance. Based on the above-mentioned results, the higher efficacy of smaller drug-NCs is likely due to the more efficacious tumor targeting in vivo, enhanced tumor penetration, more efficient cell uptake and faster drug release of small NP compared to larger counterparts. There was no statistical difference between Cpt-N50 and Cpt-N20 in this study. However, final tumor size in the Cpt-N50 group was smaller than Cpt-N20 group (FIG. 21). The result showed that Cpt-N50 was slightly more efficacious than Cpt-N20, potentially because Cpt-N50 had longer circulation while Cpt-N20 was subjected to faster renal clearance due the smaller size.

Experimental Details.

In Vivo Tumor Reduction Study.

Female athymic nude, OVX, 9-week old mice were anesthetized, and prepared for implantation of the tumor cells. MCF-7 cells were collected from culture, and 1×10$^6$ cells suspended in a 1:1 mixture of HBS buffer and matrigel were then injected subcutaneously into right flank of a mouse. After two weeks when tumors had reached ~40 mm$^3$, mice were divided into six groups (n=20 or 24), minimizing weight and tumor size difference. Tumor-bearing mice were treated by intravenous (i.v.) injection (Q4d×3): a) PBS, 200 µL; b) PEGylated blank silica NPs (50 nm), equivalent SiO$_2$ as Cpt-NC groups; d) Cpt-N200 (200 nm), 20 mg/kg; e) Cpt-N50 (50 nm), 20 mg/kg; f) Cpt-N20 (20 nm), 20 mg/kg; and c) i.p. injection (Qwk×3) for group Irinotecan, 100 mg/kg.

After dosing, the animals were monitored closely, and measurements of the tumor size for each animal were performed at regular intervals using calipers without knowledge of which injection each animal had received. The tumor volume for each time point was calculated according to the formula (length)×(width)/2, where the long axis is the length, the short axis is the width. If body weight loss was beyond 20% of pre-dosing weight, the animals were euthanized. When the tumor load reached 700 mm$^3$ or the animal had become moribund, the mouse was sacrificed. The statistical analysis was undertaken using One-way ANOVA, and p-values<0.05 (Fisher) were considered statistically significant. Average tumor growth curves prepared for each group depicted the median tumor size as a function of time. When an animal exited the study due to tumor size or treatment related death, the final tumor size recorded for the animal was included with the data used to calculate the mean size at subsequent time point.

Example 6

Therapeutic Methods for the Treatment of Breast Cancer

Figure 23:
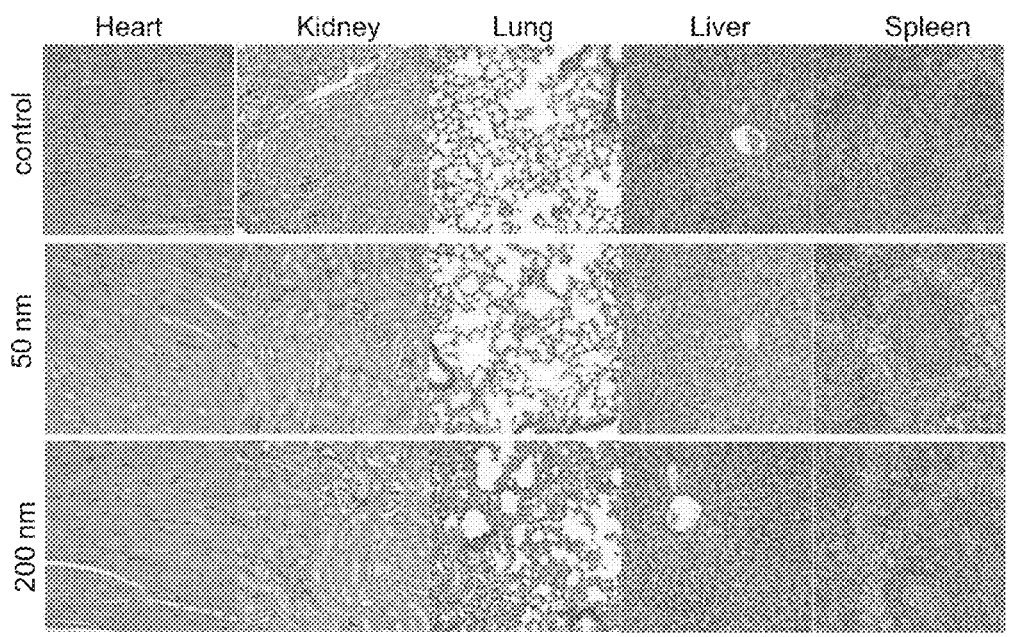
FIG. 23. Histopathology of mouse tissues following an intravenous injection of silica nanoparticles via a tail vein. Representative sections of various organs taken from control mice receiving PBS and mice receiving 250 mg/kg blank silica nanoparticles (50 nm or 200 nm in diameter) 24 h post injection. Hematoxylin and eosin stain. No organs of a mouse given silica nanoparticles showed any acute inflammations.

Recent studies showed that silica NPs can decompose in blood within a few days, indicating that this class of NPs can be eliminated by either hepatic or renal clearance, thereby minimizing concerns for cumulative tissue damage and associated toxicity. In vitro studies (MTT assay; Table 4) showed almost no toxicity of blank silica NPs ($IC_{50}$>1 mM). Acute in vivo toxicity experiments were performed after i.v. administration of 50 nm silica NPs in C57BL/6 mice at very high dose up to 250 mg/kg. There was no mortality or deterioration under general conditions observed in any of the groups. In addition, there were no treatment related clinical signs and change of body weights. Representative sections of various organs taken 24 h after injections from control mice receiving PBS and mice receiving silica NPs were stained by hematoxylin and eosin, and evaluated by an independent pathologist (FIG. 23). The absence of immune or inflammatory reactions after NC administration supports their lack of toxicity.

Experimental Details.

In Vivo Biocompatibility Study.

Silica NPs of 50 and 200 nm in diameter were prepared by St-C and St-G methods, respectively, using TEOS/6=19.6/1. They were administered intravenously (200 µL, 25 mg/mL) via lateral tail vein to the C57BL/6 mice (n=3) at a dose of 250 mg silica NC/kg. The animals were sacrificed 24 hours later by carbon dioxide. Organs including heart, lung, liver, spleen, kidney, stomach, small intestine, and large intestine were fixed in 10% neutral buffered formalin for 48 hours. The fixed tissues were then processed and trimmed, embedded in paraffin, sectioned to a thickness of 5 µm, and stained with hematoxylin and eosin for microscopic examination (FIG. 23). Characterization of all the collected target tissues for inflammatory cell infiltrate including macrophages and neutrophils were performed by systemic microscopic evaluation at 400× magnification and analysed by an independent pathologist.

Example 7

Pharmaceutical Dosage Forms

The following formulations illustrate representative pharmaceutical dosage forms that may be used for the therapeutic or prophylactic administration of a polymer or composition described herein, (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A silica nanoparticle comprising a non-porous matrix of silicon-oxygen bonds, wherein the matrix comprises organic agents conjugated to silicon or oxygen atoms in the matrix, the organic agents are located inside the surface of the nanoparticle or both inside the surface of the nanoparticle and on the surface of the nanoparticle, the organic agents are conjugated to the matrix through linker L groups, wherein the linker L comprises an ester, acetal, urea, thiourea, or thio ether group, wherein the silica nanoparticle matrix comprises responsively degradable Si-ester-Si groups, degradable Si-acetal-Si groups, or both, dispersed throughout the matrix; and wherein the diameter of the nanoparticle is about 15 nm to about 200 nm.

2. The silica nanoparticle of claim 1 wherein the organic agent is a drug, a diagnostic agent, a surface modification agent, or a combination thereof.

3. The silica nanoparticle of claim 1 wherein the silica nanoparticle degrades under physiological conditions.

4. The silica nanoparticle of claim 3 wherein the organic agent is hydrolyzed from the linker L of the silica nanoparticle with controlled release kinetics under physiological conditions.

5. The silica nanoparticle of claim 4 wherein the linker L is responsively degradable.

6. The silica nanoparticle of claim 5 wherein the surface of the nanoparticle comprises surface-modifying groups.

7. The silica nanoparticle of claim 6 wherein the surface-modifying group comprises PEG groups.

8. The silica nanoparticle of claim 2 wherein the drug is paclitaxel, camptothecin, docetaxel or doxorubicin.

9. The silica nanoparticle of claim 2 wherein the diagnostic agent is an optical imaging agent, a magnetic resonance imaging agent, or a positron emission tomography agent.

10. The silica nanoparticle of claim 2 wherein the diagnostic agent is pyrene, rhodamine B, IR783, Gd-EDTA, or $^{64}$Cu-EDTA.

11. The silica nanoparticle of claim 5 wherein the linker L comprises one or more of:

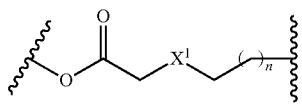

wherein n is 0-8 and $X^1$ is $CH_2$, NH, or S;

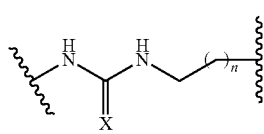

wherein n is 0-8 and X is O or S; or c) —$(C_1$-$C_8)$alkyl-S—.

12. A silica nanoparticle comprising a non-porous matrix of silicon-oxygen bonds, wherein the matrix comprises organic agents conjugated to silicon or oxygen atoms in the matrix, the organic agents are conjugated to the matrix through linker L groups, wherein the linker L comprises an ester, acetal, urea, thiourea, or thio ether group, and wherein the diameter of the nanoparticle is about 15 nm to about 200 nm; wherein the silica nanoparticle degrades under physiological conditions, the organic agent is hydrolyzed from the linker L of the silica nanoparticle with controlled release kinetics under physiological conditions, and linker L is responsively degradable;

wherein the linker L comprises one or more of:

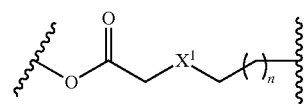

wherein n is 0-8 and $X^1$ is $CH_2$, NH, or S;

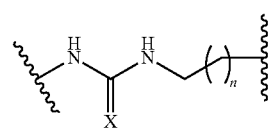

wherein n is 0-8 and X is O or S; or c) —$(C_1$-$C_8)$alkyl-S—; and wherein the silica nanoparticle matrix comprises one or more Si-ester-Si groups, Si-acetal-Si groups, or both;

wherein the Si-ester-Si group comprises a moiety of Formula I:

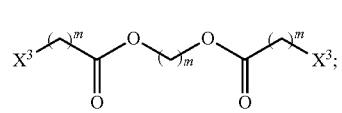

wherein each m is independently 1-8 and each $X^3$ is a silicon atom of the silica nanoparticle matrix; and wherein the Si-acetal-Si group comprises a moiety of Formula II:

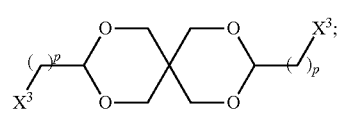

wherein each p is independently 1-8 and each $X^3$ is a silicon atom of the silica nanoparticle matrix.

13. The silica nanoparticle of claim 12 wherein the silica nanoparticle matrix comprises one or more Si-ester-Si groups, Si-acetal-Si groups, or both;

wherein the Si-ester-Si group comprises a moiety of Formula IA:

(IA)

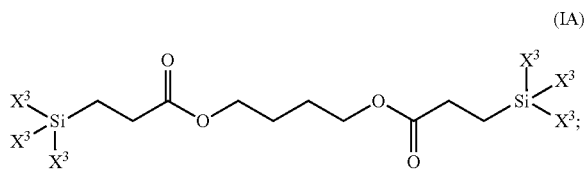

wherein each X³ is an oxygen atom of the silica nanoparticle matrix; and wherein the Si-acetal-Si group comprises a moiety of Formula IIA:

(IIA)

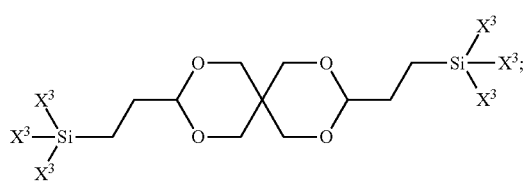

wherein each X³ is an oxygen atom of the silica nanoparticle matrix.

14. The silica nanoparticle of claim 13 wherein the diameter of the particle is about 15 nm to about 200 nm.

15. The silica nanoparticle of claim 13 wherein the diameter of the particle is about 15 nm to about 50 nm.

16. A method of enhancing the penetration of a drug into a tumor comprising administering an effective amount of a plurality of silica nanoparticles of claim 14 to a mammal that has a tumor, wherein the particles enter the tumor, and the nanoparticles release the drug to the tumor.

17. A pharmaceutical composition comprising a plurality of silica nanoparticles of claim 2 and a pharmaceutically acceptable diluent, excipient, or carrier.

18. A method for delivering a therapeutic agent to an animal in need of treatment with the agent comprising administering a plurality of silica nanoparticles of claim 2 to the animal, wherein the therapeutic agent releases from the linker L under the physiological conditions of the animal, thereby delivering the therapeutic agent to the animal.

19. A composition comprising a plurality of silica nanoparticles of claim 1 and a lyoprotectant.

20. The composition of claim 19 wherein the lyoprotectant comprises dextrose.

21. A silica nanoparticle comprising a non-porous matrix of silicon-oxygen bonds, wherein the matrix comprises organic agents conjugated to silicon or oxygen atoms in the matrix, the organic agents are conjugated to the matrix through linker L groups, wherein the linker L comprises an ester, acetal, urea, thiourea, or thio ether group, and wherein the diameter of the nanoparticle is about 15 nm to about 200 nm; the silica nanoparticle degrades under physiological conditions, and the organic agent is hydrolyzed from the linker L of the silica nanoparticle with controlled release kinetics under physiological conditions;

wherein the silica nanoparticle matrix comprises one or more Si-ester-Si groups, Si-acetal-Si groups, or both;

wherein the Si-ester-Si group comprises a moiety of Formula I:

(I)

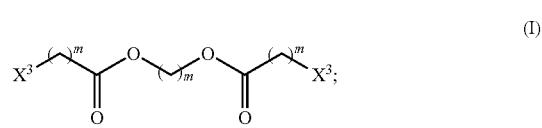

wherein each m is independently 1-8 and each X³ is a silicon atom of the silica nanoparticle matrix; and wherein the Si-acetal-Si group comprises a moiety of Formula II:

(II)

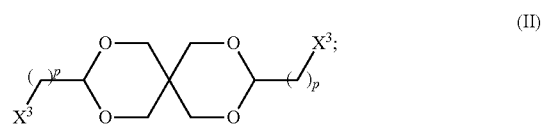

wherein each p is independently 1-8 and each X³ is a silicon atom of the silica nanoparticle matrix.

22. A pharmaceutical composition comprising a plurality of silica nanoparticles of claim 12 and a pharmaceutically acceptable diluent, excipient, or carrier.

23. A pharmaceutical composition comprising a plurality of silica nanoparticles of claim 21 and a pharmaceutically acceptable diluent, excipient, or carrier.

24. A composition comprising a plurality of silica nanoparticles of claim 21 and a lyoprotectant.

* * * * *